US012630882B2

(12) United States Patent
Kennedy et al.

(10) Patent No.: US 12,630,882 B2
(45) Date of Patent: *May 19, 2026

(54) COMPOSITIONS AND METHODS FOR ISOLATING CELL-FREE DNA

(71) Applicant: GUARDANT HEALTH, INC., Palo Alto, CA (US)

(72) Inventors: Andrew Kennedy, San Diego, CA (US); Ariel Jaimovich, Redwood City, CA (US); Matthew Schultz, Redwood City, CA (US); William J. Greenleaf, Menlo Park, CA (US)

(73) Assignee: Guardant Health, Inc., Palo Alto, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/314,056

(22) Filed: May 8, 2023

(65) Prior Publication Data

US 2023/0323474 A1     Oct. 12, 2023

Related U.S. Application Data

(63) Continuation of application No. 16/778,572, filed on Jan. 31, 2020, now Pat. No. 11,643,693.

(Continued)

(51) Int. Cl.
*C12Q 1/6886*          (2018.01)

(52) U.S. Cl.
CPC ..... *C12Q 1/6886* (2013.01); *C12Q 2600/154* (2013.01); *G01N 2800/50* (2013.01)

(58) Field of Classification Search
CPC ............... C12Q 1/6883; C12Q 1/6886; C12Q 2600/154
See application file for complete search history.

(56) References Cited

U.S. PATENT DOCUMENTS

| 5,648,245 A | 7/1997 | Fire et al. |
| 5,912,148 A | 6/1999 | Eggerding |

(Continued)

FOREIGN PATENT DOCUMENTS

| CN | 109196359 A | 1/2019 |
| EP | 1647600 A2 | 6/2006 |

(Continued)

OTHER PUBLICATIONS

Pleasance, et al. A small-cell lung cancer genome with complex signatures of tobacco exposure. Nature. Jan. 14, 2010;463(7278):184-90. doi: 10.1038/nature08629. Epub Dec. 16, 2009.

(Continued)

*Primary Examiner* — Diana B Johannsen
(74) *Attorney, Agent, or Firm* — Indhu Kanakaraj

(57)          ABSTRACT

Disclosed herein are compositions and methods for isolating DNA, such as cell-free DNA (cfDNA). In some embodiments, the cell-free DNA is from a subject having or suspected of having cancer and/or the cell-free DNA comprises DNA produced by a tumor. In some embodiments, the DNA isolated by the method is captured using a sequence-variable target region set and an epigenetic target region set, wherein the sequence-variable target region set is captured with a greater capture yield than the epigenetic target region set. In some embodiments, captured cfDNA of the sequence-variable target region set is sequenced to a greater depth of sequencing than captured cfDNA of the epigenetic target region set.

29 Claims, 4 Drawing Sheets

Related U.S. Application Data

(60) Provisional application No. 62/799,637, filed on Jan. 31, 2019.

(56) References Cited

U.S. PATENT DOCUMENTS

| | | | |
|---|---|---|---|
| 5,952,170 A | 9/1999 | Stroun et al. |
| 6,130,073 A | 10/2000 | Eggerding |
| 6,210,891 B1 | 4/2001 | Nyren et al. |
| 6,258,568 B1 | 7/2001 | Nyren |
| 6,492,121 B2 | 12/2002 | Kurane et al. |
| 6,582,908 B2 | 6/2003 | Fodor et al. |
| 6,586,177 B1 | 7/2003 | Shuber |
| 6,818,395 B1 | 11/2004 | Quake et al. |
| 6,833,246 B2 | 12/2004 | Balasubramanian |
| 6,849,403 B1 | 2/2005 | Shuber |
| 6,858,412 B2 | 2/2005 | Willis et al. |
| 6,911,345 B2 | 6/2005 | Quake et al. |
| 6,964,846 B1 | 11/2005 | Shuber |
| 6,969,488 B2 | 11/2005 | Bridgham et al. |
| 7,115,400 B1 | 10/2006 | Adessi et al. |
| 7,163,789 B2 | 1/2007 | Chen et al. |
| 7,169,560 B2 | 1/2007 | Lapidus et al. |
| 7,170,050 B2 | 1/2007 | Turner et al. |
| 7,282,337 B1 | 10/2007 | Harris |
| 7,302,146 B2 | 11/2007 | Turner et al. |
| 7,313,308 B2 | 12/2007 | Turner et al. |
| 7,329,492 B2 | 2/2008 | Hardin et al. |
| 7,410,764 B2 | 8/2008 | Gocke et al. |
| 7,424,371 B2 | 9/2008 | Kamentsky |
| 7,476,503 B2 | 1/2009 | Turner et al. |
| 7,482,120 B2 | 1/2009 | Buzby |
| 7,501,245 B2 | 3/2009 | Quake et al. |
| 7,537,897 B2 | 5/2009 | Brenner et al. |
| 7,537,898 B2 | 5/2009 | Bost et al. |
| 7,700,286 B2 | 4/2010 | Stroun et al. |
| 7,727,720 B2 | 6/2010 | Dhallan |
| 7,803,929 B2 | 9/2010 | Melkonyan et al. |
| 7,811,757 B2 | 10/2010 | Shuber |
| 7,824,889 B2 | 11/2010 | Vogelstein et al. |
| 7,838,647 B2 | 11/2010 | Hahn et al. |
| 7,915,015 B2 | 3/2011 | Vogelstein et al. |
| 7,935,487 B2 | 5/2011 | Gocke et al. |
| 7,937,225 B2 | 5/2011 | Mishra et al. |
| 7,972,817 B2 | 7/2011 | Kopreski |
| 7,981,612 B2 | 7/2011 | Shuber et al. |
| 8,338,838 B2 | 12/2012 | Sun et al. |
| 8,383,338 B2 | 2/2013 | Kitzman et al. |
| RE44,596 E | 11/2013 | Stroun et al. |
| 8,603,749 B2 | 12/2013 | Gillevet |
| 8,614,073 B2 | 12/2013 | Eijk et al. |
| 8,685,678 B2 | 4/2014 | Casbon et al. |
| 8,741,606 B2 | 6/2014 | Casbon et al. |
| 9,018,365 B2 | 4/2015 | Brenner |
| 9,260,753 B2 | 2/2016 | Xie et al. |
| 9,340,830 B2 | 5/2016 | Lipson et al. |
| 9,376,719 B2 | 6/2016 | Eijk et al. |
| 9,404,156 B2 | 8/2016 | Hicks et al. |
| 9,574,230 B2 | 2/2017 | Eijk et al. |
| 9,598,731 B2 | 3/2017 | Talasaz |
| 9,657,335 B2 | 5/2017 | Eijk et al. |
| 9,670,542 B2 | 6/2017 | Eijk et al. |
| 9,738,894 B2 | 8/2017 | Elmen et al. |
| 9,745,627 B2 | 8/2017 | Eijk et al. |
| 9,850,523 B1 | 12/2017 | Chudova et al. |
| 11,136,619 B2 | 10/2021 | Lipson et al. |
| 11,643,693 B2 * | 5/2023 | Kennedy ............... C12Q 1/6806 |
| | | 435/6.14 |
| 2001/0053519 A1 | 12/2001 | Fodor et al. |
| 2002/0072058 A1 | 6/2002 | Voelker et al. |
| 2003/0082600 A1 | 5/2003 | Olek et al. |
| 2003/0152490 A1 | 8/2003 | Trulson et al. |
| 2005/0221314 A1 | 10/2005 | Berlin et al. |
| 2006/0073506 A1 | 4/2006 | Christians et al. |
| 2006/0188922 A1 | 8/2006 | Corson |
| 2007/0065823 A1 | 3/2007 | Dressman et al. |
| 2008/0014146 A1 | 1/2008 | Hoff et al. |
| 2008/0124721 A1 | 5/2008 | Fuchs et al. |
| 2008/0131887 A1 | 6/2008 | Stephan et al. |
| 2008/0161420 A1 | 7/2008 | Shuber |
| 2009/0029377 A1 | 1/2009 | Lo et al. |
| 2009/0098547 A1 | 4/2009 | Ghosh |
| 2009/0105959 A1 | 4/2009 | Braverman et al. |
| 2009/0162836 A1 | 6/2009 | Widschwendter |
| 2009/0318305 A1 | 12/2009 | Lin et al. |
| 2010/0029498 A1 | 2/2010 | Gnirke et al. |
| 2010/0069250 A1 | 3/2010 | White et al. |
| 2010/0143932 A1 | 6/2010 | Lapidus |
| 2010/0196898 A1 | 8/2010 | Sugarbaker et al. |
| 2010/0323348 A1 | 12/2010 | Hamady et al. |
| 2011/0160078 A1 | 6/2011 | Fodor et al. |
| 2011/0171640 A1 | 7/2011 | Bhatt et al. |
| 2011/0201507 A1 | 8/2011 | Rava et al. |
| 2011/0245482 A1 | 10/2011 | Hahn et al. |
| 2012/0046877 A1 | 2/2012 | Hyland et al. |
| 2012/0095697 A1 | 4/2012 | Halpern et al. |
| 2012/0208706 A1 | 8/2012 | Downing et al. |
| 2012/0316074 A1 | 12/2012 | Saxonov |
| 2013/0005585 A1 | 1/2013 | Anderson et al. |
| 2013/0022977 A1 | 1/2013 | Lapidus et al. |
| 2013/0137588 A1 | 5/2013 | Shendure et al. |
| 2013/0210643 A1 | 8/2013 | Casbon et al. |
| 2013/0224743 A1 | 8/2013 | Casbon et al. |
| 2013/0237458 A1 | 9/2013 | Casbon et al. |
| 2013/0244237 A1 | 9/2013 | Vaisvila et al. |
| 2013/0267424 A1 | 10/2013 | Casbon et al. |
| 2014/0066317 A1 | 3/2014 | Talasaz |
| 2014/0287408 A1 | 9/2014 | Su et al. |
| 2014/0303008 A1 | 10/2014 | Schutz et al. |
| 2015/0126377 A1 | 5/2015 | Gnirke et al. |
| 2015/0299812 A1 | 10/2015 | Talasaz |
| 2015/0368708 A1 | 12/2015 | Talasaz |
| 2016/0032396 A1 | 2/2016 | Diehn et al. |
| 2016/0040229 A1 | 2/2016 | Talasaz et al. |
| 2016/0046986 A1 | 2/2016 | Eltoukhy et al. |
| 2016/0053301 A1 | 2/2016 | Raymond et al. |
| 2016/0060691 A1 | 3/2016 | Giresi et al. |
| 2016/0251704 A1 | 9/2016 | Talasaz et al. |
| 2016/0281166 A1 | 9/2016 | Bhattacharjee et al. |
| 2016/0333417 A1 | 11/2016 | Talasaz |
| 2016/0376647 A1 | 12/2016 | Travers et al. |
| 2017/0024513 A1 | 1/2017 | Lo et al. |
| 2017/0051347 A1 | 2/2017 | Vogelstein et al. |
| 2017/0058332 A1 | 3/2017 | Kermani et al. |
| 2017/0061072 A1 | 3/2017 | Kermani et al. |
| 2017/0073774 A1 | 3/2017 | Lo et al. |
| 2017/0145516 A1 | 5/2017 | Kopetz et al. |
| 2017/0159120 A1 | 6/2017 | Eijk et al. |
| 2017/0166962 A1 | 6/2017 | Eijk et al. |
| 2017/0211143 A1 | 7/2017 | Shendure et al. |
| 2017/0218459 A1 | 8/2017 | Talasaz et al. |
| 2017/0218460 A1 | 8/2017 | Talasaz |
| 2017/0226590 A1 | 8/2017 | Mortimer |
| 2017/0240972 A1 | 8/2017 | Mokhtari et al. |
| 2017/0240973 A1 | 8/2017 | Eltoukhy et al. |
| 2017/0260590 A1 | 9/2017 | Eltoukhy et al. |
| 2017/0342486 A1 | 11/2017 | Eijk et al. |
| 2018/0023125 A1 | 1/2018 | Talasaz et al. |
| 2018/0044731 A1 | 2/2018 | Valouev et al. |
| 2018/0251848 A1 | 9/2018 | Diehn et al. |
| 2018/0305738 A1 | 10/2018 | Kennedy et al. |
| 2019/0017109 A1 | 1/2019 | Song et al. |

FOREIGN PATENT DOCUMENTS

| | | | |
|---|---|---|---|
| EP | 1712639 B1 | 8/2008 |
| EP | 3178941 A1 | 6/2017 |
| EP | 3918089 B1 * | 1/2025 |
| WO | 2000058516 A2 | 10/2000 |
| WO | 2007037678 A2 | 4/2007 |
| WO | 2011063210 A2 | 5/2011 |
| WO | 2011091046 A1 | 7/2011 |
| WO | 2012014877 A1 | 2/2012 |
| WO | 2012054873 A2 | 4/2012 |

(56) References Cited

FOREIGN PATENT DOCUMENTS

| WO | 2012129363 A2 | 9/2012 |
| WO | 2013019075 A2 | 2/2013 |
| WO | 2013060762 A1 | 5/2013 |
| WO | 2014039556 A1 | 3/2014 |
| WO | 2014149134 A2 | 9/2014 |
| WO | 2015100427 A1 | 7/2015 |
| WO | 2015175705 A1 | 11/2015 |
| WO | 2016109452 A1 | 7/2016 |
| WO | 2016179049 A1 | 11/2016 |
| WO | 2017015513 A1 | 1/2017 |
| WO | 2017062867 A1 | 4/2017 |
| WO | 2017062970 A1 | 4/2017 |
| WO | 2017106768 A1 | 6/2017 |
| WO | 2017136603 A1 | 8/2017 |
| WO | 2017151524 A1 | 9/2017 |
| WO | 2017181146 A1 | 10/2017 |
| WO | 2017190215 A1 | 11/2017 |
| WO | 2018009723 A1 | 1/2018 |
| WO | 2018119452 A2 | 6/2018 |
| WO | 2019006269 A1 | 1/2019 |
| WO | 2019136413 A1 | 7/2019 |
| WO | 2019241250 A1 | 12/2019 |
| WO | 2020023420 A2 | 1/2020 |
| WO | 2020243722 A1 | 12/2020 |
| WO | 2021067484 A1 | 4/2021 |
| WO | 2021108708 A1 | 6/2021 |

OTHER PUBLICATIONS

Rhee, H.S et al. "Comprehensive genome-wide protein-DNA interactions detected at single-nucleotide resolution" Cell (2011) 147:1408-1419.

Roy, L et al. "Survival advantage from imatinib compared with the combination interferon-plus cytarabine in chronic- phase chronic myelogenous leukemia: historical comparison between two phase 3 trials" Blood (2006) 108 (5):1478-1484.

Schneider, K.U. et al. "Correlation of SHOX2 Gene Amplification and DNA Methylation in Lung Cancer Tumors" BMC Cancer (2011) 11:102.

Severin, P.M.D. et al. "Cytosine methylation alters DNA mechanical properties" Nucl Acids Res (2011) 39:8740-8751.

Shah, S.P. et al. "Mutational evolution in a lobular breast tumour profiled at single nucleotide resolution" Nature (2009) 461:809-813.

Shah, S.P. et al. "Mutational evolution in a lobular breast tumour profiled at single nucleotide resolution" Nature (2009) 461:809-813; Supplementary Information File 1.

Shah, S.P. et al. "Mutational evolution in a lobular breast tumour profiled at single nucleotide resolution" Nature (2009) 461:809-813; Supplementary Information File 2.

Shah, S.P. et al. "Mutational evolution in a lobular breast tumour profiled at single nucleotide resolution" Nature (2009) 461:809-813; Supplementary Information File 3.

Shah, S.P. et al. "Mutational evolution in a lobular breast tumour profiled at single nucleotide resolution" Nature (2009) 461:809-813; Supplementary Information File 4.

Shi, Y-X et al. "Genome-wide DNA methylation profiling reveals novel epigenetic signatures in squamous cell lung cancer" BMC Genomics (2017) 18:901.

Simpson, et al. Copy number variant detection in inbred strains from short read sequence data. Bioinformatics. Feb. 15, 2010;26(4):565-7. doi: 10.1093/bioinformatics/btp693. Epub Dec. 18, 2009.

Skvortsova, T.E. et al. "Cell-free and cell-bound circulating DNA in breast tumours: DNA quantification and analysis of tumour-related gene methylation" Br J Cancer (2006) 94(10):1492-1495.

Smallwood, S.A. et al. "Single-cell genome-wide bisulfite sequencing for assessing epigenetic heterogeneity" Nature Methods (2014) 11(8):817-820.

Snyder, M.W. et al. "Cell-free DNA Comprises an In Vivo Nucleosome Footprint that Informs Its Tissues-Of-Origin" Cell (2016) 164:57-68 & Supplemental Information.

Song, C-X. et al. "Selective chemical labeling reveals the genome-wide distribution of 5-hydroxymethylcytosine" Nature Biotech (2011) 29:68-72.

Statham, et al. "Genome-wide nucleosome occupancy and DNA methylation profiling of four human cell lines" Genomics Data (Mar. 2015) 3:94-96.

Stephens, P.J. et al. "Complex landscapes of somatic rearrangement in human breast cancer genomes" Nature 462:1005-1010.

Stevens, et al., DNA hybridization on microparticles; determining capture-probe density and equilibrium dissociation constants, Nucleic Acids Research, 1999, 27(7):1719-27.

Stratton, M.R. et al. "The cancer genome" Nature (2009) 458:719-724.

Tan, et al. Genome-wide comparison of DNA hydroxymethylation in mouse embryonic stem cells and neural progenitor cells by a new comparative hMeDIP-seq method. Nucleic Acids Res. Apr. 2013;41(7):e84. doi: 10.1093/nar/gkt091. Epub Feb. 13, 2013.

Taudien, et al. Haplotyping and copy number estimation of the highly polymorphic human beta-defensin locus on 8p23 by 454 amplicon sequencing. BMC Genomics. Apr. 19, 2010;11:252. doi: 10.1186/1471-2164-11-252.

Tewhey, R. et al. "Enrichment of sequencing targets from the human genome by solution hybridization" Genome Biology (2009) 10:R116 (13 pages).

Tomaz, et al. Differential methylation as a cause of allele dropout at the imprinted GNAS locus. Genet Test Mol Biomarkers. Aug. 2010;14(4):455-60. doi: 10.1089/gtmb.2010.0029.

Toyooka, K.O. et al. "Loss of Expression and Aberrant Methylation of the CDH13 (H-Cadherin) Gene in Breast and Lung Carcinomas" Cancer Res. (2001) 61:4556-4560.

Urich, M. et al. "MethylC-seq library preparation for base-resolution whole-genome bisulfite sequencing" Nature Protocols (2015) 10(3):475-483.

Voelkerding, K.V. et al. "Next-generation sequencing: from basic research to diagnostics" Clin Chem (2009) 55:641-658.

Walker, et al. Isothermal in vitro amplification of DNA by a restriction enzyme/DNA polymerase system. Proc Natl Acad Sci U S A. Jan. 1, 1992;89(1):392-6.

Walsh, et al. Detection of inherited mutations for breast and ovarian cancer using genomic capture and massively parallel sequencing. Proc Natl Acad Sci U S A. Jul. 13, 2010;107(28):12629-33. doi: 10.1073/pnas.1007983107. Epub Jun. 28, 2010.

Weber, et al. A real-time polymerase chain reaction assay for quantification of allele ratios and correction of amplification bias. Anal Biochem. Sep. 15, 2003;320(2):252-8.

Wojdacs, et al. Primer design versus PCR bias in methylation independent PCR amplifications. Epigenetics. May 16, 2009;4(4):231-4. Epub May 14, 2009.

Wood, et al. Using next-generation sequencing for high resolution multiplex analysis of copy number variation from nanogram quantities of DNA from formalin-fixed paraffin-embedded specimens. Nucleic Acids Res. Aug. 2010;38(14):e151. doi: 10.1093/nar/gkq510. Epub Jun. 4, 2010.

Yamashita, R. et al. "DBTSS: DataBase of Human Transcription Start Sites, progress report 2006" Nucleic Acids Res. (2006) 34(Database issue): D86-D89.

Yandell, et al. A probabilistic disease-gene finder for personal genomes. Genome Res. Sep. 2011;21(9):1529-42. doi: 10.1101/gr.123158.111. Epub Jun. 23, 2011.

Yassour, M. et al. "Ab initio construction of a eukaryotic transcriptome by massively parallel mRNA sequencing" Nature (2009) 106(9):3264-3269.

Yoon, et al. Sensitive and accurate detection of copy No. variants using read depth of coverage. Genome Res. Sep. 2009;19(9):1586-92. doi: 10.1101/gr.092981.109. Epub Aug. 5, 2009.

Zhang, et al. The impact of next-generation sequencing on genomics. J Genet Genomics. Mar. 20, 2011;38(3):95-109. doi: 10.1016/j.jgg.2011.02.003. Epub Mar. 15, 2011.

Exam Report for European Patent Application No. 20708962.4 dated May 12, 2023.

Office Action for U.S. Appl. No. 16/778,572 dated May 3, 2022.

IPR2017-01448, Petition for Inter Partes Review of U.S. Pat. No. 9,340,830 dated May 17, 2017.

(56)                    References Cited

OTHER PUBLICATIONS

Iurlaro, M. et al. "A screen for hydroxymethylcytosine and formylcytosine binding proteins suggests functions in transcription and chromatin regulation" Genome Biology (2013) 14:R119.
Jakubek, et al., A model of binding on DNA microarrays: understanding the combined effect of probe synthesis failure, cross-hybridization, DNA fragmentation and other experimental details of affymetrix arrays, Jakubek and Cutler BMC Genomics 2012, 13:737, 13 pages.
Katainen, R. et al. "CTCF/cohesin-binding sites are frequently mutated in cancer" Nature Genetics (2015) 47:818-821.
Kenny, E.M. et al. "Multiplex Target Enrichment Using DNA Indexing for Ultra-High Throughput SNP Detection" DNA Res (2010) 18:31-38.
Kikuchi, S. et al. "Promoter Methylation of DAL-1/4.1B Predicts Poor Prognosis in Non Small Cell Lung Cancer" Clin Canc Res (2005) 11:2954-2961.
Kim, D-H. et al. "p16INK4a and Histology-specific Methylation of CpG Islands by Exposure to Tobacco Smoke in Non-Small Cell Lung Cancer" Canc Res (2001) 61:3419-3424.
Kim, D-H. et al. "Promoter methylation of DAP-kinase: association with advanced stage in non-small cell lung cancer" Oncogene. (2001) 20:1765-1770.
Kinde, et al. Detection and quantification of rare mutations with massively parallel sequencing. Proc Natl Acad Sci U S A. Jun. 7, 2011;108(23):9530-5. doi: 10.1073/pnas.1105422108. Epub May 17, 2011.
Koboldt, D.C. et al. "Challenges of sequencing human genomes" Briefings in Bioinformatics (2010) 5:484-498.
Kuo, R. et al. "Benefits and Challenges with Applying Unique Molecular Identifiers in Next Generation Sequencing to Detect Low Frequency Mutations" PLoS One (2016) 11:e146638.
Lam, K. et al. "DNA methylation based biomarkers in colorectal cancer: A systematic review" Biochim Biophys Acta (2016 ) 1866(1):106-20.
Lanman, et al., Analytical and Clinical Validation of a Digital Sequencing Panel for Quantitative, Highly Accurate Evaluation of Cell-Free Circulating Tumor DNA PLoS One, Oct. 2015, 10(10), e0140712. doi: 10.1371/journal.pone.0140712.
Levin, J.Z. et al. "Targeted next generation sequencing of a cancer transcriptome enhances detection of sequence variants and novel fusion transcripts" Genome Biology (2009) 10(10):R115-R115.8; Supplementary Information File 1.
Levin, J.Z. et al. "Targeted next generation sequencing of a cancer transcriptome enhances detection of sequence variants and novel fusion transcripts" Genome Biology (2009) 10(10):R115-R115.8; Supplementary Information File 2.
Levin, J.Z. et al. "Targeted next generation sequencing of a cancer transcriptome enhances detection of sequence variants and novel fusion transcripts" Genome Biology (2009) 10(10):R115-R115.8; Supplementary Information File 3.
Levin, J.Z. et al. "Targeted next generation sequencing of a cancer transcriptome enhances detection of sequence variants and novel fusion transcripts" Genome Biology (2009) 10(10):R115-R115.8; Supplementary Information File 4.
Levin, J.Z. et al. "Targeted next generation sequencing of a cancer transcriptome enhances detection of sequence variants and novel fusion transcripts" Genome Biology (2009) 10(10):R115-R115.8; Supplementary Information File 5.
Levin, J.Z. et al. "Targeted next-generation sequencing of a cancer transcriptome enhances detection of sequence variants and novel fusion transcripts" Genome Biology (2009) 10:R116 (8 pages).
Levy, S.E. et al. "Advancements in Next-Generation Sequencing" Ann Rev Genomics & Hum Genetics (2016) 17:95-115.
Ley, T.J. et al. "DNA sequencing of a cytogenetically normal acute myeloid leukaemia genome" Nature (2008) 456:66-72.
Ley, T.J. et al. "DNA sequencing of a cytogenetically normal acute myeloid leukaemia genome" Nature (2008) 456:66-72; Supplementary Info 1.

Li, et al., The Sequence Alignment/Map format and SAMtools, Bioinformatics, 2009, 25(16):2078-9.
Li, H. "NGS alignment programs" (2009) http://lh3lh3.users.sourceforge.net/NGSalign.shtml.
Li, H. et al., "Fast and accurate short read alignment with Burrows-Wheeler transform," Bioinformatics 2009, 25(14), 1754-1760.
Li, W. et al. "CancerDetector: ultrasensitive and non-invasive cancer detection at the resolution of individual reads using cell-free DNA methylation sequencing data" Nucleic Acids Research (2018) 46(15):e-89-e89.
Licchesi, J. et al. "Epigenetic alteration of Wnt pathway antagonists in progressive glandular neoplasia of the lung" Carcinogenesis (2008) 29:895-904.
Lissa, D. et al. "Methylation analyses in liquid biopsy" Transl Lung Cancer Res (2016) 5(5):492-504.
Liu, L. et al. "Comparison of Next-Generation Sequencing Systems" J Biomed & Biotech (2012) Article ID251364:1-11.
Lizardi, et al. Mutation detection and single-molecule counting using isothermal rolling-circle amplification. Nat Genet. Jul. 1998; 19(3):225-32.
MacLean, D. et al. "Application of 'next-generation' sequencing technologies to microbial genetics" Nature Rev Microbiol (2009) 7:287-296.
Makrigiorgos, et al., A PCR-Based amplification method retaining quantative difference between two complex genomes. Nature Biotech, vol. 20, No. 9, pp. 936-939 (Sep. 2002).
Malhis, N. et al. "High quality SNP calling using Illumina data at shallow coverage" Bioinformatics (2010) 26 (8):1029-1035.
Mamanova, L. et al., "Target-enrichment strategies for next-generation sequencing," Nat. Methods 2010, 7(2), 111-118.
Mardis, E.R. et al. "Recurring Mutations Found by Sequencing an Acute Myeloid Leukemia Genome" New Engl J Med (2009) 361:1058-1066.
Marsh, S. et al. "Pharmacogenetic analysis of paclitaxel transport and metabolism genes in breast cancer" Pharmacogenomics J (2007) 7:362-365.
Martin, D. et al. "Genome-wide CTCF distribution in vertebrates defines equivalent sites that aid the identification of disease-associated genes" Nature Structural Mol Bio (2011) 18:708-714.
Medvedev, et al. Detecting copy number variation with mated short reads. Genome Res. Nov. 2010;20(11):1613-22. doi: 10.1101/gr.106344.110. Epub Aug. 30, 2010.
Mei, et al. Identification of recurrent regions of Copy-Number Variants across multiple individuals. BMC Bioinformatics. Mar. 22, 2010;11:147. doi: 10.1186/1471-2105-11-147.
Metzker, M.L. "Sequencing technologies—the next generation" Nature Reviews Genetics (2010) 11:31-46.
Moore, H.R. et al. "Methylation-sensitive polymerase chain reaction" Methods Mol Bio (2006) 325:239-249.
Nair, S. et al. "Enzymatic cleavage of uracil-containing single-stranded DNA linkers for the efficient release of affinity-selected circulating tumor cells" Chem Commun (2015) 51(15):3266-3269.
Newman, et al. An ultrasensitive method for quantitating circulating tumor DNA with broad patient coverage. Nat Med. May 2014;20(5):548-54. doi: 10.1038/nm.3519. Epub Apr. 6, 2014.
Ning, Z. et al. "SSAHA: A Fast Search Method for Large DNA Databases" Genome Res (2001) 11:1725-1729.
Ogino, et al. Quantification of PCR bias caused by a single nucleotide polymorphism in SMN gene dosage analysis. J Mol Diagn. Nov. 2002;4(4):185-90.
Ooki, A. et al. "A Panel of Novel Detection and Prognostic Methylated DNA Markers in Primary Non-Small Cell Lung Cancer and Serum DNA" (2017) Clin. Cancer Res. 23:7141-7152.
Palmisano, W. et al. "Aberrant Promoter Methylation of the Transcription Factor Genes PAX5 alpha and beta in Human Cancers" Cancer Res (2003) 63:4620-4625.
Park, et al. Discovery of common Asian copy number variants using integrated high-resolution array CGH and massively parallel DNA sequencing. Nat Genet. May 2010;42(5):400-5. doi: 10.1038/ng.555. Epub Apr. 4, 2010.

(56)　　　　　　　References Cited

OTHER PUBLICATIONS

Paweletz, C.P. et al. "Bias-corrected targeted next-generation sequencing for rapid, multiplexed detection of actionable alterations in cell-free DNA from advanced lung cancer patients" Clin Canc Res (2016) 22(4):915-922.

Phallen, J. et al. "Direct detection of early-stage cancers using circulating tumor DNA" Sci Trans Med (2017) vol. 9, Issue 403, eaan2415DOI: 10.1126/scitranslmed.aan2415.

"Sliderll: High quality SNP calling using Illumina data at minimal coverage" (2009) Canada's Michael Smith Genome Sciences Centre.

Agilent Protocol "SureSelect Target Enrichment System: Illumina Single-End Sequencing Platform Library Prep" Apr. 2009.

Alkan, et al. Personalized copy number and segmental duplication maps using next-generation sequencing. Nat Genet. Oct. 2009;41(10):1061-7. doi: 10.1038/ng.437. Epub Aug. 30, 2009.

Astier, Y. et al. "Toward Single Molecule DNA Sequencing: Direct Identification of Ribonucleoside and Deoxyribonucleoside 5'-Monophosphates by Using an Engineered Protein Nanopore Equipped with a Molecular Adapter" J Am Chem Soc (2006) 128(5):1705-1710.

Atanur, et al. The genome sequence of the spontaneously hypertensive rat: Analysis and functional significance. Genome Res. Jun. 2010;20(6):791-803. doi: 10.1101/gr.103499.109. Epub Apr. 29, 2010.

Belinsky, S.A. "Unmasking the lung cancer epigenome" Annu. Rev. Physiol. (2015) 77:453-474.

Bock, C. et al. "Quantitative comparison of genome-wide DNA methylation mapping technologies" Nature Biotech (2010) 28:1106-1114.

Bonaldo, et al. Normalization and subtraction: two approaches to facilitate gene discovery. Genome Res. Sep. 1996;6(9):791-806.

Campbell, P.J. et al. "Subclonal phylogenetic structures in cancer revealed by ultra-deep sequencing" PNAS (2008) 105(35):13081-13086.

Cancer Genome Atlas Research Network "Comprehensive molecular characterization of urothelial bladder carcinoma" Nature (2014) 507:315-322.

Carr, et al. Inferring relative proportions of DNA variants from sequencing electropherograms. Bioinformatics. Dec. 15, 2009;25(24):3244-50. doi: 10.1093/bioinformatics/btp583. Epub Oct. 9, 2009.

Castle, et al. DNA copy number including telomeres and mitochondria, assayed using next-generation sequencing. BMC Genomics. Apr. 16, 2010;11:244. doi: 10.1186/1471-2164-11-244.

Chang, et al. Detection of allelic imbalance in ascitic supernatant by digital single nucleotide polymorphism analysis. Clin Cancer Res. Aug. 2002;8(8):2580-5.

Chmielecki, J. et al. "Targeted next-generation sequencing of DNA regions proximal to a conserved GXGXXG signaling motif enables systematic discovery of tyrosine kinase fusions in cancer" Nucleic Acids Res (2010) 38 (20):6985-6996.

Clark, T.A. et al. "Analytical Validation of a Hybrid Capture Based Next-Generation Sequencing Clinical Assay for Genomic Profiling of Cell-Free Circulating Tumor DNA," J. Mol. Diagnostics (2018) 20(5):686-702.

Co-pending U.S. Appl. No. 14/039,168, filed Sep. 27, 2013.

Costello, et al. Discovery and characterization of artifactual mutations in deep coverage targeted capture sequencing data due to oxidative DNA damage during sample preparation. Nucleic Acids Res. Apr. 1, 2013;41(6):e67. doi: 10.1093/nar/gks1443. Epub Jan. 8, 2013.

Craig, et al. Identification of genetic variants using bar-coded multiplexed sequencing. Nat Methods. Oct. 2008;5(10):887-893. doi: 10.1038/nmeth.1251. Epub Sep. 14, 2008. Supplementary Info.

Craig, et al. Identification of genetic variants using bar-coded multiplexed sequencing. Nat Methods. Oct. 2008;5(10):887-93. doi: 10.1038/nmeth.1251. Epub Sep. 14, 2008.

Cuddapah, S. et al. "Global analysis of the insulator binding protein CTCF in chromatin barrier regions reveals demarcation of active and repressive domains" Genome Res (2009) 19:24-32.

Cummings, N. et al. "Combining target enrichment with barcode multiplexing for high throughput SNP discovery" BMC Genomics (2010) 11:641.

Daines, et al. High-throughput multiplex sequencing to discover copy number variants in Drosophila. Genetics. Aug. 2009;182(4):935-41. doi: 10.1534/genetics.109.103218. Epub Jun. 15, 2009.

Danecek, P. et al. "The variant call format and VCFtools" Bioinformatics (2011) 27(15):2156-2158.

Ehrlich, M. "DNA hypomethylation in cancer cells" Epigenomics 1:239-259, 2009.

Ellison et al. EGFR mutation testing in lung ancer: a review of available methods and their use for analysis of tumour tissue and cytology samples Journal of Clinical Pathology vol. 66, pp. 79-89 (2013).

European Exam Report dated for 20708962.4, dated Nov. 8, 2022.

Fan, et al. Non-invasive prenatal measurement of the fetal genome. Nature. Jul. 19, 2012;487(7407):320-4. doi: 10.1038/nature 11251.

Forbes, S.A. et al. "COSMIC: mining complete cancer genomes in the Catalogue of Somatic Mutations in Cancer" Nucleic Acids Res (2010) 39:D945-D950.

Forbes, S.A. et al. "The Catalogue of Somatic Mutations in Cancer (COSMIC)" Current Prot Human Genet (2008) 10.11.1-10.11.26.

Freier, S.M. et al. "The ups and downs of nucleic acid duplex stability: structure-stability studies on chemically-modified DNA:RNA duplexes" Nucl Acids Res (1997) 25:4429-4443.

Furonaka, O. et al. "Aberrant methylation and loss of expression of O6-methylguanine-DNA methyltransferase in pulmonary squamous cell carcinoma and adenocarcinoma" Pathol Int (2005) 55:303-309.

Gale, D. et al. "Development of a highly sensitive liquid biopsy platform to detect clinically-relevant cancer mutations at low allele fractions in cell-free DNA" PLoS One (2018) 13:e0194630.

Garber, K. "Fixing the front end" Nature Biotech (2008) 26(10):1101-1104.

Gnirke et al. Solution hybrid selection with ultra-long oligonucleotides for maddively parallel targeted sequencing Nature Biotechnology vol. 27, pp. 182-189 (2009).

Gomes, A. et al. "Promoter hypermethylation of DNA repair genes MLH1 and MSH2 in adenocarcinomas and squamous cell carcinomas of the lung" Rev. Port. Pneumol. (2014) 20:20-30.

Grant, et al. SNP genotyping on a genome-wide amplified DOP-PCR template. Nucleic Acids Res. Nov. 15, 2002;30 (22):e25.

Gundry, et al. "Direct mutation analysis by high-throughput sequencing: from germline to low-abundant, somatic variants" Mutat Res Jan. 3, 2012; 729(1-2):1-15. doi: 10.1016/mrfmmm.2011.10.001. Pub Oct. 12, 2011.

Gundry, et al. Direct, genome-wide assessment of DNA mutations in single cells. Nucleic Acids Res. Mar. 2012;40(5):2032-40. doi: 10.1093/nar/gkr949. Epub Nov. 15, 2011.

Guo, M. et al. "Hypermethylation of the GATA genes in lung cancer" Clin Cancer Res (2004) 10(23):7917-7924.

Guo, Y.A. et al. "Mutation hotspots at CTCF binding sites coupled to chromosomal instability in gastrointestinal cancers" Nature Commun (2018) 9:1520.

Hamady, et al. Error-correcting barcoded primers for pyrosequencing hundreds of samples in multiplex. Nat Methods. Mar. 2008;5(3):235-7. doi: 10.1038/nmeth.1184. Epub Feb. 10, 2008.

Heller, G. et al. "Expression and methylation pattern of TSLC1 cascade genes in lung carcinomas" Oncogene (2006) 25:959-968.

Hensel, et al. Simultaneous identification of bacterial virulence genes by negative selection. Science. Jul. 21, 1995;269(5222):400-3.

Hiatt, et al. Single molecule molecular inversion probes for targeted, high-accuracy detection of low-frequency variation. Genome Res. May 2013;23(5):843-54. doi: 10.1101/gr.147686.112. Epub Feb. 4, 2013.

Hon, G.C. et al. "Global DNA hypomethylation coupled to repressive chromatin domain formation and gene silencing in breast cancer" Genome Res (2012) 22:246-258.

(56)                    References Cited

OTHER PUBLICATIONS

Hopkins-Donaldson, S. et al. "Silencing of death receptor and caspase-8 expression in small cell lung carcinoma cell lines and tumors by DNA methylation" Cell Death Differ. (2003) 10:356-64.
Hulbert, A. et al. "Early Detection of Lung Cancer Using DNA Promoter Hypermethylation in Plasma and Sputum" Clin. Cancer Res. (2017) 23:1998-2005.
International search report and written opinion for International Patent Application No. PCT/US2020/016120, dated May 14, 2020.
IPR2017-01170, Petition for Inter Partes Review of U.S. Pat. No. 9,340,830 dated Mar. 30, 2017.
IPR2017-01447, Petition for Inter Partes Review of U.S. Pat. No. 9,340,830 dated May 17, 2017.
Exam report for European Patent Application No. 20708962.4 dated Nov. 17, 2023.
Defendant Tempus AI, Inc. Reply Brief in Support of Its Motion to Dismiss the First Amended Complaint Pursuant to Federal Rule of Civil Procedure; filed Jan. 7, 2025; pp. 1-16.
*Guardant Health Inc.* v. *Tempus AI, Inc.*; Tempus Opening Brief; Oct. 21, 2024.
*Tempus* vs. *Guardant* Invalidity Exhibit A dated Aug. 21, 2025 (C.A. No. 24-687-GBW).
*Tempus* vs. *Guardant* Invalidity Exhibit B dated Aug. 21, 2025 (C.A. No. 24-687-GBW).
*Tempus* vs. *Guardant* Invalidity Exhibit C dated Aug. 21, 2025 (C.A. No. 24-687-GBW).
*Tempus* vs. *Guardant* Invalidity Exhibit D dated Aug. 21, 2025 (C.A. No. 24-687-GBW).
*Tempus* vs. *Guardant* Invalidity Exhibit E dated Aug. 21, 2025 (C.A. No. 24-687-GBW).
*Tempus* vs. *Guardant* Invalidity Exhibit F dated Aug. 21, 2025 (C.A. No. 24-687-GBW).
*Tempus* vs. *Guardant* Invalidity Exhibit G dated Aug. 21, 2025 (C.A. No. 24-687-GBW).
*Tempus* vs. *Guardant* Invalidity Exhibit H dated Aug. 21, 2025 (C.A. No. 24-687-GBW).
*Tempus* vs. *Guardant* Invalidity Exhibit I dated Aug. 21, 2025 (C.A. No. 24-687-GBW).
*Tempus* vs. *Guardant* Invalidity Exhibit J dated Aug. 21, 2025 (C.A. No. 24-687-GBW).
*Tempus* vs. *Guardant* Invalidity Exhibit K dated Aug. 21, 2025 (C.A. No. 24-687-GBW).
*Tempus* vs. *Guardant* Invalidity Exhibit L dated Aug. 21, 2025 (C.A. No. 24-687-GBW).
*Tempus* vs. *Guardant* Invalidity Exhibit M dated Aug. 21, 2025 (C.A. No. 24-687-GBW).
*Tempus* vs. *Guardant* Invalidity Exhibit N dated Aug. 21, 2025 (C.A. No. 24-687-GBW).
Chan, K.C.A. et al. "Noninvasive detection of cancer-associated genome-wide hypomethylation and copy number aberrations by plasma DNA bisulfite sequencing" PNAS (2013) 110(47):18761-18768.
Hodges, E. "High definition profiling of mammalian DNA methylation by array capture and single molecule bisulfite sequencing" Genome Research (2009) 19:1593-1605.
Sophia Genetics S.A., Notice of Opposition for European Patent Application No. 20708962.4 dated Oct. 27, 2025, 20 pages.

* cited by examiner

COMPOSITIONS AND METHODS FOR ISOLATING CELL-FREE DNA

CROSS-REFERENCE TO RELATED APPLICATIONS

This application is a continuation of U.S. patent application Ser. No. 16/778,572, filed Jan. 31, 2020, which claims the benefit of priority of U.S. Provisional Patent Application No. 62/799,637, filed Jan. 31, 2019, each of which is incorporated by reference herein for all purposes.

BACKGROUND

Cancer is responsible for millions of deaths per year worldwide. Early detection of cancer may result in improved outcomes because early-stage cancer tends to be more susceptible to treatment.

Improperly controlled cell growth is a hallmark of cancer that generally results from an accumulation of genetic and epigenetic changes, such as copy number variations (CNVs), single nucleotide variations (SNVs), gene fusions, insertions and/or deletions (indels), epigenetic variations include 5-methylation of cytosine (5-methylcytosine) and association of DNA with chromatin proteins and transcription factors.

Biopsies represent a traditional approach for detecting or diagnosing cancer in which cells or tissue are extracted from a possible site of cancer and analyzed for relevant phenotypic and/or genotypic features. Biopsies have the drawback of being invasive.

Detection of cancer based on analysis of body fluids ("liquid biopsies"), such as blood, is an intriguing alternative based on the observation that DNA from cancer cells is released into body fluids. A liquid biopsy is noninvasive (perhaps requiring only a blood draw). However, it has been challenging to develop accurate and sensitive methods for analyzing liquid biopsy material given the low concentration and heterogeneity of cell-free DNA. Isolating the fractions of cell-free DNA useful for further analysis in liquid biopsy procedures is an important part of this process. Accordingly, there is a need for improved methods and compositions for isolating cell-free DNA, e.g., for use in liquid biopsies.

SUMMARY

The present disclosure provides compositions and methods for isolating DNA, such as cell-free DNA. The present disclosure is based in part on the following realization. It can be beneficial to isolate cell-free DNA so as to capture two sets of target regions—a sequence-variable target region set and an epigenetic target region set—wherein the capture yield of the sequence-variable target region set is greater than the capture yield of the epigenetic target region set. In all embodiments described herein involving a sequence-variable target region set and an epigenetic target region set, the sequence-variable target region set comprises regions not present in the epigenetic target region set and vice versa, although in some instances a fraction of the regions may overlap (e.g., a fraction of genomic positions may be represented in both target region sets). The difference in capture yield can allow for deep and hence more accurate sequence determination in the sequence-variable target region set and shallow and broad coverage in the epigenetic target region set, e.g., during concurrent sequencing, such as in the same sequencing cell or in the same pool of material to be sequenced.

The epigenetic target region set can be analyzed in various ways, including methods that do not depend on a high degree of accuracy in sequence determination of specific nucleotides within a target. Examples include determining methylation and/or the distribution and sizes of fragments, which can indicate normal or aberrant chromatin structures in the cells from which the fragments were obtained. Such analyses can be conducted by sequencing and require less data (e.g., number of sequence reads or depth of sequencing coverage) than determining the presence or absence of a sequence mutation such as a base substitution, insertion, or deletion.

In contrast to approaches described herein, isolating an epigenetic target region set and a sequence-variable target region set at the same capture yield would lead to the unnecessary generation of redundant data for the epigenetic target region set and/or provide less accuracy than is desirable in determinations of the genotype of the members of sequence-variable target region set.

The present disclosure aims to meet the need for improved isolation of cell-free DNA and/or provide other benefits. Accordingly, the following exemplary embodiments are provided.

In one aspect, the present disclosure provides a method of isolating cell-free DNA (cfDNA), the method comprising: capturing a plurality of sets of target regions of cfDNA obtained from a test subject, wherein the plurality of target region sets comprises a sequence-variable target region set and an epigenetic target region set, whereby a captured set of cfDNA molecules is produced; wherein cfDNA molecules corresponding to the sequence-variable target region set are captured in the captured set of cfDNA molecules with a greater capture yield than cfDNA molecules corresponding to the epigenetic target region set.

In another aspect, the present disclosure provides a method of isolating cell-free DNA (cfDNA), the method comprising: contacting cfDNA obtained from a test subject with a set of target-specific probes, wherein the set of target-specific probes comprises target-binding probes specific for a sequence-variable target region set and target-binding probes specific for an epigenetic target region set, and the set of target-specific probes is configured to capture cfDNA corresponding to the sequence-variable target region set with a greater capture yield than cfDNA corresponding to the epigenetic target region set, whereby complexes of target-specific probes and cfDNA are formed; and separating the complexes from cfDNA not bound to target-specific probes, thereby providing a captured set of cfDNA molecules. In some embodiments the method further comprises sequencing the captured set of cfDNA molecules. In some embodiments, the method further comprises sequencing the cfDNA molecules corresponding to the sequence-variable target region set to a greater depth of sequencing than the cfDNA molecules corresponding to the epigenetic target region set.

In another aspect, the present disclosure provides a method of identifying the presence of DNA produced by a tumor, the method comprising: collecting cfDNA from a test subject, capturing a plurality of sets of target regions from the cfDNA, wherein the plurality of target region sets comprises a sequence-variable target region set and an epigenetic target region set, whereby a captured set of cfDNA molecules is produced, sequencing the captured cfDNA molecules, wherein the captured cfDNA molecules of the sequence-variable target region set are sequenced to a greater depth of sequencing than the captured cfDNA molecules of the epigenetic target region set.

In another aspect, the present disclosure provides a method of determining a likelihood that a subject has cancer comprising A method of determining a likelihood that a subject has cancer, comprising: a) collecting cfDNA from a test subject, b) capturing a plurality of sets of target regions from the cfDNA, wherein the plurality of target region sets comprises a sequence-variable target region set and an epigenetic target region set, whereby a captured set of cfDNA molecules is produced; c) sequencing the captured cfDNA molecules, wherein the captured cfDNA molecules of the sequence-variable target region set are sequenced to a greater depth of sequencing than the captured cfDNA molecules of the epigenetic target region set; d) obtaining a plurality of sequence reads generated by a nucleic acid sequencer from sequencing the captured cfDNA molecules; e) mapping the plurality of sequence reads to one or more reference sequences to generate mapped sequence reads; and f) processing the mapped sequence reads corresponding to the sequence-variable target region set and to the epigenetic target region set to determine the likelihood that the subject has cancer.

In some embodiments, the captured cfDNA molecules of the sequence-variable target region set are sequenced to at least a 2-fold greater depth of sequencing than the captured cfDNA molecules of the epigenetic target region set. In some embodiments, the captured cfDNA molecules of the sequence-variable target region set are sequenced to at least a 3-fold greater depth of sequencing than the captured cfDNA molecules of the epigenetic target region set. In some embodiments, the captured cfDNA molecules of the sequence-variable target region set are sequenced to a 4-10-fold greater depth of sequencing than the captured cfDNA molecules of the epigenetic target region set. In some embodiments, the captured cfDNA molecules of the sequence-variable target region set are sequenced to a 4-100-fold greater depth of sequencing than the captured cfDNA molecules of the epigenetic target region set.

In some embodiments, the cfDNA amplification comprises the steps of ligating barcode-containing adapters to the cfDNA. In some embodiments, the cfDNA amplification comprises the steps of ligating barcode-containing adapters to the cfDNA.

In some embodiments, capturing the plurality of sets of target regions of cfDNA comprises contacting the cfDNA with target-binding probes specific for the sequence-variable target region set and target-binding probes specific for the epigenetic target region set. In some embodiments, target-binding probes specific for the sequence-variable target region set are present in a higher concentration than the target-binding probes specific for the epigenetic target region set. In some embodiments, target-binding probes specific for the sequence-variable target region set are present in at least a 2-fold higher concentration than the target-binding probes specific for the epigenetic target region set. In some embodiments, target-binding probes specific for the sequence-variable target region set are present in at least a 4-fold or 5-fold higher concentration than the target-binding probes specific for the epigenetic target region set. In some embodiments, target-binding probes specific for the sequence-variable target region set have a higher target binding affinity than the target-binding probes specific for the epigenetic target region set.

In some embodiments, the cfDNA obtained from the test subject is partitioned into at least 2 fractions on the basis of methylation level, and the subsequent steps of the method are performed on each fraction.

In some embodiments, the partitioning step comprises contacting the collected cfDNA with a methyl binding reagent immobilized on a solid support.

In another aspect, the present disclosure provides a collection of target specific probes for capturing cfDNA produced by tumor cells, comprising target-binding probes specific for a sequence-variable target region set and target-binding probes specific for an epigenetic target region set, wherein the capture yield of the target-binding probes specific for the sequence-variable target region set is at least 2-fold higher than the capture yield of the target-binding probes specific for the epigenetic target region set. In some embodiments, the capture yield of the target-binding probes specific for the sequence-variable target region set is at least 4- or 5-fold higher than the capture yield of the target-binding probes specific for the epigenetic target region set.

In some embodiments, there are at least 10 regions in the sequence-variable target region set and at least 100 regions in the epigenetic target region set.

In some embodiments, the probes are present in a single solution. In some embodiments the probes comprise a capture moiety.

In another aspect, the present disclosure provides a system comprising a communication interface that receives, over a communication network, a plurality of sequence reads generated by a nucleic acid sequencer from sequencing a captured set of cfDNA molecules, wherein the captured set of cDNA molecules are obtained by capturing a plurality of sets of target regions from a cfDNA sample, wherein the plurality of sets of target regions comprises a sequence-variable target region set and an epigenetic target region set, wherein the captured cDNA molecules corresponding to the sequence-variable target region are sequenced to a greater depth of sequencing than the captured cfDNA molecules corresponding to the epigenetic target region set; and a controller comprising or capable of accessing, computer readable media comprising non-transitory computer-executable instructions which, when executed by at least one electronic processor perform a method comprising: (i) receiving, over the communication network, the sequence reads generated by the nucleic acid sequencer, (ii) mapping the plurality of sequence reads to one or more reference sequences to generate mapped sequence reads; (iii) processing the mapped sequence reads corresponding to the sequence-variable target region set and to the epigenetic target region set to determine the likelihood that the subject has cancer.

In some embodiments, the depth of sequencing corresponding to the sequence-variable target region set is at least 2-fold greater than the depth of sequencing corresponding to the epigenetic target region set. In some embodiments, the depth of sequencing corresponding to the sequence-variable target region set is at least 3-fold greater than the depth of sequencing corresponding to the epigenetic target region set. In some embodiments, the depth of sequencing corresponding to the sequence-variable target region set is 4-10-fold greater than the depth of sequencing corresponding to the epigenetic target region set. In some embodiments, the depth of sequencing corresponding to the sequence-variable target region set is 4-100-fold greater than the depth of sequencing corresponding to the epigenetic target region set.

In some embodiments, the captured cfDNA molecules of the sequence-variable target region set are pooled with the captured cfDNA molecules of the epigenetic target region set before sequencing. In some embodiments, the captured cfDNA molecules of the sequence-variable target region set and the captured cfDNA molecules of the epigenetic target region set are sequenced in the same sequencing cell.

In some embodiments, the epigenetic target region set comprises a hypermethylation variable target region set. In some embodiments, the epigenetic target region set comprises a hypomethylation variable target region set. In some embodiments, the epigenetic target region set comprises a methylation control target region set.

In some embodiments, the epigenetic target region set comprises a fragmentation variable target region set. In some embodiments, the fragmentation variable target region set comprises transcription start site regions. In some embodiments, the fragmentation variable target region set comprises CTCF binding regions.

In some embodiments, the footprint of the epigenetic target region set is at least 2-fold greater than the size of the sequence-variable target region set. In some embodiments, the footprint of the epigenetic target region set is at least 10-fold greater than the size of the sequence-variable target region set.

In some embodiments, the footprint of sequence-variable target region set is at least 25 kB or 50 kB.

In yet another aspect, the present disclosure provides a composition comprising captured cfDNA, wherein the captured cfDNA comprises captured sequence-variable target regions and captured epigenetic target regions, and the concentration of the sequence-variable target regions is greater than the concentration of the epigenetic target regions, wherein the concentrations are normalized for the footprint size of the sequence-variable target regions and epigenetic target regions.

In some embodiments, the captured cfDNA comprises sequence tags. In some embodiments, the sequence tags comprise barcodes. In some embodiments, the concentration of the sequence-variable target regions is at least 2-fold greater than the concentration of the epigenetic target regions. In some embodiments, the concentration of the sequence-variable target regions is at least 4- or 5-fold greater than the concentration of the epigenetic target regions. In some embodiments, the concentrations are mass per volume concentrations that are normalized for the footprint sizes of the target regions.

In some embodiments, the epigenetic target regions comprise one, two, three, or four of hypermethylation variable target regions; hypomethylation variable target regions; transcription start site regions; and CTCF binding regions; optionally wherein the epigenetic target regions further comprise methylation control target regions.

In some embodiments, the composition is produced according to a method disclosed elsewhere herein. In some embodiments, capturing is performed in a single container.

In some embodiments, the results of the systems and/or methods disclosed herein are used as an input to generate a report. The report may be in a paper or electronic format. For example, information on, and/or information derived from, the sequence information as determined by the methods or systems disclosed herein, can be displayed in such a report. In some embodiments, this information is the cancer status of the subject, as determined by the methods or systems disclosed herein. The methods or systems disclosed herein may further comprise a step of communicating the report to a third party, such as the subject from whom the sample derived or a health care practitioner.

In another aspect, the disclosure provides a method of determining a risk of cancer recurrence in a test subject, the method comprising: collecting DNA originating or derived from a tumor cell from the test subject diagnosed with the cancer at one or more preselected timepoints following one or more previous cancer treatments to the test subject; capturing a plurality of sets of target regions from the DNA, wherein the plurality of target region sets comprises a sequence-variable target region set and an epigenetic target region set, whereby a captured set of DNA molecules is produced; sequencing the captured DNA molecules, wherein the captured DNA molecules of the sequence-variable target region set are sequenced to a greater depth of sequencing than the captured DNA molecules of the epigenetic target region set, whereby a set of sequence information is produced; detecting a presence or absence of DNA originating or derived from a tumor cell at a preselected timepoint using the set of sequence information; and determining a cancer recurrence score that is indicative of the presence or absence of the DNA originating or derived from the tumor cell for the test subject, wherein a cancer recurrence status of the test subject is determined to be at risk for cancer recurrence when the cancer recurrence score is determined to be at or above a predetermined threshold or the cancer recurrence status of the test subject is determined to be at lower risk for cancer recurrence when the cancer recurrence score is below the predetermined threshold.

In another aspect, the disclosure provides a method of classifying a test subject as being a candidate for a subsequent cancer treatment, the method comprising: collecting DNA originating or derived from a tumor cell from the test subject diagnosed with the cancer at one or more preselected timepoints following one or more previous cancer treatments to the test subject; capturing a plurality of sets of target regions from the DNA, wherein the plurality of target region sets comprises a sequence-variable target region set and an epigenetic target region set, whereby a captured set of DNA molecules is produced; sequencing a plurality of captured DNA molecules from the set of DNA molecules, wherein the captured DNA molecules of the sequence-variable target region set are sequenced to a greater depth of sequencing than the captured DNA molecules of the epigenetic target region set, whereby a set of sequence information is produced detecting a presence or absence of DNA originating or derived from a tumor cell at one or more preselected timepoints using the set of sequence information; determining a cancer recurrence score that is indicative of the presence or absence of the DNA originating or derived from the tumor cell; and comparing the cancer recurrence score of the test subject with a predetermined cancer recurrence threshold, thereby classifying the test subject as a candidate for the subsequent cancer treatment when the cancer recurrence score is above the cancer recurrence threshold or not a candidate for therapy when the cancer recurrence score is below the cancer recurrence threshold.

The following is an exemplary list of embodiments according to this disclosure.

Embodiment 1 is a method of isolating cell-free DNA (cfDNA), the method comprising:
    capturing a plurality of sets of target regions of cfDNA obtained from a test subject,
    wherein the plurality of target region sets comprises a sequence-variable target region set and an epigenetic target region set,
    whereby a captured set of cfDNA molecules is produced;
    wherein cfDNA molecules corresponding to the sequence-variable target region set are captured in the captured set of cfDNA molecules with a greater capture yield than cfDNA molecules corresponding to the epigenetic target region set.

Embodiment 2 is a method of isolating cell-free DNA (cfDNA), the method comprising:

contacting cfDNA obtained from a test subject with a set of target-specific probes, wherein the set of target-specific probes comprises target-binding probes specific for a sequence-variable target region set and target-binding probes specific for a epigenetic target region set, and the set of target-specific probes is configured to capture cfDNA corresponding to the sequence-variable target region set with a greater capture yield than cfDNA corresponding to the epigenetic target region set, whereby complexes of target-specific probes and cfDNA are formed; and separating the complexes from cfDNA not bound to target-specific probes, thereby providing a captured set of cfDNA molecules.

Embodiment 3 is the method of embodiment 1 or 2, further comprising sequencing the captured set of cfDNA molecules.

Embodiment 4 is the method of embodiment 3, comprising sequencing the cfDNA molecules corresponding to the sequence-variable target region set to a greater depth of sequencing than the cfDNA molecules corresponding to the epigenetic target region set.

Embodiment 5 is a method of identifying the presence of DNA produced by a tumor, the method comprising:

collecting cfDNA from a test subject, capturing a plurality of sets of target regions from the cfDNA, wherein the plurality of target region sets comprises a sequence-variable target region set and an epigenetic target region set, whereby a captured set of cfDNA molecules is produced, sequencing the captured cfDNA molecules, wherein the captured cfDNA molecules of the sequence-variable target region set are sequenced to a greater depth of sequencing than the captured cfDNA molecules of the epigenetic target region set.

Embodiment 6 is the method of any one of embodiments 3-5, wherein the captured cfDNA molecules of the sequence-variable target region set are sequenced to at least a 2-fold greater depth of sequencing than the captured cfDNA molecules of the epigenetic target region set.

Embodiment 7 is the method of any one of embodiments 3-5, wherein the captured cfDNA molecules of the sequence-variable target region set are sequenced to at least a 3-fold greater depth of sequencing than the captured cfDNA molecules of the epigenetic target region set.

Embodiment 8 is the method of any one of embodiments 3-5, wherein the captured cfDNA molecules of the sequence-variable target region set are sequenced to a 4-10-fold greater depth of sequencing than the captured cfDNA molecules of the epigenetic target region set.

Embodiment 9 is the method of any one of embodiments 3-5, wherein the captured cfDNA molecules of the sequence-variable target region set are sequenced to a 4-100-fold greater depth of sequencing than the captured cfDNA molecules of the epigenetic target region set.

Embodiment 10 is the method of any one of embodiments 3-9, wherein the captured cfDNA molecules of the sequence-variable target region set are pooled with the captured cfDNA molecules of the epigenetic target region set before sequencing.

Embodiment 11 is the method of any one of embodiments 3-10, wherein the captured cfDNA molecules of the sequence-variable target region set and the captured cfDNA molecules of the epigenetic target region set are sequenced in the same sequencing cell.

Embodiment 12 is the method of any one of the preceding embodiments, wherein the cfDNA is amplified before capture.

Embodiment 13 is the method of embodiment 12, wherein the cfDNA amplification comprises the steps of ligating barcode-containing adapters to the cfDNA.

Embodiment 14 is the method of any one of the preceding embodiments, wherein the epigenetic target region set comprises a hypermethylation variable target region set.

Embodiment 15 is the method of any one of the preceding embodiments, wherein the epigenetic target region set comprises a hypomethylation variable target region set.

Embodiment 16 is the method of embodiment 14 or 15, wherein the epigenetic target region set comprises a methylation control target region set.

Embodiment 17 is the method of any one of the preceding embodiments, wherein the epigenetic target region set comprise a fragmentation variable target region set.

Embodiment 18 is the method of embodiment 17, wherein the fragmentation variable target region set comprises transcription start site regions.

Embodiment 19 is the method of embodiment 17 or 18, wherein the fragmentation variable target region set comprises CTCF binding regions.

Embodiment 20 is the method of any one of the preceding embodiments, wherein capturing the plurality of sets of target regions of cDNA comprises contacting the cfDNA with target-binding probes specific for the sequence-variable target region set and target-binding probes specific for the epigenetic target region set.

Embodiment 21 is the method of embodiment 20, wherein target-binding probes specific for the sequence-variable target region set are present in a higher concentration than the target-binding probes specific for the epigenetic target region set.

Embodiment 22 is the method of embodiment 20, wherein target-binding probes specific for the sequence-variable target region set are present in at least a 2-fold higher concentration than the target-binding probes specific for the epigenetic target region set.

Embodiment 23 is the method of embodiment 20, wherein target-binding probes specific for the sequence-variable target region set are present in at least a 4-fold or 5-fold higher concentration than the target-binding probes specific for the epigenetic target region set.

Embodiment 24 is the method of any one of embodiments 20-23, wherein target-binding probes specific for the sequence-variable target region set have a higher target binding affinity than the target-binding probes specific for the epigenetic target region set.

Embodiment 25 is the method of any one of the preceding embodiments, wherein the footprint of the epigenetic target region set is at least 2-fold greater than the size of the sequence-variable target region set.

Embodiment 26 is the method of embodiment 25, wherein the footprint of the epigenetic target region set is at least 10-fold greater than the size of the sequence-variable target region set.

Embodiment 27 is the method of any one of the preceding embodiments, wherein the footprint of sequence-variable target region set is at least 25 kB or 50 kB.

Embodiment 28 is the method of any one of the preceding embodiments, wherein the cfDNA obtained from the test subject is partitioned into at least 2 fractions on the basis of methylation level, and the subsequent steps of the method are performed on each fraction.

Embodiment 29 is the method of embodiment 28, wherein the partitioning step comprises contacting the collected cfDNA with a methyl binding reagent immobilized on a solid support.

Embodiment 30 is the method of embodiment 28 or 29, wherein the at least 2 fractions comprise a hypermethylated fraction and a hypomethylated fraction, and the method further comprises differentially tagging the hypermethylated fraction and the hypomethylated fraction or separately sequencing the hypermethylated fraction and the hypomethylated fraction.

Embodiment 31 is the method of embodiment 30, wherein the hypermethylated fraction and the hypomethylated fraction are differentially tagged and the method further comprises pooling the differentially tagged hypermethylated and hypomethylated fractions before a sequencing step.

Embodiment 32 is the method of any one of the preceding embodiments, further comprising determining whether cfDNA molecules corresponding to the sequence-variable target region set comprise cancer-associated mutations.

Embodiment 33 is the method of any one of the preceding embodiments, further comprising determining whether cfDNA molecules corresponding to the epigenetic target region set comprise or indicate cancer-associated epigenetic modifications or copy number variations (e.g., focal amplifications), optionally wherein the method comprises determining whether cfDNA molecules corresponding to the epigenetic target region set comprise or indicate cancer-associated epigenetic modifications and copy number variations (e.g., focal amplifications).

Embodiment 34 is the method of embodiment 33, wherein the cancer-associated epigenetic modifications comprise hypermethylation in one or more hypermethylation variable target regions.

Embodiment 35 is the method of embodiment 33 or 34, wherein the cancer-associated epigenetic modifications comprise one or more perturbations of CTCF binding.

Embodiment 36 is the method of any one of embodiments 33-35, wherein the cancer-associated epigenetic modifications comprise one or more perturbations of transcription start sites.

Embodiment 37 is the method of any one of the preceding embodiments, wherein the captured set of cfDNA molecules is sequenced using high-throughput sequencing, pyrosequencing, sequencing-by-synthesis, single-molecule sequencing, nanopore-based sequencing, semiconductor sequencing, sequencing-by-ligation, sequencing-by-hybridization, RNA-Seq (Illumina), Digital Gene Expression (Helicos), next generation sequencing (NGS), Single Molecule Sequencing by Synthesis (SMSS) (Helicos), massively-parallel sequencing, Clonal Single Molecule Array (Solexa), shotgun sequencing, Ion Torrent, Oxford Nanopore, Roche Genia, Maxim-Gilbert sequencing, primer walking, sequencing using PacBio, SOLiD, Ion Torrent, or a Nanopore platform.

Embodiment 38 is a collection of target specific probes for capturing cfDNA produced by tumor cells, comprising target-binding probes specific for a sequence-variable target region set and target-binding probes specific for an epigenetic target region set, wherein the capture yield of the target-binding probes specific for the sequence-variable target region set is at least 2-fold higher than the capture yield of the target-binding probes specific for the epigenetic target region set.

Embodiment 39 is the collection of target specific probes of embodiment 38, wherein the capture yield of the target-binding probes specific for the sequence-variable target region set is at least 4- or 5-fold higher than the capture yield of the target-binding probes specific for the epigenetic target region set.

Embodiment 40 is the collection of target specific probes of embodiment 38 or 39, wherein the epigenetic target region set comprises a hypermethylation variable target region probe set.

Embodiment 41 is the collection of target specific probes of any one of embodiments 38-40, wherein the epigenetic target region set comprises a hypomethylation variable target region probe set.

Embodiment 42 is the collection of target specific probes of embodiment 40 or 41, wherein the epigenetic target region probe set comprises a methylation control target region probe set.

Embodiment 43 is the collection of target specific probes of any one of embodiments 38-42, wherein the epigenetic target region probe set comprise a fragmentation variable target region probe set.

Embodiment 44 is the collection of target specific probes of embodiment 43, wherein the fragmentation variable target region probe set comprises transcription start site region probes.

Embodiment 45 is the collection of target specific probes of embodiment 43 or 44, wherein the fragmentation variable target region probe set comprises CTCF binding region probes.

Embodiment 46 is the collection of target specific probes of any one of embodiments 38-45, wherein there are at least 10 regions in the sequence-variable target region set and at least 100 regions in the epigenetic target region set.

Embodiment 47 is the collection of target specific probes of any one of embodiments 38-46, wherein the footprint of the epigenetic target region set is at least 2-fold greater than the size of the sequence-variable target region set.

Embodiment 48 is the collection of target specific probes of embodiment 47, wherein the footprint of the epigenetic target region set is at least 10-fold greater than the size of the sequence-variable target region set.

Embodiment 49 is the collection of target specific probes of any one of embodiments 38-48, wherein the footprint of sequence-variable target region set is at least 25 kB or 50 kB.

Embodiment 50 is the collection of target specific probes of any one of embodiments 38-49, wherein the probes are present in a single solution.

Embodiment 51 is the collection of target specific probes of any one of embodiments 38-50, wherein the probes comprise a capture moiety.

Embodiment 52 is a composition comprising captured cfDNA, wherein the captured cfDNA comprises captured sequence-variable target regions and captured epigenetic target regions, and the concentration of the sequence-variable target regions is greater than the concentration of the epigenetic target regions, wherein the concentrations are normalized for the footprint size of the sequence-variable target regions and epigenetic target regions.

Embodiment 53 is the composition of embodiment 52, wherein the captured cfDNA comprises sequence tags.

Embodiment 54 is the composition of embodiment 53, wherein the sequence tags comprise barcodes.

Embodiment 55 is the composition of any one of embodiments 52-54, wherein the concentration of the sequence-variable target regions is at least 2-fold greater than the concentration of the epigenetic target regions.

Embodiment 56 is the composition of any one of embodiments 52-54, wherein the concentration of the sequence-variable target regions is at least 4- or 5-fold greater than the concentration of the epigenetic target regions.

Embodiment 57 is the composition of any one of embodiments 52-56, wherein the concentrations are mass per volume concentrations that are normalized for the footprint sizes of the target regions.

Embodiment 58 is the composition of any one of embodiments 52-57, wherein the epigenetic target regions comprise one, two, three, or four of hypermethylation variable target regions; hypomethylation variable target regions; transcription start site regions; and CTCF binding regions; optionally wherein the epigenetic target regions further comprise methylation control target regions.

Embodiment 59 is the composition of any one of embodiments 52-58, which is produced according to the method of any one of embodiments 1-37.

Embodiment 60 is a method of determining a likelihood that a subject has cancer, comprising:

collecting cfDNA from a test subject;

capturing a plurality of sets of target regions from the cfDNA;

wherein the plurality of target region sets comprises a sequence-variable target region set and an epigenetic target region set, whereby a captured set of cfDNA molecules is produced;

sequencing the captured cfDNA molecules, wherein the captured cfDNA molecules of the sequence-variable target region set are sequenced to a greater depth of sequencing than the captured cfDNA molecules of the epigenetic target region set;

obtaining a plurality of sequence reads generated by a nucleic acid sequencer from sequencing the captured cfDNA molecules;

mapping the plurality of sequence reads to one or more reference sequences to generate mapped sequence reads;

processing the mapped sequence reads corresponding to the sequence-variable target region set and to the epigenetic target region set to determine the likelihood that the subject has cancer.

Embodiment 61 is the method of embodiment 60, having the features recited in any of embodiments 21-38.

Embodiment 62 is the method of embodiment 60 or 61, wherein the captured cfDNA molecules of the sequence-variable target region set are pooled with the captured cfDNA molecules of the epigenetic target region set before obtaining the plurality of sequence reads and/or are sequenced in the same sequencing cell.

Embodiment 63 is the method of any one of embodiments 60-62, wherein the cfDNA is amplified before capture, optionally wherein the cfDNA amplification comprises the steps of ligating barcode-containing adapters to the cfDNA.

Embodiment 64 is the method of any one of embodiments 60-63, wherein the epigenetic target region set is as recited in any of embodiments 15-19.

Embodiment 65 is the method of any one of embodiments 60-64, wherein capturing the plurality of sets of target regions of cDNA comprises contacting the cfDNA with target-binding probes specific for the sequence-variable target region set and target-binding probes specific for the epigenetic target region set.

Embodiment 66 is a system, comprising:

a communication interface that receives, over a communication network, a plurality of sequence reads generated by a nucleic acid sequencer from sequencing a captured set of cfDNA molecules, wherein the captured set of cDNA molecules are obtained by capturing a plurality of sets of target regions from a cfDNA sample, wherein the plurality of sets of target regions comprises a sequence-variable target region set and an epigenetic target region set, wherein the captured cfDNA molecules corresponding to the sequence-variable target region are sequenced to a greater depth of sequencing than the captured cfDNA molecules corresponding to the epigenetic target region set; and a controller comprising or capable of accessing, computer readable media comprising non-transitory computer-executable instructions which, when executed by at least one electronic processor perform a method comprising:

(i) receiving, over the communication network, the sequence reads generated by the nucleic acid sequencer;

(ii) mapping the plurality of sequence reads to one or more reference sequences to generate mapped sequence reads;

(iii) processing the mapped sequence reads corresponding to the sequence-variable target region set and to the epigenetic target region set to determine the likelihood that the subject has cancer.

Embodiment 67 is the system of embodiment 66, wherein the depth of sequencing corresponding to the sequence-variable target region set is at least 2-fold greater than the depth of sequencing corresponding to the epigenetic target region set.

Embodiment 68 is the system of embodiment 66, wherein the depth of sequencing corresponding to the sequence-variable target region set is at least 3-fold greater than the depth of sequencing corresponding to the epigenetic target region set.

Embodiment 69 is the system of embodiment 66, wherein the depth of sequencing corresponding to the sequence-variable target region set is 4-10-fold greater than the depth of sequencing corresponding to the epigenetic target region set.

Embodiment 70 is the system of any one of embodiment 66, wherein the depth of sequencing corresponding to the sequence-variable target region set is 4-100-fold greater than the depth of sequencing corresponding to the epigenetic target region set.

Embodiment 71 is the system of any one of embodiments 66-70, wherein the captured cfDNA molecules of the sequence-variable target region set are pooled with the captured cfDNA molecules of the epigenetic target region set before sequencing.

Embodiment 72 is the system of any one of embodiments 66-71, wherein the captured cfDNA molecules of the sequence-variable target region set and the captured cfDNA molecules of the epigenetic target region set are sequenced in the same sequencing cell.

Embodiment 73 is the system of any one of embodiments 66-72, wherein the epigenetic target region set comprises a hypermethylation variable target region set.

Embodiment 74 is the system of any one of embodiments 66-73, wherein the epigenetic target region set comprises a hypomethylation variable target region set.

Embodiment 75 is the system of embodiment 72 or 73, wherein the epigenetic target region set comprises a methylation control target region set.

Embodiment 76 is the system of any one of 66-75, wherein the epigenetic target region set comprises a fragmentation variable target region set.

Embodiment 77 is the system of any one of embodiments 66-76, wherein the fragmentation variable target region set comprises transcription start site regions.

Embodiment 78 is the system of embodiment 76 or 77, wherein the fragmentation variable target region set comprises CTCF binding regions.

Embodiment 79 is the system of any one of embodiments 66-78, wherein the footprint of the epigenetic target region set is at least 2-fold greater than the size of the sequence-variable target region set.

Embodiment 80 is the system of embodiment 79, wherein the footprint of the epigenetic target region set is at least 10-fold greater than the size of the sequence-variable target region set.

Embodiment 81 is the system of any one of embodiments 66-80, wherein the footprint of sequence-variable target region set is at least 25 kB or 50 kB.

Embodiment 82 is the method or system of any one of the above embodiments, wherein the capturing is performed in a single container.

Embodiment 83 is the method of any one of embodiments 1-37, wherein the test subject was previously diagnosed with a cancer and received one or more previous cancer treatments, optionally wherein the cfDNA is obtained at one or more preselected time points following the one or more previous cancer treatments.

Embodiment 84 is the method of the immediately preceding embodiment, further comprising sequencing the captured set of cfDNA molecules, whereby a set of sequence information is produced.

Embodiment 85 is the method of the immediately preceding embodiment, wherein the captured DNA molecules of the sequence-variable target region set are sequenced to a greater depth of sequencing than the captured DNA molecules of the epigenetic target region set.

Embodiment 86 is the method of embodiment 84 or 85, further comprising detecting a presence or absence of DNA originating or derived from a tumor cell at a preselected timepoint using the set of sequence information.

Embodiment 87 is the method of the immediately preceding embodiment, further comprising determining a cancer recurrence score that is indicative of the presence or absence of the DNA originating or derived from the tumor cell for the test subject.

Embodiment 88 is the method of the immediately preceding embodiment, further comprising determining a cancer recurrence status based on the cancer recurrence score, wherein the cancer recurrence status of the test subject is determined to be at risk for cancer recurrence when a cancer recurrence score is determined to be at or above a predetermined threshold or the cancer recurrence status of the test subject is determined to be at lower risk for cancer recurrence when the cancer recurrence score is below the predetermined threshold.

Embodiment 89 is the method of embodiment 87 or 88, further comprising comparing the cancer recurrence score of the test subject with a predetermined cancer recurrence threshold, and the test subject is classified as a candidate for a subsequent cancer treatment when the cancer recurrence score is above the cancer recurrence threshold or not a candidate for a subsequent cancer treatment when the cancer recurrence score is below the cancer recurrence threshold.

Embodiment 90 is a method of determining a risk of cancer recurrence in a test subject, the method comprising:
    (a) collecting DNA originating or derived from a tumor cell from the test subject diagnosed with the cancer at one or more preselected timepoints following one or more previous cancer treatments to the test subject;
    (b) capturing a plurality of sets of target regions from the DNA, wherein the plurality of target region sets comprises a sequence-variable target region set and an epigenetic target region set, whereby a captured set of DNA molecules is produced;
    (c) sequencing the captured DNA molecules, wherein the captured DNA molecules of the sequence-variable target region set are sequenced to a greater depth of sequencing than the captured DNA molecules of the epigenetic target region set, whereby a set of sequence information is produced;
    (d) detecting a presence or absence of DNA originating or derived from a tumor cell at a preselected timepoint using the set of sequence information; and
    (e) determining a cancer recurrence score that is indicative of the presence or absence of the DNA originating or derived from the tumor cell for the test subject, wherein a cancer recurrence status of the test subject is determined to be at risk for cancer recurrence when the cancer recurrence score is determined to be at or above a predetermined threshold or the cancer recurrence status of the test subject is determined to be at lower risk for cancer recurrence when the cancer recurrence score is below the predetermined threshold.

Embodiment 91 is a method of classifying a test subject as being a candidate for a subsequent cancer treatment, the method comprising:
    (a) collecting DNA originating or derived from a tumor cell from the test subject diagnosed with the cancer at one or more preselected timepoints following one or more previous cancer treatments to the test subject;
    (b) capturing a plurality of sets of target regions from the DNA, wherein the plurality of target region sets comprises a sequence-variable target region set and an epigenetic target region set, whereby a captured set of DNA molecules is produced;
    (c) sequencing a plurality of captured DNA molecules from the set of DNA molecules, wherein the captured DNA molecules of the sequence-variable target region set are sequenced to a greater depth of sequencing than the captured DNA molecules of the epigenetic target region set, whereby a set of sequence information is produced;
    (d) detecting a presence or absence of DNA originating or derived from a tumor cell at one or more preselected timepoints using the set of sequence information,
    (e) determining a cancer recurrence score that is indicative of the presence or absence of the DNA originating or derived from the tumor cell; and
    (f) comparing the cancer recurrence score of the test subject with a predetermined cancer recurrence threshold, thereby classifying the test subject as a candidate for the subsequent cancer treatment when the cancer recurrence score is above the cancer recurrence threshold or not a candidate for therapy when the cancer recurrence score is below the cancer recurrence threshold.

Embodiment 92 is the method of embodiment 88-90, wherein the test subject is at risk for cancer recurrence and is classified as a candidate for a subsequent cancer treatment.

Embodiment 93 is the method of any one of embodiments 89, 91, or 92, wherein the subsequent cancer treatment comprises chemotherapy or administration of a therapeutic composition.

Embodiment 94 is the method of any one of embodiments 90-93, wherein the DNA originating or derived from a tumor cell is cell-free DNA.

Embodiment 95 is the method of any one of embodiments 90-93, wherein the DNA originating or derived from a tumor cell is obtained from a tissue sample.

Embodiment 96 is the method of any one of embodiments 87-95, further comprising determining a disease-free survival (DFS) period for the test subject based on the cancer recurrence score.

Embodiment 97 is the method of embodiment 96, wherein the DFS period is 1 year, 2 years, 3, years, 4 years, 5 years, or 10 years.

Embodiment 98 is the method of any one of embodiments 84-97, wherein the set of sequence information comprises sequence-variable target region sequences, and determining the cancer recurrence score comprises determining at least a first subscore indicative of the amount of SNVs, insertions/deletions, CNVs and/or fusions present in sequence-variable target region sequences.

Embodiment 99 is the method of embodiment 98, wherein a number of mutations in the sequence-variable target regions chosen from 1, 2, 3, 4, or 5 is sufficient for the first subscore to result in a cancer recurrence score classified as positive for cancer recurrence, optionally wherein the number of mutations is chosen from 1, 2, or 3.

Embodiment 100 is the method of any one of embodiments 84-99, wherein the set of sequence information comprises epigenetic target region sequences, and determining the cancer recurrence score comprises determining a second subscore indicative of the amount of abnormal sequence reads in the epigenetic target region sequences.

Embodiment 101 is the method of embodiment 100, wherein abnormal sequence reads comprise reads indicative of methylation of hypermethylation variable target sequences and/or reads indicative of abnormal fragmentation in fragmentation variable target regions.

Embodiment 102 is the method of embodiment 101, wherein a proportion of reads corresponding to the hypermethylation variable target region set and/or fragmentation variable target region set that indicate hypermethylation in the hypermethylation variable target region set and/or abnormal fragmentation in the fragmentation variable target region set greater than or equal to a value in the range of 0.001%-10% is sufficient for the second subscore to be classified as positive for cancer recurrence.

Embodiment 103 is the method of embodiment 102, wherein the range is 0.001%-1% or 0.005%-1%.

Embodiment 104 is the method of embodiment 102, wherein the range is 0.01%-5% or 0.01%-2%.

Embodiment 105 is the method of embodiment 102, wherein the range is 0.01%-1%.

Embodiment 106 is the method of any one of embodiments 84-105, further comprising determining a fraction of tumor DNA from the fraction of reads in the set of sequence information that indicate one or more features indicative of origination from a tumor cell.

Embodiment 107 is the method of embodiment 106, wherein the one or more features indicative of origination from a tumor cell comprise one or more of alterations in a sequence-variable target region, hypermethylation of a hypermethylation variable target region, and abnormal fragmentation of a fragmentation variable target region.

Embodiment 108 is the method of embodiment 106 or 107, further comprising determining a cancer recurrence score based at least in part on the fraction of tumor DNA, wherein a fraction of tumor DNA greater than or equal to a predetermined value in the range of $10^{-11}$ to 1 or $10^{-10}$ to 1 is sufficient for the cancer recurrence score to be classified as positive for cancer recurrence.

Embodiment 109 is the method of embodiment 108, wherein a fraction of tumor DNA greater than or equal to a predetermined value in the range of $10^{-10}$ to $10^{-9}$, $10^{-9}$ to $10^{-8}$, $10^{-8}$ to $10^{-7}$, $10^{-7}$ to $10^{-6}$, $10^{-6}$ to $10^{-5}$, $10^{-5}$ to $10^{-4}$, $10^{-4}$ to $10^{-3}$, $10^{-3}$ to $10^{-2}$, or $10^{-2}$ to $10^{-1}$ is sufficient for the caner recurrence score to be classified as positive for caner recurrence.

Embodiment 110 is the method of embodiment 108 or 109, wherein the predetermined value is in the range of $10^{-8}$ to $10^{-6}$ or is $10^{-7}$.

Embodiment 111 is the method of any one of embodiments 107-110, wherein the fraction of tumor DNA is determined as greater than or equal to the predetermined value if the cumulative probability that the fraction of tumor DNA is greater than or equal to the predetermined value is at least 0.5, 0.75, 0.9, 0.95, 0.98, 0.99, 0.995, or 0.999.

Embodiment 112 is the method of embodiment 111, wherein the cumulative probability is at least 0.95.

Embodiment 113 is the method of embodiment 111, wherein the cumulative probability is in the range of 0.98-0.995 or is 0.99.

Embodiment 114 is the method of any one of embodiments 84-113, wherein the set of sequence information comprises sequence-variable target region sequences and epigenetic target region sequences, and determining the cancer recurrence score comprises determining a first subscore indicative of the amount of SNVs, insertions/deletions, CNVs and/or fusions present in sequence-variable target region sequences and a second subscore indicative of the amount of abnormal sequence reads in epigenetic target region sequences, and combining the first and second subscores to provide the cancer recurrence score.

Embodiment 115 is the method of embodiment 114, wherein combining the first and second subscores comprises applying a threshold to each subscore independently (e.g., greater than a predetermined number of mutations (e.g., >1) in sequence-variable target regions, and greater than a predetermined fraction of abnormal (e.g., tumor) reads in epigenetic target regions), or training a machine learning classifier to determine status based on a plurality of positive and negative training samples.

Embodiment 116 is the method of embodiment 115, wherein a value for the combined score in the range of −4 to 2 or −3 to 1 is sufficient for the cancer recurrence score to be classified as positive for cancer recurrence.

Embodiment 117 is the method of any one of embodiments 83-116, wherein the one or more preselected timepoints is selected from the following group consisting of 1 month, 2 months, 3 months, 4 months, 5 months, 6 months, 7 months, 8 months, 9 months, 10 months, 11 months, 1 year, 1.5 years, 2 year, 3 years, 4 and 5 years after administration of the one or more previous cancer treatments.

Embodiment 118 is the method of any one of embodiments 83-117, wherein the cancer is colorectal cancer.

Embodiment 119 is the method of any one of embodiments 83-118, wherein the one or more previous cancer treatments comprise surgery.

Embodiment 120 is the method of any one of embodiments 83-119, wherein the one or more previous cancer treatments comprise administration of a therapeutic composition.

Embodiment 121 is the method of any one of embodiments 83-120, wherein the one or more previous cancer treatments comprise chemotherapy.

The various steps of the methods disclosed herein, or the steps carried out by the systems disclosed herein, may be carried out at the same time or different times, and/or in the same geographical location or different geographical locations, e.g. countries. The various steps of the methods disclosed herein can be performed by the same person or different people.

BRIEF DESCRIPTION OF THE DRAWINGS

The accompanying drawings, which are incorporated in and constitute a part of this specification, illustrate certain embodiments, and together with the written description, serve to explain certain principles of the methods, computer readable media, and systems disclosed herein. The description provided herein is better understood when read in conjunction with the accompanying drawings which are included by way of example and not by way of limitation. It will be understood that like reference numerals identify like components throughout the drawings, unless the context indicates otherwise. It will also be understood that some or all of the figures may be schematic representations for purposes of illustration and do not necessarily depict the actual relative sizes or locations of the elements shown.

DETAILED DESCRIPTION

Figure 1:
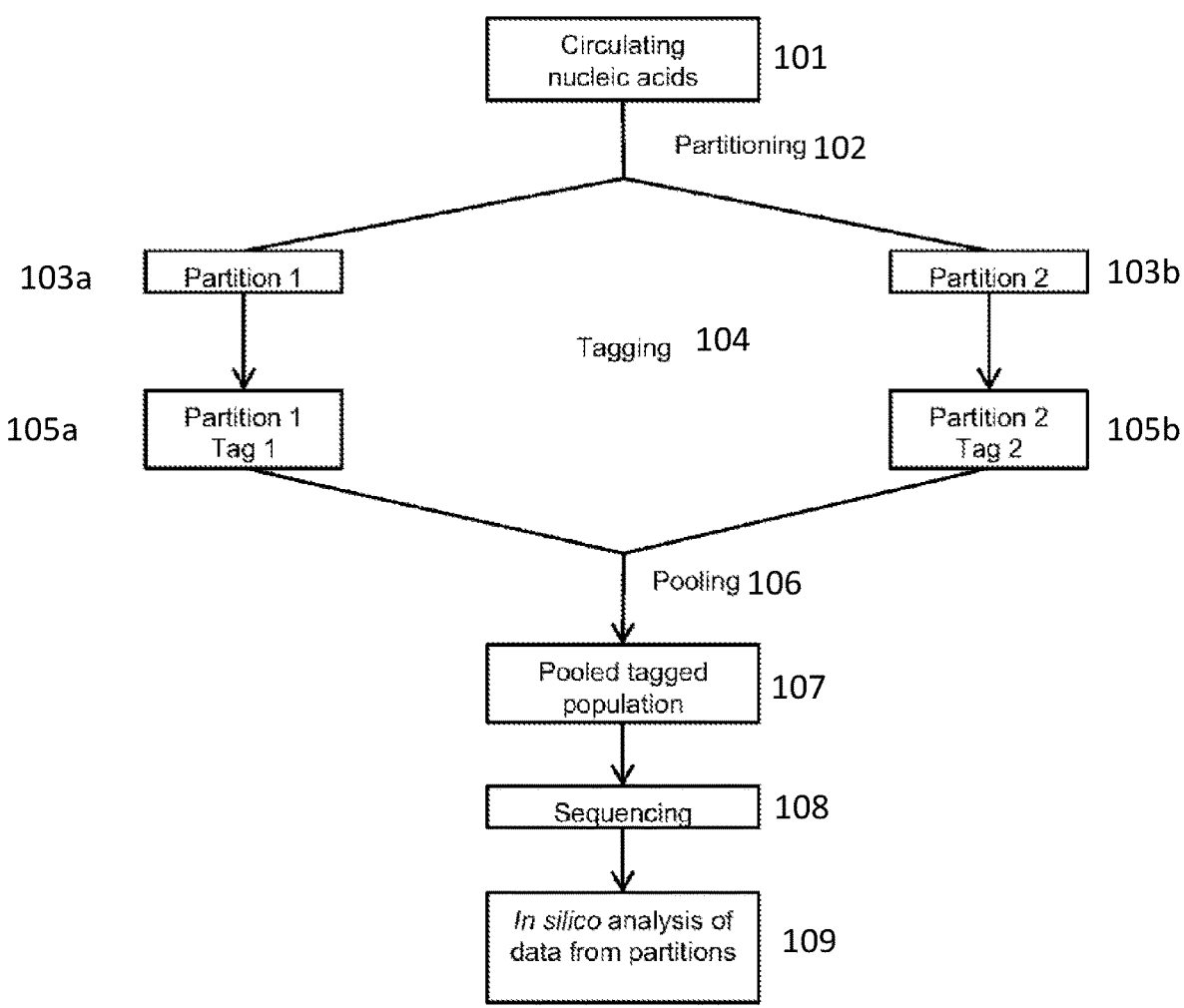
FIG. 1 shows an overview of partitioning methodology.

Reference will now be made in detail to certain embodiments of the invention. While the invention will be described in conjunction with such embodiments, it will be understood that they are not intended to limit the invention to those embodiments. On the contrary, the invention is intended to cover all alternatives, modifications, and equivalents, which may be included within the invention as defined by the appended claims.

Before describing the present teachings in detail, it is to be understood that the disclosure is not limited to specific compositions or process steps, as such may vary. It should be noted that, as used in this specification and the appended claims, the singular form "a", "an" and "the" include plural references unless the context clearly dictates otherwise. Thus, for example, reference to "a nucleic acid" includes a plurality of nucleic acids, reference to "a cell" includes a plurality of cells, and the like.

Numeric ranges are inclusive of the numbers defining the range. Measured and measurable values are understood to be approximate, taking into account significant digits and the error associated with the measurement. Also, the use of "comprise", "comprises". "comprising", "contain", "contains", "containing", "include", "includes", and "including" are not intended to be limiting. It is to be understood that both the foregoing general description and detailed description are exemplary and explanatory only and are not restrictive of the teachings.

Unless specifically noted in the above specification, embodiments in the specification that recite "comprising" various components are also contemplated as "consisting of" or "consisting essentially of" the recited components; embodiments in the specification that recite "consisting of" various components are also contemplated as "comprising" or "consisting essentially of" the recited components; and embodiments in the specification that recite "consisting essentially of" various components are also contemplated as "consisting of" or "comprising" the recited components (this interchangeability does not apply to the use of these terms in the claims).

The section headings used herein are for organizational purposes and are not to be construed as limiting the disclosed subject matter in any way. In the event that any document or other material incorporated by reference contradicts any explicit content of this specification, including definitions, this specification controls.

I. Definitions

"Cell-free DNA," "cfDNA molecules," or simply "cfDNA" include DNA molecules that occur in a subject in extracellular form (e.g., in blood, serum, plasma, or other bodily fluids such as lymph, cerebrospinal fluid, urine, or sputum) and includes DNA not contained within or otherwise bound to a cell. While the DNA originally existed in a cell or cells in a large complex biological organism, e.g., a mammal, the DNA has undergone release from the cell(s) into a fluid found in the organism. Typically, cfDNA may be obtained by obtaining a sample of the fluid without the need to perform an in vitro cell lysis step and also includes removal of cells present in the fluid (e.g., centrifugation of blood to remove cells).

The "capture yield" of a collection of probes for a given target region set refers to the amount (e.g., amount relative to another target region set or an absolute amount) of nucleic acid corresponding to the target region set that the collection captures under typical conditions. Exemplary typical capture conditions are an incubation of the sample nucleic acid and probes at 65° C. for 10-18 hours in a small reaction volume (about 20 μL) containing stringent hybridization buffer. The capture yield may be expressed in absolute terms or, for a plurality of collections of probes, relative terms. When capture yields for a plurality of sets of target regions are compared, they are normalized for the footprint size of the target region set (e.g., on a per-kilobase basis). Thus, for example, if the footprint sizes of first and second target regions are 50 kb and 500 kb, respectively (giving a normalization factor of 0.1), then the DNA corresponding to the first target region set is captured with a higher yield than DNA corresponding to the second target region set when the mass per volume concentration of the captured DNA corresponding to the first target region set is more than 0.1 times the mass per volume concentration of the captured DNA corresponding to the second target region set. As a further example, using the same footprint sizes, if the captured DNA corresponding to the first target region set has a mass per volume concentration of 0.2 times the mass per volume concentration of the captured DNA corresponding to the second target region set, then the DNA corresponding to the first target region set was captured with a two-fold greater capture yield than the DNA corresponding to the second target region set.

"Capturing" or "enriching" one or more target nucleic acids refers to preferentially isolating or separating the one or more target nucleic acids from non-target nucleic acids.

A "captured set" of nucleic acids refers to nucleic acids that have undergone capture.

A "target-region set" or "set of target regions" or "target regions" refers to a plurality of genomic loci or a plurality of genomic regions targeted for capture and/or targeted by a set of probes (e.g., through sequence complementarity).

"Corresponding to a target region set" means that a nucleic acid, such as cfDNA, originated from a locus in the target region set or specifically binds one or more probes for the target-region set.

"Specifically binds" in the context of an probe or other oligonucleotide and a target sequence means that under appropriate hybridization conditions, the oligonucleotide or probe hybridizes to its target sequence, or replicates thereof, to form a stable probe:target hybrid, while at the same time formation of stable probe:non-target hybrids is minimized. Thus, a probe hybridizes to a target sequence or replicate thereof to a sufficiently greater extent than to a non-target sequence, to enable capture or detection of the target sequence. Appropriate hybridization conditions are well-known in the art, may be predicted based on sequence composition, or can be determined by using routine testing methods (see, e.g., Sambrook et al., Molecular Cloning. A Laboratory Manual, 2nd ed. (Cold Spring Harbor Laboratory Press, Cold Spring Harbor, NY, 1989) at §§ 1.90-1.91, 7.37-7.57, 9.47-9.51 and 11.47-11.57, particularly §§ 9.50-9.51, 11.12-11.13, 11.45-11.47 and 11.55-11.57, incorporated by reference herein).

"Sequence-variable target region set" refers to a set of target regions that may exhibit changes in sequence such as nucleotide substitutions, insertions, deletions, or gene fusions or transpositions in neoplastic cells (e.g., tumor cells and cancer cells).

"Epigenetic target region set" refers to a set of target regions that may manifest non-sequence modifications in neoplastic cells (e.g., tumor cells and cancer cells) and non-tumor cells (e.g., immune cells, cells from tumor microenvironment). These modifications do not change the sequence of the DNA. Examples of non-sequence modifications changes include, but not limited to, changes in methylation (increases or decreases), nucleosome distribution, CTCF binding, transcription start sites, regulatory protein binding regions and any other proteins that may bind to the DNA. For present purposes, loci susceptible to neoplasia-, tumor-, or cancer-associated focal amplifications and/or gene fusions may also be included in an epigenetic target region set because detection of a change in copy number by sequencing or a fused sequence that mops to more than one locus in a reference genome tends to be more similar to detection of exemplary epigenetic changes discussed above than detection of nucleotide substitutions, insertions, or deletions, e.g., in that the focal amplifications and/or gene fusions an be detected at a relatively shallow depth of sequencing because their detection does not depend on the accuracy of base calls at one or a few individual positions. For example, the epigenetic target region set can comprise a set of target regions for analyzing the fragment length or fragment end point location distribution. The terms "epigenetic" and "epigenomic" are used interchangeably herein.

A circulating tumor DNA or ctDNA is a component of cfDNA that originated from a tumor cell or cancer cell. In some embodiments, cfDNA comprises DNA that originated from normal cells and DNA that originated from tumor cells (i.e., ctDNA). Tumor cells are neoplastic cells that originated from a tumor, regardless of whether they remain in the tumor or become separated from the tumor (as in the cases, e.g., of metastatic cancer cells and circulating tumor cells).

The term "hypermethylation" refers to an increased level or degree of methylation of nucleic acid molecule(s) relative to the other nucleic acid molecules within a population (e.g., sample) of nucleic acid molecules. In some embodiments, hypermethylated DNA can include DNA molecules comprising at least 1 methylated residue, at least 2 methylated residues, at least 3 methylated residues, at least 5 methylated residues, at least 10 methylated residues, at least 20 methylated residues, at least 25 methylated residues, or at least 30 methylated residues.

The term "hypomethylation" refers to a decreased level or degree of methylation of nucleic acid molecule(s) relative to the other nucleic acid molecules within a population (e.g., sample) of nucleic acid molecules. In some embodiments, hypomethylated DNA includes unmethylated DNA molecules. In some embodiments, hypomethylated DNA can include DNA molecules comprising 0 methylated residues, at most 1 methylated residue, at most 2 methylated residues, at most 3 methylated residues, at most 4 methylated residues, or at most 5 methylated residues.

The terms "or a combination thereof" and "or combinations thereof" as used herein refers to any and all permutations and combinations of the listed terms preceding the term. For example, "A, B. C. or combinations thereof" is intended to include at least one of: A, B, C, AB, AC, BC, or ABC, and if order is important in a particular context, also BA, CA, CB, ACB, CBA, BCA, BAC, or CAB. Continuing with this example, expressly included are combinations that contain repeats of one or more item or term, such as BB, AAA, AAB, BBC, AAABCCCC, CBBAAA, CABABB, and so forth. The skilled artisan will understand that typically there is no limit on the number of items or terms in any combination, unless otherwise apparent from the context.

"Or" is used in the inclusive sense, i.e., equivalent to "and/or," unless the context requires otherwise.

II. Exemplary Methods

Provided herein are methods of isolating cell-free DNA (cfDNA) and/or identifying the presence of DNA produced by a tumor (or neoplastic cells, or cancer cells).

In some embodiments, the methods comprise capturing cDNA obtained from a test subject for a plurality of sets of target regions. The target regions comprise epigenetic target regions, which may show differences in methylation levels and/or fragmentation patterns depending on whether they originated from a tumor or from healthy cells. The target regions also comprise sequence-variable target regions, which may show differences in sequence depending on whether they originated from a tumor or from healthy cells. The capturing step produces a captured set of cfDNA molecules, and the cfDNA molecules corresponding to the sequence-variable target region set are captured at a greater capture yield in the captured set of cfDNA molecules than cfDNA molecules corresponding to the epigenetic target region set.

In some embodiments, the methods comprise contacting cfDNA obtained from a test subject with a set of target-specific probes, wherein the set of target-specific probes is configured to capture cfDNA corresponding to the sequence-variable target region set at a greater capture yield than cfDNA corresponding to the epigenetic target region set.

It can be beneficial to capture cfDNA corresponding to the sequence-variable target region set at a greater capture yield than cfDNA corresponding to the epigenetic target region set because a greater depth of sequencing may be necessary to analyze the sequence-variable target regions with sufficient confidence or accuracy than may be necessary to analyze the
epigenetic target regions. The greater depth of sequencing
can result in more reads per DNA molecule and can be
facilitated by capturing more unique molecules per region.
The volume of data needed to determine fragmentation
patterns (e.g., to test for perturbation of transcription start
sites or CTCF binding sites) or fragment abundance (e.g., in
hypermethylated and hypomethylated partitions) is gener-
ally less than the volume of data needed to determine the
presence or absence of cancer-related sequence mutations.
Capturing the target region sets at different yields can
facilitate sequencing the target regions to different depths of
sequencing in the same sequencing run (e.g., using a pooled
mixture and/or in the same sequencing cell).

In various embodiments, the methods further comprise
sequencing the captured cfDNA, e.g., to different degrees of
sequencing depth for the epigenetic and sequence-variable
target region sets, consistent with the discussion above.

1. Capturing Step; Amplification; Adapters; Barcodes

In some embodiments, methods disclosed herein com-
prise a step of capturing one or more sets of target regions
of DNA, such as cfDNA. Capture may be performed using
any suitable approach known in the art.

In some embodiments, capturing comprises contacting the
DNA to be captured with a set of target-specific probes. The
set of target-specific probes may have any of the features
described herein for sets of target-specific probes, including
but not limited to in the embodiments set forth above and the
sections relating to probes below.

The capturing step may be performed using conditions
suitable for specific nucleic acid hybridization, which gen-
erally depend to some extent on features of the probes such
as length, base composition, etc. Those skilled in the art will
be familiar with appropriate conditions given general knowl-
edge in the art regarding nucleic acid hybridization. In some
embodiments, complexes of target-specific probes and DNA
are formed.

In some embodiments, complexes of target-specific
probes and DNA are separated from DNA not bound to
target-specific probes. For example, where target-specific
probes are bound covalently or noncovalently to a solid
support, a washing or aspiration step can be used to separate
unbound material. Alternatively, where the complexes have
chromatographic properties distinct from unbound material
(e.g., where the probes comprise a ligand that binds a
chromatographic resin), chromatography can be used.

As discussed in detail elsewhere herein, the set of target-
specific probes may comprise a plurality of sets such as
probes for a sequence-variable target region set and probes
for an epigenetic target region set. In some such embodi-
ments, the capturing step is performed with the probes for
the sequence-variable target region set and the probes for the
epigenetic target region set in the same vessel at the same
time, e.g., the probes for the sequence-variable and epigen-
etic target region sets are in the same composition. This
approach provides a relatively streamlined workflow. In
some embodiments, the concentration of the probes for the
sequence-variable target region set is greater that the con-
centration of the probes for the epigenetic target region set.

Alternatively, the capturing step is performed with the
sequence-variable target region probe set in a first vessel and
with the epigenetic target region probe set in a second vessel,
or the contacting step is performed with the sequence-
variable target region probe set at a first time and a first
vessel and the epigenetic target region probe set at a second
time before or after the first time. This approach allows for
preparation of separate first and second compositions comprising captured DNA corresponding to the sequence-vari-
able target region set and captured DNA corresponding to
the epigenetic target region set. The compositions can be
processed separately as desired (e.g., to fractionate based on
methylation as described elsewhere herein) and recombined
in appropriate proportions to provide material for further
processing and analysis such as sequencing.

In some embodiments, the DNA is amplified. In some
embodiments, amplification is performed before the captur-
ing step. In some embodiments, amplification is performed
after the capturing step. Methods for nonspecific amplifica-
tion of DNA are known in the art. See, e.g., Smallwood et
al., Nat. Methods 11: 817-820 (2014). For example, random
primers having adapter sequences on their 5' ends and
random bases on the 3' end can be used. There are usually
6 random bases but can be between 4 and 9 bases long. This
approach is amenable for low input/single cell amplification
and/or bisulfite sequencing.

In some embodiments, adapters are included in the DNA.
This may be done concurrently with an amplification pro-
cedure, e.g., by providing the adapters in a 5' portion of a
primer, e.g., as described above. Alternatively, adapters an
be added by other approaches, such as ligation.

In some embodiments, tags, which may be or include
barcodes, are included in the DNA. Tags an facilitate iden-
tification of the origin of a nucleic acid. For example,
barcodes an be used to allow the origin (e.g., subject)
whence the DNA came to be identified following pooling of
a plurality of samples for parallel sequencing. This may be
done concurrently with an amplification procedure, e.g., by
providing the barcodes in a 5' portion of a primer, e.g., as
described above. In some embodiments, adapters and tags/
barcodes are provided by the same primer or primer set. For
example, the barcode may be located 3' of the adapter and
5' of the target-hybridizing portion of the primer. Alterna-
tively, barcodes an be added by other approaches, such as
ligation, optionally together with adapters in the same liga-
tion substrate.

Additional details regarding amplification, tags, and bar-
codes are discussed in the "General Features of the Meth-
ods" section below, which can be combined to the extent
practicable with any of the foregoing embodiments and the
embodiments set forth in the introduction and summary
section.

2. Captured Set

In some embodiments, a captured set of DNA (e.g.,
cfDNA) is provided. With respect to the disclosed methods,
the captured set of DNA may be provided, e.g., following
capturing, and/or separating steps as described herein. The
captured set may comprise DNA corresponding to a
sequence-variable target region set and an epigenetic target
region set. In some embodiments the quantity of captured
sequence-variable target region DNA is greater than the
quantity of the captured epigenetic target region DNA, when
normalized for the difference in the size of the targeted
regions (footprint size).

Alternatively, first and second captured sets may be
provided, comprising, respectively, DNA corresponding to a
sequence-variable target region set and DNA corresponding
to an epigenetic target region set. The first and second
captured sets may be combined to provide a combined
captured set.

In a captured set comprising DNA corresponding to the
sequence-variable target region set and the epigenetic target
region set, including a combined captured set as discussed
above, the DNA corresponding to the sequence-variable
target region set may be present at a greater concentration than the DNA corresponding to the epigenetic target region set, e.g., a 1.1 to 1.2-fold greater concentration, a 1.2- to 1.4-fold greater concentration, a 1.4- to 1.6-fold greater concentration, a 1.6- to 1.8-fold greater concentration, a 1.8- to 2.0-fold greater concentration, a 2.0- to 2.2-fold greater concentration, a 2.2- to 2.4-fold greater concentration a 2.4- to 2.6-fold greater concentration, a 2.6- to 2.8-fold greater concentration, a 2.8- to 3.0-fold greater concentration, a 3.0- to 3.5-fold greater concentration, a 3.5- to 4.0, a 4.0- to 4.5-fold greater concentration, a 4.5- to 5.0-fold greater concentration, a 5.0- to 5.5-fold greater concentration, a 5.5- to 6.0-fold greater concentration, a 6.0- to 6.5-fold greater concentration, a 6.5- to 7.0-fold greater, a 7.0- to 7.5-fold greater concentration, a 7.5- to 8.0-fold greater concentration, an 8.0- to 8.5-fold greater concentration, an 8.5- to 9.0-fold greater concentration, a 9.0- to 9.5-fold greater concentration, 9.5- to 10.0-fold greater concentration, a 10- to 11-fold greater concentration, an 11- to 12-fold greater concentration a 12- to 13-fold greater concentration, a 13- to 14-fold greater concentration, a 14- to 15-fold greater concentration, a 15- to 16-fold greater concentration, a 16- to 17-fold greater concentration, a 17- to 18-fold greater concentration, an 18- to 19-fold greater concentration, or a 19- to 20-fold greater concentration. The degree of difference in concentrations accounts for normalization for the footprint sizes of the target regions, as discussed in the definition section.

a. Epigenetic Target Region Set

The epigenetic target region set may comprise one or more types of target regions likely to differentiate DNA from neoplastic (e.g., tumor or cancer) cells and from healthy cells, e.g., non-neoplastic circulating cells. Exemplary types of such regions are discussed in detail herein. In some embodiments, methods according to the disclosure comprise determining whether cfDNA molecules corresponding to the epigenetic target region set comprise or indicate cancer-associated epigenetic modifications (e.g., hypermethylation in one or more hypermethylation variable target regions; one or more perturbations of CTCF binding; and/or one or more perturbations of transcription start sites) and/or copy number variations (e.g., focal amplifications). The epigenetic target region set may also comprise one or more control regions, e.g., as described herein.

In some embodiments, the epigenetic target region set has a footprint of at least 100 kb, e.g., at least 200 kb, at least 300 kb, or at least 400 kb. In some embodiments, the epigenetic target region set has a footprint in the range of 100-1000 kb, e.g., 100-200 kb, 200-300 kb, 300-400 kb, 400-500 kb, 500-600 kb, 600-700 kb, 700-800 kb, 800-900 kb, and 900-1,000 kb.

i. Hypermethylation Variable Target Region

In some embodiments, the epigenetic target region set comprises one or more hypermethylation variable target regions. In general, hypermethylation variable target regions refer to regions where an increase in the level of observed methylation indicates an increased likelihood that a sample (e.g., of cfDNA) contains DNA produced by neoplastic cells, such as tumor or cancer cells. For example, hypermethylation of promoters of tumor suppressor genes has been observed repeatedly. See, e.g., Kang et al., Genome Biol. 18:53 (2017) and references cited therein.

An extensive discussion of methylation variable target regions in colorectal cancer is provided in Lam et al., Biochim Biophys Acta. 1866:106-20 (2016). These include VIM, SEPT9, ITGA4, OSM4, GATA4 and NDRG4. An exemplary set of hypermethylation variable target regions comprising the genes or portions thereof based on the colorectal cancer (CRC) studies is provided in Table 1. Many of these genes likely have relevance to cancers beyond colorectal cancer; for example, TP53 is widely recognized as a critically important tumor suppressor and hypermethylation-based inactivation of this gene may be a common oncogenic mechanism.

TABLE 1

| Exemplary hypermethylation target regions (genes or portions thereof) based on CRC studies. | | |
| --- | --- | --- |
| Gene Name | Additional Gene Name | Chromosome |
| VIM | | chr10 |
| SEPT9 | | chr17 |
| CYCD2 | CCND2 | chr12 |
| TFPI2 | | chr7 |
| GATA4 | | chr8 |
| RARB2 | RARB | chr3 |
| p16INK4a | CDKN2A | chr9 |
| MGMT | MGMT | chr10 |
| APC | | chr5 |
| NDRG4 | | chr16 |
| HLTF | | chr3 |
| HPP1 | TMEFF2 | chr2 |
| hMLH1 | MLH1 | chr3 |
| RASSF1A | RASSF1 | chr3 |
| CDH13 | | chr16 |
| IGFBP3 | | chr7 |
| ITGA4 | | chr2 |

In some embodiments, the hypermethylation variable target regions comprise a plurality of genes or portions thereof listed in Table 1, e.g., at least 10%, 20%, 30%, 40%, 50%, 60%, 70%, 80%, 90%, or 100% of the genes or portions thereof listed in Table 1. For example, for each locus included as a target region, there may be one or more probes with a hybridization site that binds between the transcription start site and the stop codon (the last stop codon for genes that are alternatively spliced) of the gene. In some embodiments, the one or more probes bind within 300 bp upstream and/or downstream of the genes or portions thereof listed in Table 1, e.g., within 200 or 100 bp.

Methylation variable target regions in various types of lung cancer are discussed in detail, e.g., in Ooki et al., Clin. Cancer Res. 23:7141-52 (2017); Belinksy, Annu. Rev. Physiol. 77:453-74 (2015); Hulbert et al., Clin. Cancer Res. 23:1998-2005 (2017); Shi et al., BMC Genomics 18:901 (2017); Schneider et al., BMC Cancer. 11:102 (2011); Lissa et al., Transl Lung Cancer Res 5(5):492-504 (2016); Skvortsova et al., Br. J. Cancer. 94(10):1492-1495 (2006); Kim et al., Cancer Res. 61:3419-3424 (2001); Furonaka et al., Pathology International 55:303-309 (2005); Gomes et al., Rev. Port. Pneumol. 20:20-30 (2014); Kim et al., Oncogene. 20:1765-70 (2001); Hopkins-Donaldson et al., Cell Death Differ. 10:356-64 (2003); Kikuchi et al., Clin. Cancer Res. 11:2954-61 (2005); Heller et al., Oncogene 25:959-968 (2006); Licchesi et al., Carcinogenesis. 29:895-904 (2008); Guo et al., Clin. Cancer Res. 10:7917-24 (2004); Palmisano et al., Cancer Res. 63:4620-4625 (2003); and Toyooka at al., Cancer Res. 61:4556-4560, (2001).

An exemplary set of hypermethylation variable target regions comprising genes or portions thereof based on the lung cancer studies is provided in Table 2. Many of these genes likely have relevance to cancers beyond lung cancer; for example, Casp8 (Caspase 8) is a key enzyme in programmed cell death and hypermethylation-based inactivation of this gene may be a common oncogenic mechanism not limited to lung cancer. Additionally, a number of genes appear in both Tables 1 and 2, indicating generality.

TABLE 2

| Exemplary hypermethylation target regions (genes or portions thereof) based on lung cancer studies | |
| --- | --- |
| Gene Name | Chromosome |
| MARCH11 | chr5 |
| TAC1 | chr7 |
| TCF21 | chr6 |
| SHOX2 | chr3 |
| p16 | chr3 |
| Casp8 | chr2 |
| CDH13 | chr16 |
| MGMT | chr10 |
| MLH1 | chr3 |
| MSH2 | chr2 |
| TSLC1 | chr11 |
| APC | chr5 |
| DKK1 | chr10 |
| DKK3 | chr11 |
| LKB1 | chr11 |
| WIF1 | chr12 |
| RUNX3 | chr1 |
| GATA4 | chr8 |
| GATA5 | chr20 |
| PAX5 | chr9 |
| E-Cadherin | chr16 |
| H-Cadherin | chr16 |

Any of the foregoing embodiments concerning target regions identified in Table 2 may be combined with any of the embodiments described above concerning target regions identified in Table 1. In some embodiments, the hypermethylation variable target regions comprise a plurality of genes or portions thereof listed in Table 1 or Table 2, e.g., at least 10%, 20%, 30%, 40%. 50%, 60%. 70%, 80%. 90%, or 100% of the genes or portions thereof listed in Table 1 or Table 2.

Additional hypermethylation target regions may be obtained, e.g., from the Cancer Genome Atlas. Kang et al., Genome Biology 18:53 (2017), describe construction of a probabilistic method called Cancer Locator using hyperm-ethylation target regions from breast, colon, kidney, liver, and lung. In some embodiments, the hypermethylation target regions can be specific to one or more types of cancer. Accordingly, in some embodiments, the hypermethylation target regions include one, two, three, four, or five subsets of hypermethylation target regions that collectively show hypermethylation in one, two, three, four, or five of breast, colon, kidney, liver, and lung cancers.

ii. Hypomethylation Variable Target Regions

Global hypomethylation is a commonly observed phe-nomenon in various cancers. See, e.g., Hon et al., Genome Res. 22:246-258 (2012) (breast cancer); Ehrlich, Epigenom-ics 1:239-259 (2009) (review article noting observations of hypomethylation in colon, ovarian, prostate, leukemia, hepatocellular, and cervical cancers). For example, regions such as repeated elements, e.g., LINE1 elements, Alu ele-ments, centromeric tandem repeats, pericentromeric tandem repeats, and satellite DNA, and intergenic regions that are ordinarily methylated in healthy cells may show reduced methylation in tumor cells. Accordingly, in some embodi-ments, the epigenetic target region set includes hypometh-ylation variable target regions, where a decrease in the level of observed methylation indicates an increased likelihood that a sample (e.g., of cfDNA) contains DNA produced by neoplastic cells, such as tumor or cancer cells.

In some embodiments, hypomethylation variable target regions include repeated elements and/or intergenic regions.

In some embodiments, repeated elements include one, two, three, four, or five of LINE1 elements, Alu elements, cen-tromeric tandem repeats, pericentromeric tandem repeats, and/or satellite DNA.

Exemplary specific genomic regions that show cancer-associated hypomethylation include nucleotides 8403565-8953708 and 151104701-151106035 of human chromosome 1, e.g., according to the hg19 or hg38 human genome construct. In some embodiments, the hypomethylation vari-able target regions overlap or comprise one or both of these regions.

iii. CTCF Binding Regions

CTCF is a DNA-binding protein that contributes to chro-matin organization and often colocalizes with cohesin. Per-turbation of CTCF binding sites has been reported in a variety of different cancers. See, e.g., Katainen et al., Nature Genetics, doi:10.1038/ng.3335, published online 8 Jun. 2015; Guo et al., Nat. Commun. 9:1520 (2018). CTCF binding results in recognizable patterns in cfDNA that can be detected by sequencing, e.g., through fragment length analysis. For example, details regarding sequencing-based fragment length analysis are provided in Snyder et al., Cell 164:57-68 (2016); WO 2018/009723; and US20170211143A1, each of which are incorporated herein by reference.

Thus, perturbations of CTCF binding result in variation in the fragmentation patterns of cfDNA. As such, CTCF bind-ing sites represent a type of fragmentation variable target regions.

There are many known CTCF binding sites. See, e.g., the CTCFBSDB (CTCF Binding Site Database), available on the Internet at insulatorb.uthsc.edu/; Cuddepsh et al., Genome Res. 19:24-32 (2009); Martin et al., Nat. Struct. Mol. Biol. 18:708-14 (2011); Rhee et al., Cell. 147:1408-19 (2011), each of which are incorporated by reference. Exem-plary CTCF binding sites are at nucleotides 56014955-56016161 on chromosome 8 and nucleotides 95359169-95360473 on chromosome 13, e.g., according to the hg19 or hg38 human genome construct.

Accordingly, in some embodiments, the epigenetic target region set includes CTCF binding regions. In some embodi-ments, the CTCF binding regions comprise at least 10, 20, 50, 100, 200, or 500 CTCF binding regions, or 10-20, 20-50, 50-100, 100-200, 200-500, or 500-1000 CTCF binding regions, e.g., such as CTCF binding regions described above or in one or more of CTCFBSDB or the Cuddpah et al., Martin et al., or Rhee et al. articles cited above.

In some embodiments, at least some of the CTCF sites can be methylated or unmethylated, wherein the methylation state is correlated with the whether or not the cell is a cancer cell. In some embodiments, the epigenetic target region set comprises at least 100 bp, at least 200 bp, at least 300 bp, at least 400 bp, at least 500 bp, at least 750 bp, at least 1000 bp upstream and/or downstream regions of the CTCF bind-ing sites.

iv. Transcription Start Sites

Transcription start sites may also show perturbations in neoplastic cells. For example, nucleosome organization at various transcription start sites in healthy cells of the hema-topoietic lineage—which contributes substantially to cfDNA in healthy individuals—may differ from nucleosome organization at those transcription start sites in neoplastic cells. This results in different cfDNA patterns that can be detected by sequencing, for example, as discussed generally in Snyder et al., Cell 164:57-68 (2016); WO 2018/009723; and US20170211143A1.

Thus, perturbations of transcription start sites also result in variation in the fragmentation patterns of cfDNA. As such, transcription start sites also represent a type of fragmentation variable target regions.

Human transcriptional start sites are available from DBTSS (DataBase of Human Transcription Start Sites), available on the Internet at dbtss.hgc.jp and described in Yamashita et al., Nucleic Acids Res. 34(Database issue): D86-D89 (2006), which is incorporated herein by reference.

Accordingly, in some embodiments, the epigenetic target region set includes transcriptional start sites. In some embodiments, the transcriptional start sites comprise at least 10, 20, 50, 100, 200, or 500 transcriptional start sites, or 10-20, 20-50, 50-100, 100-200, 200-500, or 500-1000 transcriptional start sites, e.g., such as transcriptional start sites listed in DBTSS. In some embodiments, at least some of the transcription start sites can be methylated or unmethylated, wherein the methylation state is correlated with the whether or not the cell is a cancer cell. In some embodiments, the epigenetic target region set comprises at least 100 bp, at least 200 bp, at least 300 bp, at least 400 bp, at least 500 bp, at least 750 bp, at least 1000 bp upstream and/or downstream regions of the transcription start sites.

v. Copy Number Variations; Focal Amplifications

Although copy number variations such as focal amplifications are somatic mutations, they can be detected by sequencing based on read frequency in a manner analogous to approaches for detecting certain epigenetic changes such as changes in methylation. As such, regions that may show copy number variations such as focal amplifications in cancer can be included in the epigenetic target region set and may comprise one or more of AR, BRAF, CCND1, CCND2, CCNE1, CDK4, CDK6, EGFR, ERBB2, FGFR1, FGFR2, KIT, KRAS, MET, MYC, PDGFRA, PIK3CA, and RAF1. For example, in some embodiments, the epigenetic target region set comprises at least 2, 3, 4, 5, 6, 7, 8, 9, 10, 11, 12, 13, 14, 15, 16, 17, or 18 of the foregoing targets.

vi. Methylation Control Regions

It can be useful to include control regions to facilitate data validation. In some embodiments, the epigenetic target region set includes control regions that are expected to be methylated or unmethylated in essentially all samples, regardless of whether the DNA is derived from a cancer cell or a normal cell. In some embodiments, the epigenetic target region set includes control hypomethylated regions that are expected to be hypomethylated in essentially all samples. In some embodiments, the epigenetic target region set includes control hypermethylated regions that are expected to be hypermethylated in essentially all samples.

b. Sequence-Variable Target Region Set

In some embodiments, the sequence-variable target region set comprises a plurality of regions known to undergo somatic mutations in cancer (referred to herein as cancer-associated mutations). Accordingly, methods may comprise determining whether cfDNA molecules corresponding to the sequence-variable target region set comprise cancer-associated mutations.

In some embodiments, the sequence-variable target region set targets a plurality of different genes or genomic regions ("panel") selected such that a determined proportion of subjects having a cancer exhibits a genetic variant or tumor marker in one or more different genes or genomic regions in the panel. The panel may be selected to limit a region for sequencing to a fixed number of base pairs. The panel may be selected to sequence a desired amount of DNA, e.g., by adjusting the affinity and/or amount of the probes as described elsewhere herein. The panel may be further selected to achieve a desired sequence read depth. The panel may be selected to achieve a desired sequence read depth or sequence read coverage for an amount of sequenced base pairs. The panel may be selected to achieve a theoretical sensitivity, a theoretical specificity, and/or a theoretical accuracy for detecting one or more genetic variants in a sample.

Probes for detecting the panel of regions can include those for detecting genomic regions of interest (hotspot regions) as well as nucleosome-aware probes (e.g., KRAS codons 12 and 13) and may be designed to optimize capture based on analysis of cfDNA coverage and fragment size variation impacted by nucleosome binding patterns and GC sequence composition. Regions used herein can also include non-hotspot regions optimized based on nucleosome positions and GC models.

Examples of listings of genomic locations of interest may be found in Table 3 and Table 4. In some embodiments, a sequence-variable target region set used in the methods of the present disclosure comprises at least a portion of at least 5, at least 10, at least 15, at least 20, at least 25, at least 30, at least 35, at least 40, at least 45, at least 50, at least 55, at least 60, at least 65, or 70 of the genes of Table 3. In some embodiments, a sequence-variable target region set used in the methods of the present disclosure comprises at least 5, at least 10, at least 15, at least 20, at least 25, at least 30, at least 35, at least 40, at least 45, at least 50, at least 55, at least 60, at least 65, or 70 of the SNVs of Table 3. In some embodiments, a sequence-variable target region set used in the methods of the present disclosure comprises at least 1, at least 2, at least 3, at least 4, at least 5, or 6 of the fusions of Table 3. In some embodiments, a sequence-variable target region set used in the methods of the present disclosure comprise at least a portion of at least 1, at least 2, or 3 of the indels of Table 3. In some embodiments, a sequence-variable target region set used in the methods of the present disclosure comprises at least a portion of at least 5, at least 10, at least 15, at least 20, at least 25, at least 30, at least 35, at least 40, at least 45, at least 50, at least 55, at least 60, at least 65, at least 70, or 73 of the genes of Table 4. In some embodiments, a sequence-variable target region set used in the methods of the present disclosure comprises at least 5, at least 10, at least 15, at least 20, at least 25, at least 30, at least 35, at least 40, at least 45, at least 50, at least 55, at least 60, at least 65, at least 70, or 73 of the SNVs of Table 4. In some embodiments, a sequence-variable target region set used in the methods of the present disclosure comprises at least 1, at least 2, at least 3, at least 4, at least 5, or 6 of the fusions of Table 4. In some embodiments, a sequence-variable target region set used in the methods of the present disclosure comprises at least a portion of at least 1, at least 2, at least 3, at least 4, at least 5, at least 6, at least 7, at least 8, at least 9, at least 10, at least 11, at least 12, at least 13, at least 14, at least 15, at least 16, at least 17, or 18 of the indels of Table 4. Each of these genomic locations of interest may be identified as a backbone region or hot-spot region for a given panel. An example of a listing of hot-spot genomic locations of interest may be found in Table 5. The coordinates in Table 5 are based on the hg19 assembly of the human genome, but one skilled in the art will be familiar with other assemblies and can identify coordinate sets corresponding to the indicated exons, introns, codons, etc. in an assembly of their choice. In some embodiments, a sequence-variable target region set used in the methods of the present disclosure comprises at least a portion of at least 1, at least 2, at least 3, at least 4, at least 5, at least 6, at least 7, at least 8 at least 9, at least 10, at least 11, at least 12, at least 13, at least 14, at least 15, at least 16, at least 17, at least 18, at least 19, or at least 20 of the genes of Table 5. Each hot-spot genomic region is listed with several characteristics, including the associated gene, chromosome on which it resides, the start and stop position of the genome representing the gene's locus, the length of the gene's locus in base pairs, the exons covered by the gene, and the critical feature (e.g., type of mutation) that a given genomic region of interest may seek to capture.

TABLE 3

| Point Mutations (SNVs) and Indels | | | | | | Fusions |
|---|---|---|---|---|---|---|
| AKT1 | ALK | APC | AR | ARAF | ARID1A | ALK |
| ATM | BRAF | BRCA1 | BRCA2 | CCND1 | CCND2 | FGFR2 |
| CCNE1 | CDH1 | CDK4 | CDK6 | CDKN2A | CDKN2B | FGFR3 |
| CTNNB1 | EGFR | ERBB2 | ESR1 | EZH2 | FBXW7 | NTRK1 |
| FGFR1 | FGFR2 | FGFR3 | GATA3 | GNA11 | GNAQ | RET |
| GNAS | HNF1A | HRAS | IDH1 | IDH2 | JAK2 | ROS1 |
| JAK3 | KIT | KRAS | MAP2K1 | MAP2K2 | MET | |
| MLH1 | MPL | MYC | NF1 | NFE2L2 | NOTCH1 | |
| NPM1 | NRAS | NTRK1 | PDGFRA | PIK3CA | PTEN | |
| PTPN11 | RAF1 | RB1 | RET | RHEB | RHOA | |

TABLE 3-continued

| Point Mutations (SNVs) and Indels | | | | | Fusions |
|---|---|---|---|---|---|
| RIT1 | ROS1 | SMAD4 | SMO | SRC | STK11 |
| TERT | TP53 | TSC1 | VHL | | |

TABLE 4

| Point Mutations (SNVs) and Indels | | | | | | Fusions |
|---|---|---|---|---|---|---|
| AKT1 | ALK | APC | AR | ARAF | ARID1A | ALK |
| ATM | BRAF | BRCA1 | BRCA2 | CCND1 | CCND2 | FGFR2 |
| CCNE1 | CDH1 | CDK4 | CDK6 | CDKN2A | DDR2 | FGFR3 |
| CTNNB1 | EGFR | ERBB2 | ESR1 | EZH2 | FBXW7 | NTRK1 |
| FGFR1 | FGFR2 | FGFR3 | GATA3 | GNA11 | GNAQ | RET |
| GNAS | HNF1A | HRAS | IDH1 | IDH2 | JAK2 | ROS1 |
| JAK3 | KIT | KRAS | MAP2K1 | MAP2K2 | MET | |
| MLH1 | MPL | MYC | NF1 | NFE2L2 | NOTCH1 | |
| NPM1 | NRAS | NTRK1 | PDGFRA | PIK3CA | PTEN | |
| PTPN11 | RAF1 | RB1 | RET | RHEB | RHOA | |
| RIT1 | ROS1 | SMAD4 | SMO | MAPK1 | STK11 | |
| TERT | TP53 | TSC1 | VHL | MAPK3 | MTOR | |
| NTRK3 | | | | | | |

TABLE 5

| Gene | Chromosome | Start Position | Stop Position | Length (bp) | Exons/ Introns Covered | Feature |
|---|---|---|---|---|---|---|
| ALK | chr2 | 29446405 | 29446655 | 250 | intron 19 | Fusion |
| ALK | chr2 | 29446062 | 29446197 | 135 | intron 20 | Fusion |
| ALK | chr2 | 29446198 | 29446404 | 206 | exon 20 | Fusion |
| ALK | chr2 | 29447353 | 29447473 | 120 | intron 19 | Fusion |
| ALK | chr2 | 29447614 | 29448316 | 702 | intron 19 | Fusion |
| ALK | chr2 | 29448317 | 29448441 | 124 | exon 19 | Fusion |
| ALK | chr2 | 29449366 | 29449777 | 411 | intron 18 | Fusion |
| ALK | chr2 | 29449778 | 29449950 | 172 | exon 18 | Fusion |
| BRAF | chr7 | 140453064 | 140453203 | 139 | exon 15 | BRAF V600 |
| CTNNB1 | chr3 | 41266007 | 41266254 | 247 | exon 3 | S37 |
| EGFR | chr7 | 55240528 | 55240827 | 299 | exons 18 and 19 | G719 and deletions |
| EGFR | chr7 | 55241603 | 55241746 | 143 | exon 20 | Insertions/T790M |
| EGFR | chr7 | 55242404 | 55242523 | 119 | exon 21 | L858R |
| ERBB2 | chr17 | 37880952 | 37881174 | 222 | exon 20 | Insertions |
| ESR1 | chr6 | 152419857 | 152420111 | 254 | exon 10 | V534, P535, L536, Y537, D538 |
| FGFR2 | chr10 | 123279482 | 123279693 | 211 | exon 6 | S252 |
| GATA3 | chr10 | 8111426 | 8111571 | 145 | exon 5 | SS/Indels |
| GATA3 | chr10 | 8115692 | 8116002 | 310 | exon 6 | SS/Indels |
| GNAS | chr20 | 57484395 | 57484488 | 93 | exon 8 | R844 |
| IDH1 | chr2 | 209113083 | 209113394 | 311 | exon 4 | R132 |
| IDH2 | chr15 | 90631809 | 90631989 | 180 | exon 4 | R140, R172 |
| KIT | chr4 | 55524171 | 55524258 | 87 | exon 1 | |
| KIT | chr4 | 55561667 | 55561957 | 290 | exon 2 | |
| KIT | chr4 | 55564439 | 55564741 | 302 | exon 3 | |
| KIT | chr4 | 55565785 | 55565942 | 157 | exon 4 | |
| KIT | chr4 | 55569879 | 55570068 | 189 | exon 5 | |
| KIT | chr4 | 55573253 | 55573463 | 210 | exon 6 | |
| KIT | chr4 | 55575579 | 55575719 | 140 | exon 7 | |
| KIT | chr4 | 55589739 | 55589874 | 135 | exon 8 | |
| KIT | chr4 | 55592012 | 55592226 | 214 | exon 9 | |
| KIT | chr4 | 55593373 | 55593718 | 345 | exons 10 and 11 | 557, 559, 560, 576 |
| KIT | chr4 | 55593978 | 55594297 | 319 | exons 12 and 13 | V654 |
| KIT | chr4 | 55595490 | 55595661 | 171 | exon 14 | T670, S709 |
| KIT | chr4 | 55597483 | 55597595 | 112 | exon 15 | D716 |
| KIT | chr4 | 55598026 | 55598174 | 148 | exon 16 | L783 |
| KIT | chr4 | 55599225 | 55599368 | 143 | exon 17 | C809, R815, D816, L818, D820, S821F, N822, Y823 |
| KIT | chr4 | 55602653 | 55602785 | 132 | exon 18 | A829P |
| KIT | chr4 | 55602876 | 55602996 | 120 | exon 19 | |
| KIT | chr4 | 55603330 | 55603456 | 126 | exon 20 | |
| KIT | chr4 | 55604584 | 55604733 | 149 | exon 21 | |

TABLE 5-continued

| Gene | Chromosome | Start Position | Stop Position | Length (bp) | Exons/ Introns Covered | Feature |
|------|-----------|----------------|---------------|-------------|------------------------|---------|
| KRAS | chr12 | 25378537 | 25378717 | 180 | exon 4 | A146 |
| KRAS | chr12 | 25380157 | 25380356 | 199 | exon 3 | Q61 |
| KRAS | chr12 | 25398197 | 25398328 | 131 | exon 2 | G12/G13 |
| MET | chr7 | 116411535 | 116412255 | 720 | exon 13, exon 14, intron 13, intron 14 | MET exon 14 SS |
| NRAS | chr1 | 115256410 | 115256609 | 199 | exon 3 | Q61 |
| NRAS | chr1 | 115258660 | 115258791 | 131 | exon 2 | G12/G13 |
| PIK3CA | chr3 | 178935987 | 178936132 | 145 | exon 10 | E545K |
| PIK3CA | chr3 | 178951871 | 178952162 | 291 | exon 21 | H1047R |
| PTEN | chr10 | 89692759 | 89693018 | 259 | exon 5 | R130 |
| SMAD4 | chr18 | 48604616 | 48604849 | 233 | exon 12 | D537 |
| TERT | chr5 | 1294841 | 1295512 | 671 | promoter | chr5:1295228 |
| TP53 | chr17 | 7573916 | 7574043 | 127 | exon 11 | Q331, R337, R342 |
| TP53 | chr17 | 7577008 | 7577165 | 157 | exon 8 | R273 |
| TP53 | chr17 | 7577488 | 7577618 | 130 | exon 7 | R248 |
| TP53 | chr17 | 7578127 | 7578299 | 172 | exon 6 | R213/Y220 |
| TP53 | chr17 | 7578360 | 7578564 | 204 | exon 5 | R175/Deletions |
| TP53 | chr17 | 7579301 | 7579600 | 299 | exon 4 | |
| | | | | 12574 (total target region) 16330 (total probe coverage) | | |

Additionally, or alternatively, suitable target region sets are available from the literature. For example, Gale et al., PLoS One 13: e0194630 (2018), which is incorporated herein by reference, describes a panel of 35 cancer-related gene targets that can be used as part or all of a sequence-variable target region set. These 35 targets are AKT1, ALK, BRAF, CCND1, CDK2A, CTNNB1, EGFR, ERBB2, ESR1, FGFR1, FGFR2, FGFR3, FOXL2, GATA3, GNA11, GNAQ, GNAS, HRAS, IDH1, IDH2, KIT, KRAS, MED12, MET, MYC, NFE2L2, NRAS, PDGFRA, PDK3CA, PPP2R1A, PTEN, RET, STK11, TP53, and U2AF1.

In some embodiments, the sequence-variable target region set comprises target regions from at least 10, 20, 30, or 35 cancer-related genes, such as the cancer-related genes listed above.

3. Partitioning; Analysis of Epigenetic Characteristics

In certain embodiments described herein, a population of different forms of nucleic acids (e.g., hypermethylated and hypomethylated DNA in a sample, such as a captured set of cfDNA as described herein) can be physically partitioned based on one or more characteristics of the nucleic acids prior to analysis, e.g., sequencing, or tagging and sequencing. This approach can be used to determine, for example, whether hypermethylation variable epigenetic target regions show hypermethylation characteristic of tumor cells or hypomethylation variable epigenetic target regions show hypomethylation characteristic of tumor cells. Additionally, by partitioning a heterogeneous nucleic acid population, one may increase rare signals. e.g., by enriching rare nucleic acid molecules that are more prevalent in one fraction (or partition) of the population. For example, a genetic variation present in hyper-methylated DNA but less (or not) in hypomethylated DNA can be more easily detected by partitioning a sample into hyper-methylated and hypo-methylated nucleic acid molecules. By analyzing multiple fractions of a sample, a multi-dimensional analysis of a single locus of a genome or species of nucleic acid can be performed and hence, greater sensitivity can be achieved.

In some instances, a heterogeneous nucleic acid sample is partitioned into two or more partitions (e.g., at least 3, 4, 5, 6 or 7 partitions). In some embodiments, each partition is differentially tagged. Tagged partitions can then be pooled together for collective sample prep and/or sequencing. The partitioning-tagging-pooling steps can occur more than once, with each round of partitioning occurring based on a different characteristics (examples provided herein) and tagged using differential tap that are distinguished from other partitions and partitioning means.

Examples of characteristics that can be used for partitioning include sequence length, methylation level, nucleosome binding, sequence mismatch, immunoprecipitation, and/or proteins that bind to DNA. Resulting partitions can include one or more of the following nucleic acid forms: single-stranded DNA (ssDNA), double-stranded DNA (dsDNA), shorter DNA fragments and longer DNA fragments. In some embodiments, a heterogeneous population of nucleic acids is partitioned into nucleic acids with one or more epigenetic modifications and without the one or more epigenetic modifications. Examples of epigenetic modifications include presence or absence of methylation; level of methylation; type of methylation (e.g., 5-methylcytosine versus other types of methylation, such as adenine methylation and/or cytosine hydroxymethylation); and association and level of association with one or more proteins, such as histones. Alternatively, or additionally, a heterogeneous population of nucleic acids can be partitioned into nucleic acid molecules associated with nucleosomes and nucleic acid molecules devoid of nucleosomes. Alternatively, or additionally, a heterogeneous population of nucleic acids may be partitioned into single-stranded DNA (ssDNA) and double-stranded DNA (dsDNA). Alternatively, or additionally, a heterogeneous population of nucleic acids may be partitioned based on nucleic acid length (e.g., molecules of up to 160 bp and molecules having a length of greater than 160 bp).

In some instances, each partition (representative of a different nucleic acid form) is differentially labelled, and the partitions are pooled together prior to sequencing. In other instances, the different forms are separately sequenced.

FIG. 1 illustrates one embodiment of the disclosure. A population of different nucleic acids (101) is partitioned (102) into two or more different partitions (103 a, b). Each partition (103 a, b) is representative of a different nucleic acid form. Each partition is distinctly tagged (104). The tagged nucleic acids are pooled together (107) prior to sequencing (108). Reads are analyzed, in silico. Tags are used to sort reads from different partitions. Analysis to detect genetic variants can be performed on a partition-by-partition level, as well as whole nucleic acid population level. For example, analysis can include in silico analysis to determine genetic variants, such as CNV, SNV, indel, fusion in nucleic acids in each partition. In some instances, in silico analysis can include determining chromatin structure. For example, coverage of sequence reads can be used to determine nucleosome positioning in chromatin. Higher coverage can correlate with higher nucleosome occupancy in genomic region while lower coverage can correlate with lower nucleosome occupancy or nucleosome depleted region (NDR).

Samples can include nucleic acids varying in modifications including post-replication modifications to nucleotides and binding usually noncovalently, to one or more proteins.

In an embodiment, the population of nucleic acids is one obtained from a serum, plasma or blood sample from a subject suspected of having neoplasia, a tumor, or cancer or previously diagnosed with neoplasia, a tumor, or cancer. The population of nucleic acids includes nucleic acids having varying levels of methylation. Methylation cam occur from any one or more post-replication or transcriptional modifications. Post-replication modifications include modifications of the nucleotide cytosine, particularly at the 5-position of the nucleobase, e.g., 5-methylcytosine, 5-hydroxymethylcytosine, 5-formylcytosine and 5-carboxylcytosine.

In some embodiments, the nucleic acids in the original population can be single-stranded and/or double-stranded. Partitioning based on single v. double stranded-ness of the nucleic acids can be accomplished by, e.g. using labelled capture probes to partition ssDNA and using double stranded adapters to partition dsDNA.

The affinity agents can be antibodies with the desired specificity, natural binding partners or variants thereof (Bock et al., Nat Biotech 28: 1106-1114 (2010); Song et al., Nat Biotech 29: 68-72 (2011)), or artificial peptides selected e.g., by phage display to have specificity to a given target.

Examples of capture moieties contemplated herein include methyl binding domain (MBDs) and methyl binding proteins (MBPs) as described herein.

Likewise, partitioning of different forms of nucleic acids can be performed using histone binding proteins which can separate nucleic acids bound to histones from free or unbound nucleic acids. Examples of histone binding proteins that can be used in the methods disclosed herein include RBBP4 (RbAp48) and SANT domain peptides.

Although for some affinity agents and modifications, binding to the agent may occur in an essentially all or none manner depending on whether a nucleic acid bears a modification, the separation may be one of degree. In such instances, nucleic acids overrepresented in a modification bind to the agent at a greater extent that nucleic acids underrepresented in the modification. Alternatively, nucleic acids having modifications may bind in an all or nothing manner. But then, various levels of modifications may be sequentially eluted from the binding agent.

For example, in some embodiments, partitioning can be binary or based on degree/level of modifications. For example, all methylated fragments can be partitioned from unmethylated fragments using methyl-binding domain proteins (e.g., MethylMiner Methylated DNA Enrichment Kit (Thermo Fisher Scientific). Subsequently, additional partitioning may involve eluting fragments having different levels of methylation by adjusting the salt concentration in a solution with the methyl-binding domain and bound fragments. As salt concentration increases, fragments having greater methylation levels are eluted.

In some instances, the final partitions are representatives of nucleic acids having different extents of modifications (overrepresentative or underrepresentative of modifications). Overrepresentation and underrepresentation can be defined by the number of modifications born by a nucleic acid relative to the median number of modifications per strand in a population. For example, if the median number of 5-methylcytosine residues in nucleic acid in a sample is 2, a nucleic acid including more than two 5-methylcytosine residues is overrepresented in this modification and a nucleic acid with 1 or zero 5-methylcytosine residues is underrepresented. The effect of the affinity separation is to enrich for nucleic acids overrepresented in a modification in a bound phase and for nucleic acids underrepresented in a modification in an unbound phase (i.e. in solution). The nucleic acids in the bound phase can be eluted before subsequent processing.

When using MethylMiner Methylated DNA Enrichment Kit (Thermo Fisher Scientific) various levels of methylation can be partitioned using sequential elutions. For example, a hypomethylated partition (e.g., no methylation) can be separated from a methylated partition by contacting the nucleic acid population with the MBD from the kit, which is attached to magnetic beads. The beads are used to separate out the methylated nucleic acids from the non-methylated nucleic acids. Subsequently, one or more elution steps are performed sequentially to elute nucleic acids having different levels of methylation. For example, a first set of methylated nucleic acids can be eluted at a salt concentration of 160 mM or higher, e.g., at least 200 mM, 300 mM, 400 mM, 500 mM, 600 mM, 700 mM, 800 mM, 900 mM, 1000 mM, or 2000 mM. After such methylated nucleic acids are eluted, magnetic separation is once again used to separate higher level of methylated nucleic acids from those with lower level of methylation. The elution and magnetic separation steps can repeat themselves to create various partitions such as a hypomethylated partition (e.g., representative of no methylation), a methylated partition (representative of low level of methylation), and a hyper methylated partition (representative of high level of methylation).

In some methods, nucleic acids bound to an agent used for affinity separation are subjected to a wash step. The wash step washes off nucleic acids weakly bound to the affinity agent. Such nucleic acids can be enriched in nucleic acids having the modification to an extent close to the mean or median (i.e., intermediate between nucleic acids remaining bound to the solid phase and nucleic acids not binding to the solid phase on initial contacting of the sample with the agent).

The affinity separation results in at least two, and sometimes three or more partitions of nucleic acids with different extents of a modification. While the partitions are still separate, the nucleic acids of at least one partition, and usually two or three (or more) partitions are linked to nucleic acid tags, usually provided as components of adapters, with the nucleic acids in different partitions receiving different tags that distinguish members of one partition from another. The tags linked to nucleic acid molecules of the same partition can be the same or different from one another. But if different from one another, the tags may have part of their code in common so as to identify the molecules to which they are attached as being of a particular partition.

For further details regarding portioning nucleic acid samples based on characteristics such as methylation, see WO2018/119452, which is incorporated herein by reference.

In some embodiments, the nucleic acid molecules can be fractionated into different partitions based on the nucleic acid molecules that are bound to a specific protein or a fragment thereof and those that are not bound to that specific protein or fragment thereof.

Nucleic acid molecules can be fractionated based on DNA-protein binding. Protein-DNA complexes can be fractionated based on a specific property of a protein. Examples of such properties include various epitopes, modifications (e.g., histone methylation or acetylation) or enzymatic activity. Examples of proteins which may bind to DNA and serve as a basis for fractionation may include, but are not limited to, protein A and protein G. Any suitable method can be used to fractionate the nucleic acid molecules based on protein bound regions. Examples of methods used to fractionate nucleic acid molecules based on protein bound regions include, but are not limited to, SDS-PAGE, chromatin-immuno-precipitation (ChIP), heparin chromatography, and asymmetrical field flow fractionation (AF4).

In some embodiments, partitioning of the nucleic acids is performed by contacting the nucleic acids with a methylation binding domain ("MBD") of a methylation binding protein ("MBP"). MBD binds to 5-methylcytosine (5mC). MBD is coupled to paramagnetic beads, such as Dynabeads® M-280 Streptavidin via a biotin linker. Partitioning into fractions with different extents of methylation can be performed by eluting fractions by increasing the NaCl concentration.

Examples of MBPs contemplated herein include, but are not limited to:

(a) MeCP2 is a protein preferentially binding to 5-methyl-cytosine over unmodified cytosine.

(b) RPL26, PRP8 and the DNA mismatch repair protein MHS6 preferentially bind to 5-hydroxymethyl-cytosine over unmodified cytosine.

(c) FOXK1, FOXK2, FOXP1, FOXP4 and FOXI3 preferably bind to 5-formyl-cytosine over unmodified cytosine (Iurlaro et al., Genome Biol. 14: R119 (2013)).

(d) Antibodies specific to one or more methylated nucleotide bases.

In general, elution is a function of number of methylated sites per molecule, with molecules having more methylation eluting under increased salt concentrations. To elute the DNA into distinct populations based on the extent of methylation, one can use a series of elution buffers of increasing NaCl concentration. Salt concentration can range from about 100 mM to about 2500 mM NaCl. In one embodiment, the process results in three (3) partitions. Molecules are contacted with a solution at a first salt concentration and comprising a molecule comprising a methyl binding domain, which molecule can be attached to a capture moiety, such as streptavidin. At the first salt concentration a population of molecules will bind to the MBD and a population will remain unbound. The unbound population can be separated as a "hypomethylated" population. For example, a first partition representative of the hypomethylated form of DNA is that which remains unbound at a low salt concentration, e.g., 100 mM or 160 mM. A second partition representative of intermediate methylated DNA is eluted using an intermediate salt concentration, e.g., between 100 mM and 2000 mM concentration. This is also separated from the sample. A third partition representative of hypermethylated form of DNA is eluted using a high salt concentration, e.g., at least about 2000 mM.

a. Tagging of Partitions

In some embodiments, two or more partitions, e.g., each partition, is/are differentially tagged. Tags can be molecules, such as nucleic acids, containing information that indicates a feature of the molecule with which the tag is associated. For example, molecules can bear a sample tag (which distinguishes molecules in one sample from those in a different sample), a partition tag (which distinguishes molecules in one partition from those in a different partition) or a molecular tag (which distinguishes different molecules from one another (in both unique and non-unique tagging scenarios). In certain embodiments, a tag can comprise one or a combination of barcodes. As used herein, the term "barcode" refers to a nucleic acid molecule having a particular nucleotide sequence, or to the nucleotide sequence, itself, depending on context. A barcode can have, for example, between 10 and 100 nucleotides. A collection of barcodes can have degenerate sequences or can have sequences having a certain Hamming distance, as desired for the specific purpose. So, for example, a sample index, partition index or molecular index can be comprised of one barcode or a combination of two barcodes, each attached to different ends of a molecule.

Tags can be used to label the individual polynucleotide population partitions so as to correlate the tag (or tags) with a specific partition. Alternatively, tags can be used in embodiments of the invention that do not employ a partitioning step. In some embodiments, a single tag can be used to label a specific partition. In some embodiments, multiple different tags can be used to label a specific partition. In embodiments employing multiple different tags to label a specific partition, the set of tags used to label one partition can be readily differentiated for the set of tags used to label other partitions. In some embodiments, the tags may have additional functions, for example the tags can be used to index sample sources or used as unique molecular identifiers (which can be used to improve the quality of sequencing data by differentiating sequencing errors from mutations, for example as in Kinde et al., Proc Nat'l Acad Sci USA 108: 9530-9535 (2011). Kou et al., *PLoS ONE,* 11: e0146638 (2016)) or used as non-unique molecule identifiers, for example as described in U.S. Pat. No. 9,598,731. Similarly, in some embodiments, the tags may have additional functions, for example the tags can be used to index sample sources or used as non-unique molecular identifiers (which can be used to improve the quality of sequencing data by differentiating sequencing errors from mutations).

In one embodiment, partition tagging comprises tagging molecules in each partition with a partition tag. After re-combining partitions and sequencing molecules, the partition tags identify the source partition. In another embodiment, different partitions are tagged with different sets of molecular tags, e.g., comprised of a pair of barcodes. In this way, each molecular barcode indicates the source partition as well as being useful to distinguish molecules within a partition. For example, a first set of 35 barcodes can be used to tag molecules in a first partition, while a second set of 35 barcodes can be used tag molecules in a second partition.

In some embodiments, after partitioning and tagging with partition tags, the molecules may be pooled for sequencing in a single run. In some embodiments, a sample tag is added to the molecules, e.g., in a step subsequent to addition of partition tags and pooling. Sample tags can facilitate pooling material generated from multiple samples for sequencing in a single sequencing run.

Alternatively, in some embodiments, partition tags may be correlated to the sample as well as the partition. As a simple example, a first tag can indicate a first partition of a first sample; a second tag can indicate a second partition of the first sample; a third tag can indicate a first partition of a second sample; and a fourth tag can indicate a second partition of the second sample.

While tags may be attached to molecules already partitioned based on one or more characteristics, the final tagged molecules in the library may no longer possess that characteristic. For example, while single stranded DNA molecules may be partitioned and tagged, the final tagged molecules in the library are likely to be double stranded. Similarly, while DNA may be subject to partition based on different levels of methylation, in the final library, tagged molecules derived from these molecules are likely to be unmethylated. Accordingly, the tag attached to molecule in the library typically indicates the characteristic of the "parent molecule" from which the ultimate tagged molecule is derived, not necessarily to characteristic of the tagged molecule, itself.

As an example, barcodes 1, 2, 3, 4, etc. are used to tag and label molecules in the first partition; barcodes A, B, C, D, etc. are used to tag and label molecules in the second partition; and barcodes a, b, c, d, etc. are used to tag and label molecules in the third partition. Differentially tagged partitions can be pooled prior to sequencing. Differentially tagged partitions can be separately sequenced or sequenced together concurrently, e.g., in the same flow cell of an Illumina sequencer.

After sequencing, analysis of reads to detect genetic variants can be performed on a partition-by-partition level, as well as a whole nucleic acid population level. Tags are used to sort reads from different partitions. Analysis can include in silico analysis to determine genetic and epigenetic variation (one or more of methylation, chromatin structure, etc.) using sequence information, genomic coordinates length, coverage and/or copy number. In some embodiments, higher coverage can correlate with higher nucleosome occupancy in genomic region while lower coverage can correlate with lower nucleosome occupancy or a nucleosome depleted region (NDR).

b. Determination of 5-Methylcytosine Pattern of Nucleic Acids; Bisulfite Sequencing Bisulfite-based sequencing and variants thereof provides another means of determining the methylation pattern of a nucleic acid that does not rely on partitioning based on methylation level before sequencing. In some embodiments, determining the methylation pattern comprises distinguishing 5-methylcytosine (5mC) from non-methylated cytosine. In some embodiments, determining methylation pattern comprises distinguishing N-methyladenine from non-methylated adenine. In some embodiments, determining the methylation pattern comprises distinguishing 5-hydroxymethyl cytosine (5hmC), 5-formyl cytosine (5fC), and 5-carboxylcytosine (5caC) from non-methylated cytosine. Examples of bisulfite sequencing include but are not limited to oxidative bisulfite sequencing (OX-BS-seq), Tet-assisted bisulfite sequencing (TAB-seq), and reduced bisulfite sequencing (redBS-seq). In some embodiments, determining the methylation pattern comprises whole genome bisulfite sequencing, e.g., as in MethylC-seq (Urich et al., *Nature Protocols* 10:475-483 (2015)). In some embodiments, determining the methylation pattern comprises array-based methylation pattern determination, e.g., as in Methylation EPIC Beadchip or the use of Illumina Infinium arrays (e.g., Human Methylation 450 arrays) (see The Cancer Genome Atlas Research Network, Nature 507:315-322 (2014)). In some embodiments, determining the methylation pattern comprises bisulfite PCR. In some embodiments, determining the methylation pattern comprises EM-Seq (US 2013/0244237 A1). In some embodiments, determining the methylation pattern comprises TAPS (WO 2019/136413 A1).

Oxidative bisulfite sequencing (OX-BS-seq) is used to distinguish between 5mC and 5hmC, by first converting the 5hmC to SIC, and then proceeding with bisulfite sequencing. Tet-assisted bisulfite sequencing (TAB-seq) can also be used to distinguish 5mc and 5hmC. In TAB-seq, 5hmC is protected by glucosylation. A Tet enzyme is then used to convert 5mC to 5caC before proceeding with bisulfite sequencing. Reduced bisulfite sequencing is used to distinguish SIC from modified cytosines.

Generally, in bisulfite sequencing, a nucleic acid sample is divided into two aliquots and one aliquot is treated with bisulfite. The bisulfite converts native cytosine and certain modified cytosine nucleotides (e.g. 5-formyl cytosine or 5-carboxylcytosine) to uracil whereas other modified cytosines (e.g., 5-methylcytosine. 5-hydroxylmethylcystosine) are not converted. Comparison of nucleic acid sequences of molecules from the two aliquots indicates which cytosines were and were not converted to uracils. Consequently, cytosines which were and were not modified can be determined. The initial splitting of the sample into two aliquots is disadvantageous for samples containing only small amounts of nucleic acids, and/or composed of heterogeneous cell/tissue origins such as bodily fluids containing cell-free DNA.

Accordingly, in some embodiments, bisulfite sequencing is performed without initially splitting a sample into two aliquots, e.g., as follows. In some embodiments, nucleic acids in a population are linked to a capture moiety such as any of those described herein, i.e., a label that can be captured or immobilized. Following linking of capture moieties to sample nucleic acids, the sample nucleic acids serve as templates for amplification. Following amplification, the original templates remain linked to the capture moieties but amplicons are not linked to capture moieties.

The capture moiety can be linked to sample nucleic acids as a component of an adapter, which may also provide amplification and/or sequencing primer binding sites. In some methods, sample nucleic acids are linked to adapters at both ends, with both adapters bearing a capture moiety. Preferably any cytosine residues in the adopters are modified, such as by 5methylcytosine, to protect against the action of bisulfite. In some instances, the capture moieties are linked to the original templates by a cleavable linkage (e.g., photocleavable desthiobiotin-TEG or uracil residues cleavable with USER™ enzyme, Chem. Commun. (Camb). 51: 3266-3269 (2015)), in which case the capture moieties can, if desired, be removed.

The amplicons are denatured and contacted with an affinity reagent for the capture tag. Original templates bind to the affinity reagent whereas nucleic acid molecules resulting from amplification do not. Thus, the original templates can be separated from nucleic acid molecules resulting from amplification.

Following separation of original templates from nucleic acid molecules resulting from amplification, the original templates can be subjected to bisulfite treatment. Alternatively, the amplification products can be subjected to bisulfite treatment and the original template population not. Following such treatment, the respective populations can be amplified (which in the case of the original template population converts uracils to thymines). The populations can also be subjected to biotin probe hybridization for capture. The respective populations are then analyzed and sequences compared to determine which cytosines were 5-methylated (or 5-hydroxylmethylated) in the original sample. Detection of a T nucleotide in the template population (corresponding to an unmethylated cytosine converted to uracil) and a C nucleotide at the corresponding position of the amplified population indicates an unmodified C. The presence of C's at corresponding positions of the original template and amplified populations indicates a modified C in the original sample.

Figure 4:
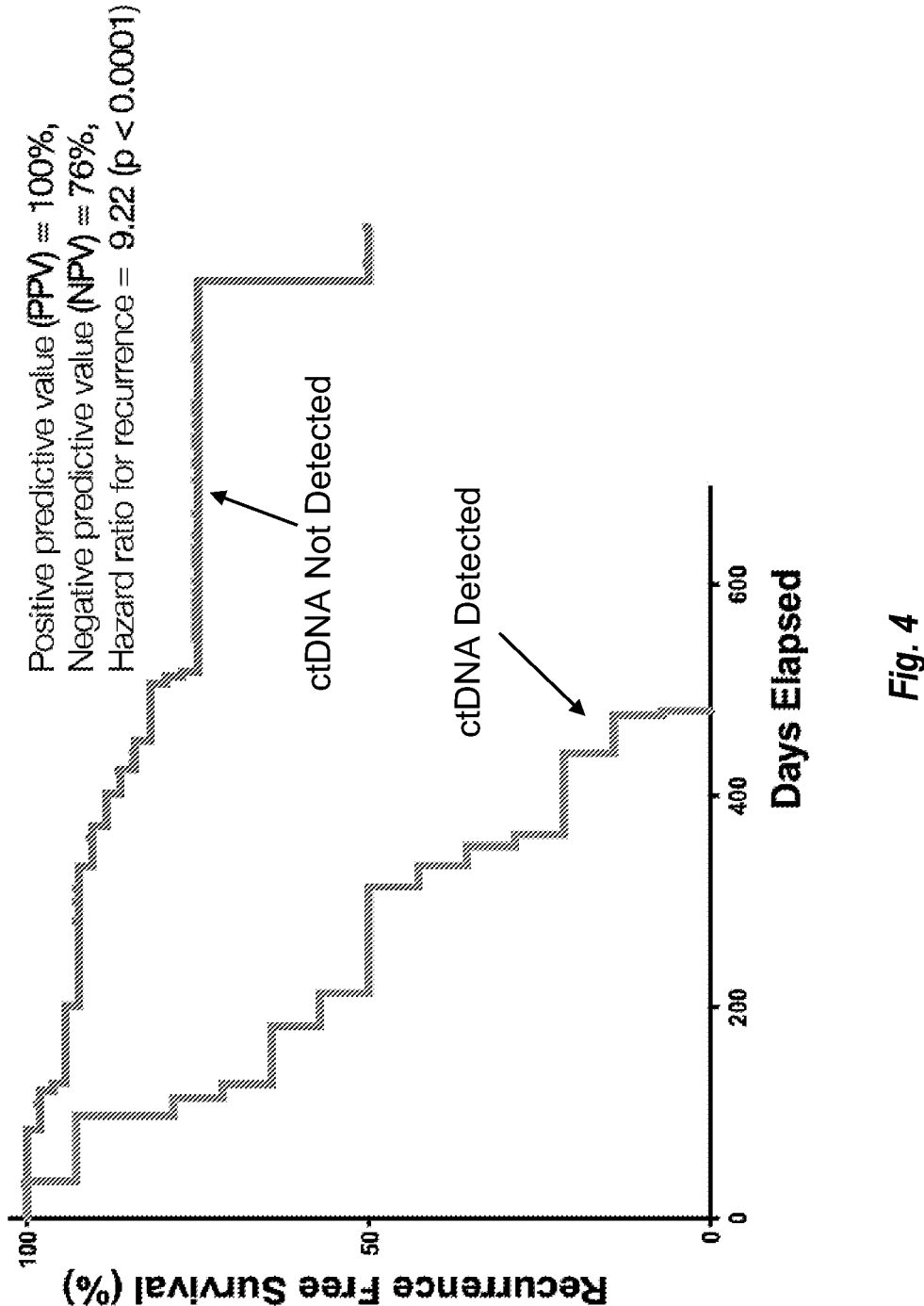
FIG. 4 shows recurrence free survival over time for subjects in whom ctDNA was or was not detected as described in Example iii.

In some embodiments, a method uses sequential DNA-seq and bisulfite-seq (BIS-seq) NGS library preparation of molecular tagged DNA libraries (see WO 2018/119452, e.g., at FIG. 4). This process is performed by labeling of adapters (e.g., biotin), DNA-seq amplification of whole library, parent molecule recovery (e.g. streptavidin bead pull down), bisulfite conversion and BIS-seq. In some embodiments, the method identifies 5-methylcytosine with single-base resolution, through sequential NGS-preparative amplification of parent library molecules with and without bisulfite treatment. This can be achieved by modifying the 5-methylated NGS-adapters (directional adapters; Y-shaped/forked with 5-methylcytosine replacing) used in BIS-seq with a label (e.g., biotin) on one of the two adapter strands. Sample DNA molecules are adapter ligated, and amplified (e.g., by PCR). As only the parent molecules will have a labeled adapter end, they can be selectively recovered from their amplified progeny by label-specific capture methods (e.g., streptavidin-magnetic beads). As the parent molecules retain 5-methylation marks, bisulfite conversion on the captured library will yield single-base resolution 5-methylation status upon BIS-seq, retaining molecular information to corresponding DNA-seq. In some embodiments, the bisulfite treated library can be combined with a non-treated library prior to capture/NGS by addition of a sample tag DNA sequence in standard multiplexed NGS workflow. As with BIS-seq workflows, bioinformatics analysis can be carried out for genomic alignment and 5-methylated base identification. In sum, this method provides the ability to selectively recover the parent, ligated molecules, carrying 5-methylcytosine marks, after library amplification, thereby allowing for parallel processing for bisulfite converted DNA. This overcomes the destructive nature of bisulfite treatment on the quality/sensitivity of the DNA-seq information extracted from a workflow. With this method, the recovered ligated, parent DNA molecules (via labeled adapters) allow amplification of the complete DNA library and parallel application of treatments that elicit epigenetic DNA modifications. The present disclosure discusses the use of BIS-seq methods to identify cytosine-5-methylation (5-methylcytosine), but the use of BIS-seq methods is not required in many embodiments. Variants of BIS-seq have been developed to identify hydroxymethylated cytosines (5hmC; OX-BS-seq, TAB-seq), formylcytosine (5fC; redBS-seq) and carboxyl cytosines. These methodologies can be implemented with the sequential/parallel library preparation described herein.

c. Alternative Methods of Modified Nucleic Add Analysis

In some such methods, a population of nucleic acids bearing the modification to different extents (e.g., 0, 1, 2, 3, 4, 5 or more methyl groups per nucleic acid molecule) is contacted with adapters before fractionation of the population depending on the extent of the modification. Adapters attach to either one end or both ends of nucleic acid molecules in the population. Preferably, the adapters include different tags of sufficient numbers that the number of combinations of tags results in a low probability e.g., 95.99 or 99.9% of two nucleic acids with the same start and stop points receiving the same combination of tags. Following attachment of adapters, the nucleic acids are amplified from primers binding to the primer binding sites within the adapters. Adapters, whether bearing the same or different tags, can include the same or different primer binding sites, but preferably adapters include the same primer binding site. Following amplification, the nucleic acids are contacted with an agent that preferably binds to nucleic acids bearing the modification (such as the previously described such agents). The nucleic acids are separated into at least two partitions differing in the extent to which the nucleic acids bear the modification from binding to the agents. For example, if the agent has affinity for nucleic acids bearing the modification, nucleic acids overrepresented in the modification (compared with median representation in the population) preferentially bind to the agent, whereas nucleic acids underrepresented for the modification do not bind or are more easily eluted from the agent. Following separation, the different partitions can then be subject to further processing steps, which typically include further amplification, and sequence analysis, in parallel but separately. Sequence data from the different partitions can then be compared.

Such a separation scheme can be performed using the following exemplary procedure. Nucleic acids are linked at both ends to Y-shaped adapters including primer binding sites and tags. The molecules are amplified. The amplified molecules are then fractionated by contact with an antibody preferentially binding to 5-methylcytosine to produce two partitions. One partition includes original molecules lacking methylation and amplification copies having lost methylation. The other partition includes original DNA molecules with methylation. The two partitions are then processed and sequenced separately with further amplification of the methylated partition. The sequence data of the two partitions can then be compared. In this example, tags are not used to distinguish between methylated and unmethylated DNA but rather to distinguish between different molecules within these partitions so that one can determine whether reads with the same start and stop points are based on the same or different molecules.

The disclosure provides further methods for analyzing a population of nucleic acid in which at least some of the nucleic acids include one or more modified cytosine residues, such as 5-methylcytosine and any of the other modifications described previously. In these methods, the population of nucleic acids is contacted with adapters including one or more cytosine residues modified at the 5C position, such as 5-methylcytosine. Preferably all cytosine residues in such adapters are also modified, or all such cytosines in a primer binding region of the adapters are modified. Adapters attach to both ends of nucleic acid molecules in the population. Preferably, the adapters include different tags of sufficient numbers that the number of combinations of tags results in a low probability e.g., 95, 99 or 99.9% of two nucleic acids with the same start and stop points receiving the same combination of tags. The primer binding sites in such adapters can be the same or different, but are preferably the same. After attachment of adapters, the nucleic acids are amplified from primers binding to the primer binding sites of the adapters. The amplified nucleic acids are split into first and second aliquots. The first aliquot is assayed for sequence data with or without further processing. The sequence data on molecules in the first aliquot is thus determined irrespective of the initial methylation state of the nucleic acid molecules. The nucleic acid molecules in the second aliquot are treated with bisulfite. This treatment converts unmodified cytosines to uracils. The bisulfite treated nucleic acids are then subjected to amplification primed by primers to the original primer binding sites of the adapters linked to nucleic acid. Only the nucleic acid molecules originally linked to adapters (as distinct from amplification products thereof) are now amplifiable because these nucleic acids retain cytosines in the primer binding sites of the adopters, whereas amplification products have lost the methylation of these cytosine residues, which have undergone conversion to uracils in the bisulfite treatment. Thus, only original molecules in the populations, at least some of which are methylated, undergo amplification. After amplification, these nucleic acids are subject to sequence analysis. Comparison of sequences determined from the first and second aliquots can indicate among other things, which cytosines in the nucleic acid population were subject to methylation.

Such an analysis can be performed using the following exemplary procedure. Methylated DNA is linked to Y-shaped adapters at both ends including primer binding sites and tags. The cytosines in the adapters are 5-methylated. The methylation of the primers serves to protect the primer binding sites in a subsequent bisulfite step. After attachment of adapters, the DNA molecules are amplified. The amplification product is split into two aliquots for sequencing with and without bisulfite treatment. The aliquot not subjected to bisulfite sequencing can be subjected to sequence analysis with or without further processing. The other aliquot is treated with bisulfite, which converts unmethylated cytosines to uracils. Only primer binding sites protected by methylation of cytosines can support amplification when contacted with primers specific for original primer binding sites. Thus, only original molecules and not copies from the first amplification are subjected to further amplification. The further amplified molecules are then subjected to sequence analysis. Sequences can then be compared from the two aliquots. As in the separation scheme discussed above, nucleic acid tags in adapters are not used to distinguish between methylated and unmethylated DNA but to distinguish nucleic acid molecules within the same partition.

d. Methylation-Sensitive PCR

In some embodiments, methylation-sensitive amplification is used to evaluate methylation in hypermethylation-variable and/or hypomethylation-variable target regions. Various steps may be rendered methylation-sensitive by adapting known approaches to methods described herein.

For example, a sample may be divided into aliquots, e.g., before or after a capturing step as described herein, and one aliquot can be digested with a methylation-sensitive restriction enzyme, e.g., as described in Moore et al., Methods Mol Biol. 325:239-49 (2006), which is incorporated herein by reference. Unmethylated sequences are digested in this aliquot. The digested and undigested aliquots can then be carried forward through appropriate steps as described herein (amplification, optionally tagging, sequencing, and the like) and the sequences analyzed to determine the degree of digestion in the treated sample, which reflects the presence of unmethylated cytosines. Alternatively, division into aliquots can be avoided by amplifying a sample, separating amplified material from original templates, and then digesting the original material with a methylation-sensitive restriction enzyme before performing a further amplification, e.g., as discussed above with respect to bisulfite sequencing.

In another example, a sample can be sample may be divided into aliquots and one aliquot treated to convert unmethylated cytosines to uracil, e.g., as described in US 2003/0082600, which is incorporated herein by reference, prior to capture. The conversion of unmethylated cytosines to uracil will reduce the efficiency of capture of target regions with low methylation by altering the sequence of the regions. The treated and untreated aliquots can then be carried forward through appropriate steps as described herein (capture, amplification, optionally tagging, sequencing, and the like) and the sequences analyzed to determine the degree of depletion of target regions in the treated sample, which reflects the presence of unmethylated cytosines.

4. Subjects

In some embodiments, the DNA (e.g., cfDNA) is obtained from a subject having a cancer. In some embodiments, the DNA (e.g., cfDNA) is obtained from a subject suspected of having a cancer. In some embodiments, the DNA (e.g., cfDNA) is obtained from a subject having a tumor. In some embodiments, the DNA (e.g., cfDNA) is obtained from a subject suspected of having a tumor. In some embodiments, the DNA (e.g., cfDNA) is obtained from a subject having neoplasia. In some embodiments, the DNA (e.g., cfDNA) is obtained from a subject suspected of having neoplasia. In some embodiments, the DNA (e.g., cfDNA) is obtained from a subject in remission from a tumor, cancer, or neoplasia (e.g., following chemotherapy, surgical resection, radiation, or a combination thereof). In any of the foregoing embodiments, the cancer, tumor, or neoplasia or suspected cancer, tumor, or neoplasia may be of the lung, colon, rectum, kidney, breast, prostate, or liver. In some embodiments, the cancer, tumor, or neoplasia or suspected cancer, tumor, or neoplasia is of the lung. In some embodiments, the cancer, tumor, or neoplasia or suspected cancer, tumor, or neoplasia is of the colon or rectum. In some embodiments, the cancer, tumor, or neoplasia or suspected cancer, tumor, or neoplasia is of the breast. In some embodiments, the cancer, tumor, or neoplasia or suspected cancer, tumor, or neoplasia is of the prostate. In any of the foregoing embodiments, the subject may be a human subject.

In some embodiments, the subject was previously diagnosed with a caner. e.g., any of the cancers noted above or elsewhere herein. Such a subject may have previously received one or more previous cancer treatments, e.g., surgery, chemotherapy, radiation, and/or immunotherapy. In some embodiments, a sample (e.g., cfDNA) is obtained from a previously diagnosed and treated subject at one or more preselected time points following the one or more previous cancer treatments.

The sample (e.g., cfDNA) obtained from the subject may be sequenced to provide a set of sequence information, which may include sequencing captured DNA molecules of the sequence-variable target region set a greater depth of sequencing than captured DNA molecules of the epigenetic target region set, as described in detail elsewhere herein.

5. Exemplary Method for Molecular Tag Identification of MBD-Bead Partitioned Libraries An exemplary method for molecular tag identification of MBD-bead partitioned libraries through NGS is as follows:

i) Physical partitioning of an extracted DNA sample (e.g., extracted blood plasma DNA from a human sample, which has optionally been subjected to target capture as described herein) using a methyl-binding domain protein-bead purification kit, saving all elutions from process for downstream processing.

ii) Parallel application of differential molecular tags and NGS-enabling adapter sequences to each partition. For example, the hypermethylated, residual methylation ('wash'), and hypomethylated partitions are ligated with NGS-adapters with molecular tags.

iii) Re-combining all molecular tagged partitions, and subsequent amplification using adapter-specific DNA primer sequences.

iv) Capture/hybridization of re-combined and amplified total library, targeting genomic regions of interest (e.g., cancer-specific genetic variants and differentially methylated regions).

v) Re-amplification of the captured DNA library, appending a sample tag. Different samples are pooled and assayed in multiplex on an NGS instrument.

vi) Bioinformatics analysis of NGS data, with the molecular tags being used to identify unique molecules, as well deconvolution of the sample into molecules that were differentially MBD-partitioned. This analysis can yield information on relative 5-methylcytosine for genomic regions, concurrent with standard genetic sequencing/variant detection.

The exemplary method set forth above may further comprise any compatible feature of methods according to this disclosure set forth elsewhere herein.

6. Exemplary Workflows

Exemplary workflows for partitioning and library preparation are provided herein. In some embodiments, some or all features of the partitioning and library preparation workflows may be used in combination. The exemplary workflows set forth above may further comprise any compatible feature of methods according to this disclosure set forth elsewhere herein.

a. Partitioning

In some embodiments, sample DNA (for e.g., between 1 and 300 ng) is mixed with an appropriate amount of methyl binding domain (MBD) buffer (the amount of MBD buffer depends on the amount of DNA used) and magnetic beads conjugated with MBD proteins and incubated overnight. Methylated DNA (hypermethylated DNA) binds the MBD protein on the magnetic beads during this incubation. Non-methylated (hypomethylated DNA) or less methylated DNA (intermediately methylated) is washed away from the beads with buffers containing increasing concentrations of salt. For example, one, two, or more fractions containing non-methylated, hypomethylated, and/or intermediately methylated DNA may be obtained from such washes. Finally, a high salt buffer is used to elute the heavily methylated DNA (hypermethylated DNA) from the MBD protein. In some embodiments, these washes result in three partitions (hypomethylated partition, intermediately methylated fraction and hypermethylated partition) of DNA having increasing levels of methylation.

In some embodiments, the three partitions of DNA are desalted and concentrated in preparation for the enzymatic steps of library preparation.

b. Library Preparation

In some embodiments (e.g., after concentrating the DNA in the partitions), the partitioned DNA is made ligatable, e.g., by extending the end overhangs of the DNA molecules are extended, and adding adenosine residues to the 3' ends of fragments and phosphorylating the 5' end of each DNA fragment. DNA ligase and adapters are added to ligate each partitioned DNA molecule with an adopter on each end. These adapters contain partition tags (e.g., non-random, non-unique barcodes) that are distinguishable from the partition tags in the adapters used in the other partitions. After ligation, the three partitions are pooled together and are amplified (e.g., by PCR, such as with primers specific for the adapters).

Following PCR, amplified DNA may be cleaned and concentrated prior to capture. The amplified DNA is contacted with a collection of probes described herein (which may be, e.g., biotinylated RNA probes) that target specific regions of interest. The mixture is incubated, e.g., overnight, e.g., in a salt buffer. The probes are captured (e.g., using streptavidin magnetic beads) and separated from the amplified DNA that was not captured, such as by a series of salt washes, thereby providing a captured set of DNA. After capture, the DNA of the captured set is amplified by PCR. In some embodiments, the PCR primers contain a sample tag, thereby incorporating the sample tag into the DNA molecules. In some embodiments, DNA from different samples is pooled together and then multiplex sequenced, e.g., using an Illumina NovaSeq sequencer.

III. General Features of the Methods

1. Samples

A sample can be any biological sample isolated from a subject. A sample can be a bodily sample. Samples can include body tissues, such as known or suspected solid tumors, whole blood, platelets, serum, plasma, stool, red blood cells, white blood cells or leucocytes, endothelial cells, tissue biopsies, cerebrospinal fluid synovial fluid, lymphatic fluid, ascites fluid, interstitial or extracellular fluid, the fluid in spaces between cels, including gingival crevicular fluid, bone marrow, pleural effusions, cerebrospinal fluid, saliva, mucous, sputum, semen, sweat, urine. Samples are preferably body fluids, particularly blood and fractions thereof, and urine. A sample can be in the form originally isolated from a subject or can have been subjected to further processing to remove or add components, such as cells, or enrich for one component relative to another. Thus, a preferred body fluid for analysis is plasma or serum containing cell-free nucleic acids. A sample can be isolated or obtained from a subject and transported to a site of sample analysis. The sample may be preserved and shipped at a desirable temperature, e.g., room temperature, 4° C., −20° C., and/or −80° C. A sample can be isolated or obtained from a subject at the site of the sample analysis. The subject can be a human a mammal, an animal, a companion animal, a service animal, or a pet. The subject may have a cancer. The subject may not have cancer or a detectable cancer symptom. The subject may have been treated with one or more cancer therapy, e.g., any one or more of chemotherapies, antibodies, vaccines or biologies. The subject may be in remission. The subject may or may not be diagnosed of being susceptible to cancer or any cancer-associated genetic mutations/disorders.

The volume of plasma can depend on the desired read depth for sequenced regions. Exemplary volumes are 0.4-40 ml, 5-20 ml, 10-20 ml. For examples, the volume can be 0.5 mL, 1 mL, 5 mL 10 mL, 20 mL, 30 mL, or 40 mL. A volume of sampled plasma may be 5 to 20 mL.

A sample can comprise various amount of nucleic acid that contains genome equivalents. For example, a sample of about 30 ng DNA can contain about 10,000 ($10^4$) haploid human genome equivalents and, in the case of cfDNA, about 200 billion ($2\times10^{11}$) individual polynucleotide molecules. Similarly, a sample of about 100 ng of DNA can contain about 30,000 haploid human genome equivalents and, in the case of cfDNA, about 600 billion individual molecules.

A sample can comprise nucleic acids from different sources, e.g., from cells and cell-free of the same subject, from cells and cell-free of different subjects. A sample can comprise nucleic acids carrying mutations. For example, a sample can comprise DNA carrying germline mutations and/or somatic mutations. Germline mutations refer to mutations existing in germline DNA of a subject. Somatic mutations refer to mutations originating in somatic cells of a subject, e.g., cancer cells. A sample can comprise DNA carrying cancer-associated mutations (e.g., cancer-associated somatic mutations). A sample can comprise an epigenetic variant (i.e. a chemical or protein modification), wherein the epigenetic variant associated with the presence of a genetic variant such as a cancer-associated mutation. In some embodiments, the sample comprises an epigenetic variant associated with the presence of a genetic variant, wherein the sample does not comprise the genetic variant.

Exemplary amounts of cell-free nucleic acids in a sample before amplification range from about 1 fg to about 1 µg, e.g., 1 pg to 200 ng, 1 ng to 100 ng, 10 ng to 1000 ng. For example, the amount can be up to about 600 ng, up to about 500 ng, up to about 400 ng, up to about 300 ng, up to about 200 ng, up to about 100 ng, up to about 50 ng, or up to about 20 ng of cell-free nucleic acid molecules. The amount can be at least 1 fg, at least 10 fg, at least 100 fg, at least 1 pg, at least 10 pg, at least 100 pg, at least 1 ng, at least 10 ng, at least 100 ng, at least 150 ng, or at least 200 ng of cell-free nucleic acid molecules. The amount can be up to 1 femtogram (fg), 10 fg, 100 fg, 1 picogram (pg), 10 pg, 100 pg, 1 ng, 10 ng, 100 ng, 150 ng, 200 ng, 250 ng or 300 ng of cell-free nucleic acid molecules. The method can comprise obtaining 1 femtogram (fg) to 200 ng.

Cell-free nucleic acids are nucleic acids not contained within or otherwise bound to a cell or in other words nucleic acids remaining in a sample after removing intact cells. Cell-free nucleic acids include DNA, RNA, and hybrids thereof, including genomic DNA, mitochondrial DNA, siRNA, miRNA, circulating RNA (cRNA), tRNA, rRNA, small nucleolar RNA (snoRNA), Piwi-interacting RNA (piRNA), long non-coding RNA (long ncRNA), or fragments of any of these. Cell-free nucleic acids can be double-stranded, single-stranded, or a hybrid thereof. A cell-free nucleic acid can be released into bodily fluid through secretion or cell death processes, e.g., cellular necrosis and apoptosis. Some cell-free nucleic acids are released into bodily fluid from cancer cells e.g., circulating tumor DNA, (ctDNA). Others are released from healthy cells. In some embodiments, cfDNA is cell-free fetal DNA (cfDNA) In some embodiments, cell free nucleic acids are produced by tumor cells. In some embodiments, cell free nucleic acids are produced by a mixture of tumor cells and non-tumor cells.

Cell-free nucleic acids have an exemplary size distribution of about 100-500 nucleotides, with molecules of 110 to about 230 nucleotides representing about 90% of molecules, with a mode of about 168 nucleotides and a second minor peak in a range between 240 to 440 nucleotides.

Cell-free nucleic acids can be isolated from bodily fluids through a fractionation or partitioning step in which cell-free nucleic acids, as found in solution, are separated from intact cells and other non-soluble components of the bodily fluid. Partitioning may include techniques such as centrifugation or filtration. Alternatively, cells in bodily fluids can be lysed and cell-free and cellular nucleic acids processed together. Generally, after addition of buffers and wash steps, nucleic acids can be precipitated with an alcohol. Further clean up steps may be used such as silica-based columns to remove contaminants or salts. Non-specific bulk carrier nucleic acids, such as C 1 DNA, DNA or protein for bisulfite sequencing, hybridization, and/or ligation, may be added throughout the reaction to optimize certain aspects of the procedure such as yield.

After such processing, samples can include various forms of nucleic acid including double stranded DNA, single stranded DNA and single stranded RNA. In some embodiments, single stranded DNA and RNA can be converted to double stranded forms so they are included in subsequent processing and analysis steps.

Double-stranded DNA molecules in a sample and single stranded nucleic acid molecules converted to double stranded DNA molecules can be linked to adapters at either one end or both ends. Typically, double stranded molecules are blunt ended by treatment with a polymerase with a 5'-3' polymerase and a 3'-5' exonuclease (or proof-reading function), in the presence of all four standard nucleotides. Klenow large fragment and T4 polymerase are examples of suitable polymerase. The blunt ended DNA molecules can be ligated with at least partially double stranded adapter (e.g., a Y shaped or bell-shaped adapter). Alternatively, complementary nucleotides can be added to blunt ends of sample nucleic acids and adapters to facilitate ligation. Contemplated herein are both blunt end ligation and sticky end ligation. In blunt end ligation, both the nucleic acid molecules and the adapter tags have blunt ends. In sticky-end ligation, typically, the nucleic acid molecules bear an "A" overhang and the adapters bear a "T" overhang.

2. Tags

Tap comprising barcodes can be incorporated into or otherwise joined to adapters. Tap can be incorporated by ligation, overlap extension PCR among other methods.

a. Molecular Tagging Strategies

Molecular tagging refers to a tagging practice that allows one to differentiate molecules from which sequence reads originated. Tagging strategies can be divided into unique tagging and non-unique tagging strategies. In unique tagging, all or substantially all of the molecules in a sample bear a different tag, so that reads can be assigned to original molecules based on tag information alone. Tap used in such methods are sometimes referred to as "unique tags". In non-unique tagging, different molecules in the same sample can bear the same tag, so that other information in addition to tag information is used to assign a sequence read to an original molecule. Such information may include start and stop coordinate, coordinate to which the molecule maps, start or stop coordinate alone, etc. Tap used in such methods are sometimes referred to as "non-unique tags". Accordingly, it is not necessary to uniquely tag every molecule in a sample. It suffices to uniquely tag molecules falling within an identifiable class within a sample. Thus, molecules in different identifiable families can bear the same tag without loss of information about the identity of the tagged molecule.

In certain embodiments of non-unique tagging, the number of different tap used can be sufficient that there is a very high likelihood (e.g., at least 99%, at least 99.9%, at least 99.99% or at least 99.999%) that all molecules of a particular group bear a different tag. It is to be noted that when barcodes are used as tags, and when barcodes are attached, e.g., randomly, to both ends of a molecule, the combination of barcodes, together, can constitute a tag. This number, in term, is a function of the number of molecules falling into the calls. For example, the class may be all molecules mapping to the same start-stop position on a reference genome. The class may be all molecules mapping across a particular genetic locus, e.g., a particular base or a particular region (e.g., up to 100 bases or a gene or an exon of a gene). In certain embodiments, the number of different tags used to uniquely identify a number of molecules, z, in a class ca be between any of $2*z$, $3*z$, $4*z$, $5*z$, $6*z$, $7*z$, $8*z$, $9*z$, $10*z$, $11*z$, $12*z$, $13*z$, $14*z$, $15*z$, $16*z$, $17*z$, $18*z$, $19*z$, $20*z$ or $100*z$ (e.g., lower limit) and any of $100,000*z$, $10,000*z$, $1000*z$ or $100*z$ (e.g., upper limit).

For example, in a sample of about 3 ng to 30 ng of human cell free DNA, one expects around $10^3$-$10^4$ molecules to map to a particular nucleotide coordinate, and between about 3 and 10 molecules having any start coordinate to share the same stop coordinate. Accordingly, about 50 to about 50,000 different tags (e.g., between about 6 and 220 barcode combinations) can suffice to uniquely tag all such molecules. To uniquely tag all $10^3$-$10^4$ molecules mapping across a nucleotide coordinate, about 1 million to about 20 million different tags would be required.

Generally, assignment of unique or non-unique tags barcodes in reactions follows methods and systems described by US patent applications 20010053519, 20030152490, 20110160078, and U.S. Pat. Nos. 6,582,908 and 7,537,898 and 9,598,731. Tags can be linked to sample nucleic acids randomly or non-randomly.

In some embodiments, the tagged nucleic acids are sequenced after loading into a microwell plate. The microwell plate can have 96,384, or 1536 microwells. In some cases, they are introduced at an expected ratio of unique tags to microwells. For example, the unique tags may be loaded so that more than about 1, 2, 3, 4, 5, 6, 7, 8, 9, 10, 20, 50, 100, 500, 1000, 5000, 10000, 50,000, 100,000, 500,000, 1,000,000, 10,000,000, 50,000,000 or 1,000,000,000 unique tags are loaded per genome sample. In some cases, the unique tags may be loaded so that less than about 2, 3, 4, 5, 6, 7, 8, 9, 10, 20, 50, 100, 500, 1000, 5000, 10000, 50,000, 100,000, 500,000, 1,000,000, 10,000,000, 50,000,000 or 1,000,000,000 unique tags are loaded per genome sample. In some cases, the average number of unique tags loaded per sample genome is less than, or greater than, about 1, 2, 3, 4, 5, 6, 7, 8, 9, 10, 20, 50, 100, 500, 1000, 5000, 10000, 50,000, 100,000, 500,000, 1,000,000, 10,000,000, 50,000,000 or 1,000,000,000 unique tags per genome sample.

A preferred format uses 20-50 different tags (e.g., barcodes) ligated to both ends of target nucleic acids. For example, 35 different tags (e.g., barcodes) ligated to both ends of target molecules creating 35×35 permutations, which equals 1225 tag combinations for 35 tags. Such numbers of tags are sufficient so that different molecules having the same start and stop points have a high probability (e.g., at least 94%. 99.5%. 99.99%. 99.999%) of receiving different combinations of tags. Other barcode combinations include any number between 10 and 500, e.g., about 15×15, about 35×35, about 75×75, about 100×100, about 250×250, about 500×500.

In some cases, unique tags may be predetermined or random or semi-random sequence oligonucleotides. In other cases, a plurality of barcodes may be used such that barcodes are not necessarily unique to one another in the plurality. In this example, barcodes may be ligated to individual molecules such that the combination of the barcode and the sequence it may be ligated to creates a unique sequence that may be individually tracked. As described herein, detection of non-unique barcodes in combination with sequence data of beginning (start) and end (stop) portions of sequence reads may allow assignment of a unique identity to a particular molecule. The length or number of base pairs, of an individual sequence read may also be used to assign a unique identity to such a molecule. As described herein, fragments from a single strand of nucleic acid having been assigned a unique identity, may thereby permit subsequent identification of fragments from the parent strand.

3. Amplification

Sample nucleic acids flanked by adapters can be amplified by PCR and other amplification methods. Amplification is typically primed by primers binding to primer binding sites in adapters flanking a DNA molecule to be amplified. Amplification methods can involve cycles of denaturation, annealing and extension, resulting from thermocycling or can be isothermal as in transcription-mediated amplification. Other amplification methods include the ligase chain reaction, strand displacement amplification, nucleic acid sequence-based amplification, and self-sustained sequence-based replication.

Preferably, the present methods perform dsDNA 'TV A ligations' with T-tailed and C-tailed adapters, which result in amplification of at least 50, 60, 70 or 80% of double stranded nucleic acids before linking to adapters. Preferably the present methods increase the amount or number of amplified molecules relative to control methods performed with T-tailed adapters alone by at least 10, 15 or 20%.

4. Bait Sets; Capture Moieties; Enrichment

As discussed above, nucleic acids in a sample can be subject to a capture step, in which molecules having target sequences are captured for subsequent analysis. Target capture can involve use of a bait set comprising oligonucleotide baits labeled with a capture moiety, such as biotin or the other examples noted below. The probes can have sequences selected to tile across a panel of regions, such as genes. In some embodiments, a bait set can have higher and lower capture yields for sets of target regions such as those of the sequence-variable target region set and the epigenetic target region set, respectively, as discussed elsewhere herein. Such bait sets are combined with a sample under conditions that allow hybridization of the target molecules with the baits. Then, captured molecules are isolated using the capture moiety. For example, a biotin capture moiety by bead-based streptavidin. Such methods are further described in, for example, U.S. Pat. No. 9,850,523, issuing Dec. 26, 2017, which is incorporated herein by reference.

Capture moieties include, without limitation, biotin, avidin, streptavidin, a nucleic acid comprising a particular nucleotide sequence, a hapten recognized by an antibody, and magnetically attractable particles. The extraction moiety can be a member of a binding pair, such as biotin/streptavidin or hapten/antibody. In some embodiments, a capture moiety that is attached to an analyte is captured by its binding pair which is attached to an isolatable moiety, such as a magnetically attractable particle or a large particle that can be sedimented through centrifugation. The capture moiety can be any type of molecule that allows affinity separation of nucleic acids bearing the capture moiety from nucleic acids lacking the capture moiety. Exemplary capture moieties are biotin which allows affinity separation by binding to streptavidin linked or linkable to a solid phase or an oligonucleotide, which allows affinity separation through binding to a complementary oligonucleotide linked or linkable to a solid phase.

5. Sequencing

Sample nucleic acids, optionally flanked by adapters, with or without prior amplification are generally subjected to sequencing. Sequencing methods or commercially available formats that are optionally utilized include, for example, Sanger sequencing, high-throughput sequencing, pyrose-quencing, sequencing-by-synthesis, single-molecule sequencing, nanopore-based sequencing, semiconductor sequencing, sequencing-by-ligation, sequencing-by-hybridization, RNA-Seq (Illumina), Digital Gene Expression (Helicos), next generation sequencing (NGS), Single Molecule Sequencing by Synthesis (SMSS) (Helicos), massively-parallel sequencing, Clonal Single Molecule Array (Solexa), shotgun sequencing, Ion Torrent, Oxford Nanopore, Roche Genia, Maxim-Gilbert sequencing, primer walking, sequencing using PacBio, SOLiD, Ion Torrent, or Nanopore platforms. Sequencing reactions can be performed in a variety of sample processing units, which may include multiple lanes, multiple channels, multiple wells, or other means of processing multiple sample sets substantially simultaneously. Sample processing units can also include multiple sample chambers to enable the processing of multiple runs simultaneously.

The sequencing reactions can be performed on one or more nucleic acid fragment types or regions containing markers of cancer or of other diseases. The sequencing reactions can also be performed on any nucleic acid fragment present in the sample. The sequence reactions may be performed on at least about 5%, 10%, 15%, 20%, 25%, 30%, 40%, 50%, 60%, 70%, 80%, 90%, 95%, 99%, 99.9%, or 100% of the genome. In other cases, sequence reactions may be performed on less than about 5%, 10%, 15%, 20%, 25%, 30%, 40%, 50%, 60%, 70%, 80%, 90%, 95%, 99%, 99.9%, or 100% of the genome.

Simultaneous sequencing reactions may be performed using multiplex sequencing techniques. In some embodiments, cell-free polynucleotides are sequenced with at least about 1000, 2000, 3000, 4000, 5000, 6000, 7000, 8000, 9000, 10000, 50000, or 100,000 sequencing reactions. In other embodiments, cell-free polynucleotides are sequenced with less than about 1000, 2000, 3000, 4000, 5000, 6000, 7000, 8000, 9000, 10000, 50000, or 100,000 sequencing reactions. Sequencing reactions are typically performed sequentially or simultaneously. Subsequent data analysis is generally performed on all or part of the sequencing reactions. In some embodiments, data analysis is performed on at least about 1000, 2000, 3000, 4000, 5000, 6000, 7000, 8000, 9000, 10000, 50000, or 100,000 sequencing reactions. In other embodiments, data analysis may be performed on less than about 1000, 2000, 3000, 4000, 5000, 6000, 7000, 8000, 9000, 10000, 50000, or 100,000 sequencing reactions. An example of a read depth is from about 1000 to about 50000 reads per locus (e.g., base position).

a. Differential Depth of Sequencing

In some embodiments, nucleic acids corresponding to the sequence-variable target region set are sequenced to a greater depth of sequencing than nucleic acids corresponding to the epigenetic target region set. For example, the depth of sequencing for nucleic acids corresponding to the sequence variant target region set may be at least 1.25-, 1.5-, 1.75-, 2-, 2.25-, 2.5-, 2.75-, 3-, 3.5-, 4-, 4.5-, 5-, 6-, 7-, 8-, 9-, 10-, 11-, 12-, 13-, 14-, or 15-fold greater, or 1.25- to 1.5-, 1.5- to 1.75-, 1.75- to 2-, 2- to 2.25-, 2.25- to 2.5-, 2.5- to 2.75-, 2.75- to 3-, 3- to 3.5-, 3.5- to 4-, 4- to 4.5-, 4.5- to 5-, 5- to 5.5-, 5.5- to 6-, 6- to 7-, 7- to 8-, 8- to 9-, 9- to 10-, 10- to 11-, 11- to 12-, 13- to 14-, 14- to 15-fold, or 15- to 100-fold greater, than the depth of sequencing for nucleic acids corresponding to the epigenetic target region set. In some embodiments, said depth of sequencing is at least 2-fold greater. In some embodiments, said depth of sequencing is at least 5-fold greater. In some embodiments, said depth of sequencing is at least 10-fold greater. In some embodiments, said depth of sequencing is 4- to 10-fold greater. In some embodiments, said depth of sequencing is 4- to 100-fold greater. Each of these embodiments refer to the extent to which nucleic acids corresponding to the sequence-variable target region set are sequenced to a greater depth of sequencing than nucleic acids corresponding to the epigenetic target region set.

In some embodiments, the captured cDNA corresponding to the sequence-variable target region set and the captured cfDNA corresponding to the epigenetic target region set are sequenced concurrently, e.g., in the same sequencing cell (such as the flow cell of an Illumina sequencer) and/or in the same composition, which may be a pooled composition resulting from recombining separately captured sets or a composition obtained by capturing the cfDNA corresponding to the sequence-variable target region set and the captured cfDNA corresponding to the epigenetic target region set in the same vessel.

6. Analysis

Sequencing may generate a plurality of sequence reads or reads. Sequence reads or reads may include sequences of nucleotide data less than about 150 bases in length, or less than about 90 bases in length. In some embodiments, reads are between about 80 bases and about 90 bases, e.g., about 85 bases in length. In some embodiments, methods of the present disclosure are applied to very short reads, e.g., less than about 50 bases or about 30 bases in length. Sequence read data can include the sequence data as well as meta information. Sequence read data can be stored in any suitable file format including, for example, VCF files, FASTA files, or FASTQ files.

FASTA may refer to a computer program for searching sequence databases, and the name FASTA may also refer to a standard file format. FASTA is described by, for example, Pearson & Lipman, 1988, Improved tools for biological sequence comparison, PNAS 85:2444-2448, which is hereby incorporated by reference in its entirety. A sequence in FASTA format begins with a single-line description, followed by lines of sequence data. The description line is distinguished from the sequence data by a greater-than (">") symbol in the first column. The word following the ">" symbol is the identifier of the sequence, and the rest of the line is the description (both are optional). There may be no space between the ">" and the first letter of the identifier. It is recommended that all lines of text be shorter than 80 characters. The sequence ends if another line starting with a ">" appears; this indicates the start of another sequence.

The FASTQ format is a text-based format for storing both a biological sequence (usually nucleotide sequence) and its corresponding quality scores. It is similar to the FASTA format but with quality scores following the sequence data. Both the sequence letter and quality score are encoded with a single ASCII character for brevity. The FASTQ format is a de facto standard for storing the output of high throughput sequencing instruments such as the Illumina Genome Analyzer, as described by, for example, Cock et al. ("The Sanger FASTQ file format for sequences with quality scores, and the Solexa/Illumina FASTQ variants," *Nucleic Acids Ras* 38(6):1767-1771, 2009), which is hereby incorporated by reference in its entirety.

For FASTA and FASTQ files, meta information includes the description line and not the lines of sequence data. In some embodiments, for FASTQ files, the meta information includes the quality scores. For FASTA and FASTQ files, the sequence data begins after the description line and is present typically using some subset of RUPAC ambiguity codes optionally with "-". In an embodiment, the sequence data may use the A, T, C, G, and N characters, optionally including "-" or U as-needed (e.g., to represent gaps or uracil).

In some embodiments, the at least one master sequence read file and the output file are stored as plain text files (e.g., using encoding such as ASCII; ISO/IEC 646; EBCDIC; UTF-8; or UTF-16). A computer system provided by the present disclosure may include a text editor program capable of opening the plain text files. A text editor program may refer to a computer program capable of presenting contents of a text file (such as a plain text file) on a computer screen, allowing a human to edit the text (e.g., using a monitor, keyboard, and mouse). Examples of text editors include, without limitation, Microsoft Word, emacs, pico, vi, BBEdit, and TextWrangler. The text editor program may be capable of displaying the plain text files on a computer screen, showing the meta information and the sequence reads in a human-readable format (e.g., not binary encoded but instead using alphanumeric characters as they may be used in print or human writing).

While methods have been discussed with reference to FASTA or FASTQ files, methods and systems of the present disclosure may be used to compress any suitable sequence file format including, for example, files in the Variant Call Format (VCF) format. A typical VCF file may include a header section and a data section. The header contains an arbitrary number of meta-information lines, each starting with characters '##', and a TAB delimited field definition line starting with a single '#' character. The field definition line names eight mandatory columns and the body section contains lines of data populating the columns defined by the field definition line. The VCF format is described by, for example, Danecek et al. ("The variant call format and VCF tools," *Bioinformatics* 27(15):2156-2158, 2011), which is hereby incorporated by reference in its entirety. The header section may be treated as the meta information to write to the compressed files and the data section may be treated as the lines, each of which can be stored in a master file only if unique.

Some embodiments provide for the assembly of sequence reads. In assembly by alignment, for example, the sequence reads are aligned to each other or aligned to a reference sequence. By aligning each read, in turn to a reference genome, all of the reads are positioned in relationship to each other to create the assembly. In addition, aligning or mapping the sequence read to a reference sequence can also be used to identify variant sequences within the sequence read. Identifying variant sequences an be used in combination with the methods and systems described herein to further aid in the diagnosis or prognosis of a disease or condition, or for guiding treatment decisions.

In some embodiments, any or all of the steps are automated. Alternatively, methods of the present disclosure may be embodied wholly or partially in one or more dedicated programs, for example, each optionally written in a compiled language such as C++, then compiled and distributed as a binary. Methods of the present disclosure may be implemented wholly or in part as modules within, or by invoking functionality within, existing sequence analysis platforms. In some embodiments, methods of the present disclosure include a number of steps that are all invoked automatically responsive to a single starting queue (e.g., one or a combination of triggering events sourced from human activity, another computer program, or a machine). Thus, the present disclosure provides methods in which any or the steps or any combination of the steps can occur automatically responsive to a queue. "Automatically" generally means without intervening human input, influence, or interaction (e.g., responsive only to original or pre-queue human activity).

The methods of the present disclosure may also encompass various forms of output, which includes an accurate and sensitive interpretation of a subject's nucleic acid sample. The output of retrieval can be provided in the format of a computer file. In some embodiments, the output is a FASTA file, a FASTQ file, or a VCF file. The output may be processed to produce a text file, or an XML file containing sequence data such as a sequence of the nucleic acid aligned to a sequence of the reference genome. In other embodiments, processing yields output containing coordinates or a string describing one or more mutations in the subject nucleic acid relative to the reference genome. Alignment strings may include Simple UnGapped Alignment Report (SUGAR), Verbose Useful Labeled Gapped Alignment Report (VULGAR), and Compact Idiosyncratic Gapped Alignment Report (CIGAR) (as described by, for example, Ning et al., *Genome Research* 11(10):1725-9, 2001, which is hereby incorporated by reference in its entirety). These strings may be implemented, for example, in the Exonerate sequence alignment software from the European Bioinformatics Institute (Hinxton, UK).

In some embodiments, a sequence alignment is produced—such as, for example, a sequence alignment map (SAM) or binary alignment map (BAM) file—comprising a CIGAR string (the SAM format is described, e.g., by Li et al., "The Sequence Alignment/Map format and SAMtools," *Bioinformatics,* 25(16):2078-9, 2009, which is hereby incorporated by reference in its entirety). In some embodiments, CIGAR displays or includes gapped alignments one-per-line. CIGAR is a compressed pairwise alignment format reported as a CIGAR string. A CIGAR string may be useful for representing long (e.g., genomic) pairwise alignments. A CIGAR string may be used in SAM format to represent alignments of reads to a reference genome sequence.

A CIGAR string may follow an established motif. Each character is preceded by a number, giving the base counts of the event. Characters used can include M, I, D, N, and S (M=match; I=insertion; D=deletion; N=gap; S=substitution). The CIGAR string defines the sequence of matches and/or mismatches and deletions (or gaps). For example, the CIGAR string 2MD3M2D2M may indicate that the alignment contains 2 matches, 1 deletion (number 1 is omitted in order to save some space), 3 matches, 2 deletions, and 2 matches.

In some embodiments, a nucleic acid population is prepared for sequencing by enzymatically forming blunt-ends on double-stranded nucleic acids with single-stranded overhangs at one or both ends. In these embodiments, the population is typically treated with an enzyme having a 5'-3' DNA polymerase activity and a 3'-5' exonuclease activity in the presence of the nucleotides (e.g., A, C, G, and T or U). Examples of enzymes or catalytic fragments thereof that may be optionally used include Klenow large fragment and T4 polymerase. At 5' overhangs, the enzyme typically extends the recessed 3' end on the opposing strand until it is flush with the 5' end to produce a blunt end. At 3' overhangs, the enzyme generally digests from the 3' end up to and sometimes beyond the 5' end of the opposing strand. If this digestion proceeds beyond the 5' end of the opposing strand, the gap can be filled in by an enzyme having the same polymerase activity that is used for 5' overhangs. The formation of blunt ends on double-stranded nucleic acids facilitates, for example, the attachment of adapters and subsequent amplification.

In some embodiments, nucleic acid populations are subjected to additional processing, such as the conversion of sig-stranded nucleic acids to double-stranded nucleic acids and/or conversion of RNA to DNA (e.g., complementary DNA or cDNA). These forms of nucleic acid are also optionally linked to adapters and amplified.

With or without prior amplification, nucleic acids subject to the process of forming blunt-ends described above, and optionally other nucleic acids in a sample, can be sequenced to produce sequenced nucleic acids. A sequenced nucleic acid can refer either to the sequence of a nucleic acid (e.g., sequence information) or a nucleic acid whose sequence has been determined. Sequencing can be performed so as to provide sequence data of individual nucleic acid molecules in a sample either directly or indirectly from a consensus sequence of amplification products of an individual nucleic acid molecule in the sample.

In some embodiments, double-stranded nucleic acids with single-stranded overhangs in a sample after blunt-end formation are linked at both ends to adapters including barcodes, and the sequencing determines nucleic acid sequences as well as in-line barcodes introduced by the adapters. The blunt-end DNA molecules are optionally ligated to a blunt end of an at least partially double-stranded adapter (e.g., a Y-shaped or bell-shaped adapter). Alternatively, blunt ends of sample nucleic acids and adapters can be tailed with complementary nucleotides to facilitate ligation (for e.g., sticky-end ligation).

The nucleic acid sample is typically contacted with a sufficient number of adapters that there is a low probability (e.g., less than about 1 or 0.1%) that any two copies of the same nucleic acid receive the same combination of adapter barcodes from the adapters linked at both ends. The use of adapters in this manner may permit identification of families of nucleic acid sequences with the same start and stop points on a reference nucleic acid and linked to the same combination of barcodes. Such a family may represent sequences of amplification products of a nucleic acid in the sample before amplification. The sequences of family members can be compiled to derive consensus nucleotide(s) or a complete consensus sequence for a nucleic acid molecule in the original sample, as modified by blunt-end formation and adapter attachment. In other words, the nucleotide occupying a specified position of a nucleic acid in the sample can be determined to be the consensus of nucleotides occupying that corresponding position in family member sequences. Families can include sequences of one or both strands of a double-stranded nucleic acid. If members of a family include sequences of both strands from a double-stranded nucleic acid, sequences of one strand may be converted to their complements for purposes of compiling sequences to derive consensus nucleotide(s) or sequences. Some families include only a single member sequence. In this case, this sequence can be taken as the sequence of a nucleic acid in the sample before amplification. Alternatively, families with only a single member sequence can be eliminated from subsequent analysis.

Nucleotide variations (e.g., SNVs or indels) in sequenced nucleic acids can be determined by comparing sequenced nucleic acids with a reference sequence. The reference sequence is often a known sequence, e.g., a known whole or partial genome sequence from a subject (e.g., a whole genome sequence of a human subject). The reference sequence can be, for example, hG19 or hG38. The sequenced nucleic acids can represent sequences determined directly for a nucleic acid in a sample, or a consensus of sequences of amplification products of such a nucleic acid, as described above. A comparison can be performed at one or more designated positions on a reference sequence. A subset of sequenced nucleic acids can be identified including a position corresponding with a designated position of the reference sequence when the respective sequences are maximally aligned. Within such a subset it can be determined which, if any, sequenced nucleic acids include a nucleotide variation at the designated position, and optionally which if any, include a reference nucleotide (e.g., same as in the reference sequence). If the number of sequenced nucleic acids in the subset including a nucleotide variant exceeding a selected threshold, then a variant nucleotide can be called at the designated position. The threshold can be a simple number, such as at least 1, 2, 3, 4, 5, 6, 7, 8, 9, or 10 sequenced nucleic acids within the subset including the nucleotide variant or it can be a ratio, such as at least 0.5, 1, 2, 3, 4, 5, 10, 15, or 20, of sequenced nucleic acids within the subset that include the nucleotide variant, among other possibilities. The comparison can be repeated for any designated position of interest in the reference sequence. Sometimes a comparison can be performed for designated positions occupying at least about 20, 100, 200, or 300 contiguous positions on a reference sequence, e.g., about 20-500, or about 50-300 contiguous positions.

Additional details regarding nucleic acid sequencing, including the formats and applications described herein, are also provided in, for example, Levy et al., Annual Review of Genomics and Human Genetics, 17: 95-115 (2016). Liu et al., J. of Biomedicine and Biotechnology, Volume 2012, Article ID 251364:1-11 (2012). Voelkerding et al., Clinical Chem., 55: 641-658 (2009). MacLean et al., Nature Rev. Microbiol., 7: 287-296 (2009), Astier et al., J Am Chem Soc., 128(5):1705-10 (2006). U.S. Pat. Nos. 6,210,891, 6,258,568, 6,833,246, 7,115,400, 6,969,488, 5,912,148, 6,130,073, 7,169,560, 7,282,337, 7,482,120, 7,501,245, 6,818,395, 6,911,345, 7,501,245, 7,329,492, 7,170,050, 7,302,146, 7,313,308, and 7,476,503, each of which is hereby incorporated by reference in its entirety.

IV. Collections of Target-Specific Probes; Compositions

1. Collections of Target-Specific Probes

In some embodiments, a collection of target-specific probes is provided, which comprises target-binding probes specific for a sequence-variable target region set and target-binding probes specific for an epigenetic target region set. In some embodiments, the capture yield of the target-binding probes specific for the sequence-variable target region set is higher (e.g., at least 2-fold higher) than the capture yield of the target-binding probes specific for the epigenetic target region set. In some embodiments, the collection of target-specific probes is configured to have a capture yield specific for the sequence-variable target region set higher (e.g., at least 2-fold higher) than its capture yield specific for the epigenetic target region set.

In some embodiments, the capture yield of the target-binding probes specific for the sequence-variable target region set is at least 1.25-, 1.5-, 1.75-, 2-, 2.25-, 2.5-, 2.75-, 3-, 3.5-, 4-, 4.5-, 5-, 6-, 7-, 8-, 9-, 10-, 11-, 12-, 13-, 14-, or 15-fold higher than the capture yield of the target-binding probes specific for the epigenetic target region set. In some embodiments, the capture yield of the target-binding probes specific for the sequence-variable target region set is 1.25- to 1.5-, 1.5- to 1.75-, 1.75- to 2-, 2- to 2.25-, 2.25- to 2.5-, 2.5- to 2.75-, 2.75- to 3-, 3- to 3.5-, 3.5- to 4-, 4- to 4.5-, 4.5- to 5-, 5- to 5.5-, 5.5- to 6-, 6- to 7-, 7- to 8-, 8- to 9-, 9- to 10-, 10- to 11-, 11- to 12-, 13- to 14-, or 14- to 15-fold higher than the capture yield of the target-binding probes specific for the epigenetic target region set. In some embodiments, the capture yield of the target-binding probes specific for the sequence-variable target region set is at least 10-fold higher than the capture yield of the target-binding probes specific for the epigenetic target region set, e.g., 10- to 20-fold higher than the capture yield of the target-binding probes specific for the epigenetic target region set.

In some embodiments, the collection of target-specific probes is configured to have a capture yield specific for the sequence-variable target region set at least 1.25-, 1.5-, 1.75-, 2-, 2.25-, 2.5-, 2.75-, 3-, 3.5-, 4-, 4.5-, 5-, 6-, 7-, 8-, 9-, 10-, 11-, 12-, 13-, 14-, or 15-fold higher than its capture yield for the epigenetic target region set. In some embodiments, the collection of target-specific probes is configured to have a capture yield specific for the sequence-variable target region set is 1.25- to 1.5-, 1.5- to 1.75-, 1.75- to 2-, 2- to 2.25-, 2.25- to 2.5-, 2.5- to 2.75-, 2.75- to 3-, 3- to 3.5-, 3.5- to 4-, 4- to 4.5-, 4.5- to 5-, 5- to 5.5-, 5.5- to 6-, 6- to 7-, 7- to 8-, 8- to 9-, 9- to 10-, 10- to 11-, 1- to 12-, 13- to 14-, or 14- to 15-fold higher than its capture yield specific for the epigenetic target region set. In some embodiments, the collection of target-specific probes is configured to have a capture yield specific for the sequence-variable target region set at least 10-fold higher than its capture yield for the epigenetic target region set, e.g., 10- to 20-fold higher than its capture yield for the epigenetic target region set.

The collection of probes can be configured to provide higher capture yields for the sequence-variable target region set in various ways, including concentration, different lengths and/or chemistries (e.g., that affect affinity), and combinations thereof. Affinity can be modulated by adjusting probe length and/or including nucleotide modifications as discussed below.

In some embodiments, the target-specific probes specific for the sequence-variable target region set are present at a higher concentration than the target-specific probes specific for the epigenetic target region set. In some embodiments, the concentration of the target-binding probes specific for the sequence-variable target region set is at least 1.25-, 1.5-, 1.75-, 2-, 2.25-, 2.5-, 2.75-, 3-, 3.5-, 4-, 4.5-, 5-, 6-, 7-, 8-, 9-, 10-, 11-, 12-, 13-, 14-, or 15-fold higher than the concentration of the target-binding probes specific for the epigenetic target region set. In some embodiments, the concentration of the target-binding probes specific for the sequence-variable target region set is 1.25- to 1.5-, 1.5- to 1.75-, 1.75- to 2-, 2- to 2.25-, 2.25- to 2.5-, 2.5- to 2.75-, 2.75- to 3-, 3- to 3.5-, 3.5- to 4-, 4- to 4.5-, 4.5- to 5-, 5- to 5.5-, 5.5- to 6-, 6- to 7-, 7- to 8-, 8- to 9-, 9- to 10-, 10- to 11-, 1- to 12-, 13- to 14-, or 14- to 15-fold higher than the concentration of the target-binding probes specific for the epigenetic target region set. In some embodiments, the concentration of the target-binding probes specific for the sequence-variable target region set is at least 2-fold higher than the concentration of the target-binding probes specific for the epigenetic target region set. In some embodiments, the concentration of the target-binding probes specific for the sequence-variable target region set is at least 10-fold higher than the concentration of the target-binding probes specific for the epigenetic target region set, e.g., 10- to 20-fold higher than the concentration of the target-binding probes specific for the epigenetic target region set. In such embodiments, concentration may refer to the average mass per volume concentration of individual probes in each set.

In some embodiments, the target-specific probes specific for the sequence-variable target region set have a higher affinity for their targets than the target-specific probes specific for the epigenetic target region set. Affinity can be modulated in any way known to those skilled in the art, including by using different probe chemistries. For example, certain nucleotide modifications, such as cytosine 5-methylation (in certain sequence contexts), modifications that provide a heteroatom at the 2' sugar position, and LNA nucleotides, can increase stability of double-stranded nucleic acids, indicating that oligonucleotides with such modifications have relatively higher affinity for their complementary sequences. See, e.g., Severin et al., Nucleic Acids Res. 39: 8740-8751 (2011); Freier et al., Nucleic Acids Res. 25: 4429-4443 (1997); U.S. Pat. No. 9,738,894. Also, longer sequence lengths will generally provide increased affinity. Other nucleotide modifications, such as the substitution of the nucleobase hypoxanthine for guanine, reduce affinity by reducing the amount of hydrogen bonding between the oligonucleotide and its complementary sequence. In some embodiments, the target-specific probes specific for the sequence-variable target region set have modifications that increase their affinity for their targets. In some embodiments, alternatively or additionally, the target-specific probes specific for the epigenetic target region set have modifications that decrease their affinity for their targets. In some embodiments, the target-specific probes specific for the sequence-variable target region set have longer average lengths and/or higher average melting temperatures than the target-specific probes specific for the epigenetic target region set. These embodiments may be combined with each other and/or with differences in concentration as discussed above to achieve a desired fold difference in capture yield, such as any fold difference or range thereof described above.

In some embodiments, the target-specific probes comprise a capture moiety. The capture moiety may be any of the capture moieties described herein, e.g., biotin. In some embodiments, the target-specific probes are linked to a solid support, e.g., covalently or non-covalently such as through the interaction of a binding pair of capture moieties. In some embodiments, the solid support is a bead, such as a magnetic bead.

In some embodiments, the target-specific probes specific for the sequence-variable target region set and/or the target-specific probes specific for the epigenetic target region set are a bait set as discussed above, e.g., probes comprising capture moieties and sequences selected to tile across a panel of regions, such as genes.

In some embodiments, the target-specific probes are provided in a single composition. The single composition may be a solution (liquid or frozen). Alternatively, it may be a lyophilizate.

Alternatively, the target-specific probes may be provided as a plurality of compositions. e.g., comprising a first composition comprising probes specific for the epigenetic target region set and a second composition comprising probes specific for the sequence-variable target region set. These probes may be mixed in appropriate proportions to provide a combined probe composition with any of the foregoing fold differences in concentration and/or capture yield. Alternatively, they may be used in separate capture procedures (e.g., with aliquots of a sample or sequentially with the same sample) to provide first and second compositions comprising captured epigenetic target regions and sequence-variable target regions, respectively.

a. Probes Specific for Epigenetic Target Regions

The probes for the epigenetic target region set may comprise probes specific for one or more types of target regions likely to differentiate DNA from neoplastic (e.g., tumor or cancer) cells from healthy cells, e.g., non-neoplastic circulating cells. Exemplary types of such regions are discussed in detail herein, e.g., in the sections above concerning captured sets. The probes for the epigenetic target region set may also comprise probes for one or more control regions, e.g., as described herein.

In some embodiments, the probes for the epigenetic target region probe set have a footprint of at least 100 kb, e.g., at least 200 kb, at least 300 kb, or at least 400 kb. In some embodiments, the probes for the epigenetic target region set have a footprint in the range of 100-1000 kb, e.g., 100-200 kb, 200-300 kb, 300-400 kb, 400-500 kb, 500-600 kb, 600-700 kb, 700-800 kb, 800-900 kb, and 900-1,000 kb.

i. Hypermethylation Variable Target Regions

In some embodiments, the probes for the epigenetic target region set comprise probes specific for one or more hypermethylation variable target regions. The hypermethylation variable target regions may be any of those set forth above. For example, in some embodiments, the probes specific for hypermethylation variable target regions comprise probes specific for a plurality of loci listed in Table 1, e.g., at least 10%, 20%, 30%, 40%, 50%, 60%, 70%, 80%, 90%, or 100% of the loci listed in Table 1. In some embodiments, the probes specific for hypermethylation variable target regions comprise probes specific for a plurality of loci listed in Table 2, e.g., at least 10%, 20%, 30%, 40%, 50%, 60%, 70%, 80%, 90%, or 100% of the loci listed in Table 2. In some embodiments, the probes specific for hypermethylation variable target regions comprise probes specific for a plurality of loci listed in Table 1 or Table 2, e.g., at least 10%, 20%, 30%, 40%, 50%, 60%, 70%, 80%, 90%, or 100% of the loci listed in Table 1 or Table 2. In some embodiments, for each locus included as a target region, there may be one or more probes with a hybridization site that binds between the transcription start site and the stop codon (the last stop codon for genes that are alternatively spliced) of the gene. In some embodiments, the one or more probes bind within 300 bp of the listed position, e.g., within 200 or 100 bp. In some embodiments, a probe has a hybridization site overlapping the position listed above. In some embodiments, the probes specific for the hypermethylation target regions include probes specific for one, two, three, four, or five subsets of hypermethylation target regions that collectively show hypermethylation in one, two, three, four, or five of breast, colon, kidney, liver, and lung cancers.

ii. Hypermethylation Variable Target Regions

In some embodiments, the probes for the epigenetic target region set comprise probes specific for one or more hypomethylation variable target regions. The hypomethylation variable target regions may be any of those set forth above. For example, the probes specific for one or more hypomethylation variable target regions may include probes for regions such as repeated elements, e.g., LINE1 elements, Alu elements, centromeric tandem repeats, pericentromeric tandem repeats, and satellite DNA, and intergenic regions that are ordinarily methylated in healthy cells may show reduced methylation in tumor cells.

In some embodiments, probes specific for hypomethylation variable target regions include probes specific for repeated elements and/or intergenic regions. In some embodiments, probes specific for repeated elements include probes specific for one, two, three, four, or five of LINE1 elements, Alu elements, centromeric tandem repeats, pericentromeric tandem repeats, and/or satellite DNA.

Exemplary probes specific for genomic regions that show cancer-associated hypomethylation include probes specific for nucleotides 8403565-8953708 and/or 151104701-151106035 of human chromosome 1. In some embodiments, the probes specific for hypomethylation variable target regions include probes specific for regions overlapping or comprising nucleotides 8403565-8953708 and/or 151104701-151106035 of human chromosome 1.

iii. CTCF Blinding Regions

In some embodiments, the probes for the epigenetic target region set include probes specific for CTCF binding regions. In some embodiments, the probes specific for CTCF binding regions comprise probes specific for at least 10, 20, 50, 100, 200, or 500 CTCF binding regions, or 10-20, 20-50, 50-100, 100-200, 200-500, or 500-1000 CTCF binding regions, e.g., such as CTCF binding regions described above or in one or more of CTCFBSDB or the Cuddapah et al., Martin et al., or Rhee et al. articles cited above. In some embodiments, the probes for the epigenetic target region set comprise at least 100 bp, at least 200 bp at least 300 bp, at least 400 bp, at least 500 bp, at least 750 bp, or at least 1000 bp upstream and downstream regions of the CTCF binding sites.

iv. Transcription Start Sites

In some embodiments, the probes for the epigenetic target region set include probes specific for transcriptional start sites. In some embodiments, the probes specific for transcriptional start sites comprise probes specific for at least 10, 20, 50, 100, 200, or 500 transcriptional start sites, or 10-20, 20-50, 50-100, 100-200, 200-500, or 500-1000 transcriptional start sites, e.g., such as transcriptional start sites listed in DBTSS. In some embodiments, the probes for the epigenetic target region set comprise probes for sequences at least 100 hp, at least 200 hp, at least 300 hp, at least 400 hp, at least 500 hp, at least 750 bp, or at least 1000 bp upstream and downstream of the transcriptional start sites.

v. Focal Amplifications

As noted above, although focal amplifications are somatic mutations, they can be detected by sequencing based on read frequency in a manner analogous to approaches for detecting certain epigenetic changes such as changes in methylation. As such, regions that may show focal amplifications in cancer can be included in the epigenetic target region set, as discussed above. In some embodiments, the probes specific for the epigenetic target region set include probes specific for focal amplifications. In some embodiments, the probes specific for focal amplifications include probes specific for one or more of AR, BRAF, CCND1, CCND2, CCNE1, CDK4, CDK6, EGFR, ERBB2, FGFR1, FGFR2, KIT, KRAS, MET, MYC, PDGFRA, PIK3CA, and RAF1. For example, in some embodiments, the probes specific for focal amplifications include probes specific for one or more of at least 2, 3, 4, 5, 6, 7, 8, 9, 10, 11, 12, 13, 14, 15, 16, 17, or 18 of the foregoing targets.

vi. Control Regions

It can be useful to include control regions to facilitate data validation. In some embodiments, the probes specific for the epigenetic target region set include probes specific for control methylated regions that are expected to be methylated in essentially all samples. In some embodiments, the probes specific for the epigenetic target region set include probes specific for control hypomethylated regions that are expected to be hypomethylated in essentially all samples.

b. Probes Specific for Sequence-Variable Target Regions

The probes for the sequence-variable target region set may comprise probes specific for a plurality of regions known to undergo somatic mutations in cancer. The probes may be specific for any sequence-variable target region set described herein. Exemplary sequence-variable target region sets are discussed in detail herein, e.g., in the sections above concerning captured sets.

In some embodiments, the sequence-variable target region probe set has a footprint of at least 10 kb, e.g., at least 20 kb, at least 30 kb, or at least 40 kb. In some embodiments, the epigenetic target region probe set has a footprint in the range of 10-100 kb, e.g., 10-20 kb, 20-30 kb, 30-40 kb, 40-50 kb, 50-60 kb, 60-70 kb, 70-80 kb, 80-90 kb, and 90-100 kb.

In some embodiments, probes specific for the sequence-variable target region set comprise probes specific for at least a portion of at least 5, at least 10, at least 15, at least 20, at least 25, at least 30, at least 35, at least 40, at least 45, at least 50, at least 55, at least 60, at least 65, or 70 of the genes of Table 3. In some embodiments, probes specific for the sequence-variable target region set comprise probes specific for the at least 5, at least 10, at least 15, at least 20, at least 25, at least 30, at least 35, at least 40, at least 45, at least 50, at least 55, at least 60, at least 65, or 70 of the SNVs of Table 3. In some embodiments, probes specific for the sequence-variable target region set comprise probes specific for at least 1, at least 2, at least 3, at least 4, at least 5, or 6 of the fusions of Table 3. In some embodiments, probes specific for the sequence-variable target region set comprise probes specific for at least a portion of at least 1, at least 2, or 3 of the indels of Table 3. In some embodiments, probes specific for the sequence-variable target region set comprise probes specific for at least a portion of at least 5, at least 10, at least 15, at least 20, at least 25, at least 30, at least 35, at least 40, at least 45, at least 50, at least 55, at least 60, at least 65, at least 70, or 73 of the genes of Table 4. In some embodiments, probes specific for the sequence-variable target region set comprise probes specific for at least 5, at least 10, at least 15, at least 20, at least 25, at least 30, at least 35, at least 40, at least 45, at least 50, at least 55, at least 60, at least 65, at least 70, or 73 of the SNVs of Table 4. In some embodiments, probes specific for the sequence-variable target region set comprise probes specific for at least 1, at least 2, at least 3, at least 4, at least 5, or 6 of the fusions of Table 4. In some embodiments, probes specific for the sequence-variable target region set comprise probes specific for at least a portion of at least 1, at least 2, at least 3, at least 4, at least 5, at least 6, at least 7, at least 8, at least 9, at least 10, at least 11, at least 12, at least 13, at least 14, at least 15, at least 16, at least 17, or 18 of the indels of Table 4. In some embodiments, probes specific for the sequence-variable target region set comprise probes specific for at least a portion of at least 1, at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, or at least 20 of the genes of Table 5.

In some embodiments, the probes specific for the sequence-variable target region set comprise probes specific for target regions from at least 10, 20, 30, or 35 cancer-related genes, such as AKT1, ALK, BRAF, CCND1, CDK2A, CTNNB1, EGFR, ERBB2, ESR1, FGFR1, FGFR2, FGFR3, FOXL2, GATA3, GNAI1, GNAQ, GNAS, HRAS, IDH1, IDH2, KIT, KRAS, MED12, MET, MYC, NFE2L2, NRAS, PDGFRA, PIK3CA, PPP2R1A, PTEN, RET, STK11, TP53, and U2AF1.

c. Competitions of Probes

In some embodiments, a single composition is provided comprising probes for the sequence-variable target region set and probes for the epigenetic target region set. The probes may be provided in such a composition at any concentration ratio described herein.

In some embodiments, a first composition comprising probes for the epigenetic target region set and a second composition comprising probes for the sequence-variable target region set are provided. The ratio of the concentration of the probes in the first composition to the concentration of the probes in the second composition may be any of the ratios described herein.

2. Compostions Comprising Captured cfDNA

In some embodiments, compositions comprising captured cfDNA are provided. The captured cfDNA may have any of the features described herein concerning captured sets, including, e.g., a greater concentration of the DNA corresponding to the sequence-variable target region set (normalized for footprint size as discussed above) than of the DNA corresponding to the epigenetic target region set. In some embodiments, the cfDNA of the captured set comprises sequence tags, which may be added to the cfDNA as described herein. In general, the inclusion of sequence tags results in the cfDNA molecules differing from their naturally occurring, untagged form.

Such compositions may further comprise a probe set described herein or sequencing primers, each of which may differ from naturally occurring nucleic acid molecules. For example, a probe set described herein may comprise a capture moiety, and sequencing primers may comprise a non-naturally occurring label.

V. Computer Systems

Methods of the present disclosure can be implemented using, or with the aid of, computer systems. For example, such methods, which may comprise: collecting cfDNA from a test subject; capturing a plurality of sets of target regions from the cfDNA, wherein the plurality of target region sets comprises a sequence-variable target region set and an epigenetic target region set, whereby a captured set of cfDNA molecules is produced; sequencing the captured cfDNA molecules, wherein the captured cfDNA molecules of the sequence-variable target region set are sequenced to a greater depth of sequencing than the captured cfDNA molecules of the epigenetic target region set; obtaining a plurality of sequence reads generated by a nucleic acid sequencer from sequencing the captured cfDNA molecules; mapping the plurality of sequence reads to one or more reference sequences to generate mapped sequence reads; and processing the mapped sequence reads corresponding to the sequence-variable target region set and to the epigenetic target region set to determine the likelihood that the subject has cancer.

Figure 2:
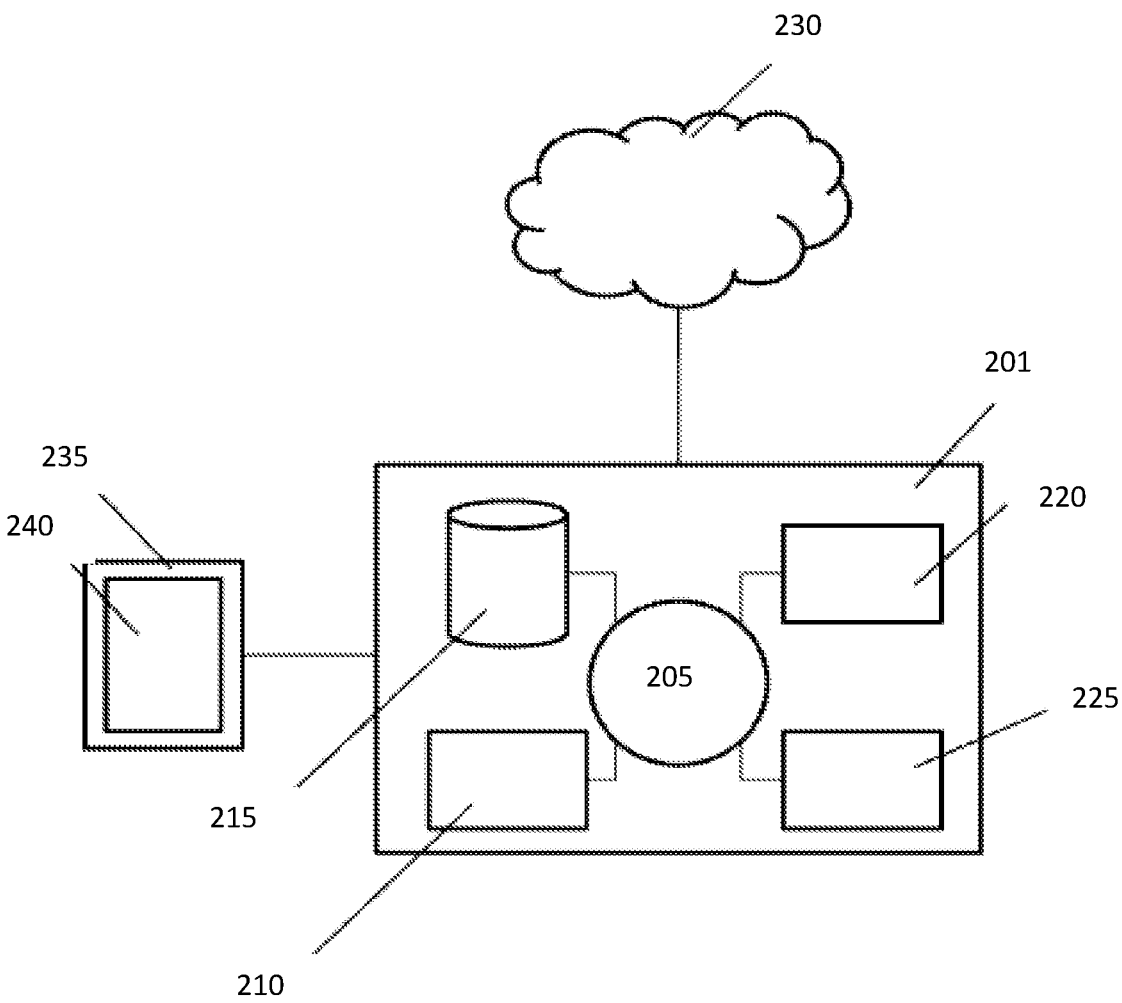
FIG. 2 is a schematic diagram of an example of a system suitable for use with some embodiments of the disclosure.

FIG. 2 shows a computer system 201 that is programmed or otherwise configured to implement the methods of the present disclosure. The computer system 201 can regulate various aspects sample preparation, sequencing, and/or analysis. In some examples, the computer system 201 is configured to perform sample preparation and sample analysis, including nucleic acid sequencing.

The computer system 201 includes a central processing unit (CPU, also "processor" and "computer processor" herein) 205, which can be a single core or multi core processor, or a plurality of processors for parallel processing. The computer system 201 also includes memory or memory location 210 (e.g., random-access memory, read-only memory, flash memory), electronic storage unit 215 (e.g., hard disk), communication interface 220 (e.g., network adapter) for communicating with one or more other systems, and peripheral devices 225, such as cache, other memory, data storage, and/or electronic display adapters. The memory 210, storage unit 215, interface 220, and peripheral devices 225 are in communication with the CPU 205 through a communication network or bus (solid lines), such as a motherboard. The storage unit 215 can be a data storage unit (or data repository) for storing data. The computer system 201 can be operatively coupled to a computer network 230 with the aid of the communication interface 220. The computer network 230 can be the Internet, an internet and/or extranet, or an intranet and/or extranet that is in communication with the Internet. The computer network 230 in some cases is a telecommunication and/or data network. The computer network 230 can include one or more computer servers, which can enable distributed computing, such as cloud computing. The computer network 230, in some cases with the aid of the computer system 201, can implement a peer-to-peer network, which may enable devices coupled to the computer system 201 to behave as a client or a server.

The CPU 205 can execute a sequence of machine-readable instructions, which can be embodied in a program or software. The instructions may be stored in a memory location, such as the memory 210. Examples of operations performed by the CPU 205 can include fetch, decode, execute, and writeback.

The storage unit 215 can store files, such as drivers, libraries, and saved programs. The storage unit 215 can store programs generated by users and recorded sessions, as well as output(s) associated with the programs. The storage unit 215 can store user data, e.g., user preferences and user programs. The computer system 201 in some cases can include one or more additional data storage units that are external to the computer system 201, such as located on a remote server that is in communication with the computer system 201 through an intranet or the Internet. Data may be transferred from one location to another using, for example, a communication network or physical data transfer (e.g., using a hard drive, thumb drive, or other data storage mechanism).

The computer system 201 can communicate with one or more remote computer systems through the network 230. For embodiment, the computer system 201 can communicate with a remote computer system of a user (e.g., operator). Examples of remote computer systems include personal computers (e.g., portable PC), slate or tablet PC's (e.g., Apple® iPad, Samsung® Galaxy Tab), telephones, Smart phones (e.g., Apple® iPhone, Android-enabled device, Blackberry®), or personal digital assistants. The user can access the computer system 201 via the network 230.

Methods as described herein can be implemented by way of machine (e.g., computer processor) executable code stored on an electronic storage location of the computer system 201, such as, for example, on the memory 210 or electronic storage unit 215. The machine executable or machine-readable code can be provided in the form of software. During use, the code can be executed by the processor 205. In some cases, the code can be retrieved from the storage unit 215 and stored on the memory 210 for ready access by the processor 205. In some situations, the electronic storage unit 215 can be precluded, and machine-executable instructions are stored on memory 210.

In an aspect, the present disclosure provides a non-transitory computer-readable medium comprising computer-executable instructions which, when executed by at least one electronic processor, perform at least a portion of a method comprising: collecting cfDNA from a test subject; capturing a plurality of sets of target regions from the cfDNA, wherein the plurality of target region sets comprises a sequence-variable target region set and an epigenetic target region set, whereby a captured set of cfDNA molecules is produced; sequencing the captured cfDNA molecules, wherein the captured cfDNA molecules of the sequence-variable target region set are sequenced to a greater depth of sequencing than the captured cfDNA molecules of the epigenetic target region set; obtaining a plurality of sequence reads generated by a nucleic acid sequencer from sequencing the captured cfDNA molecules; mapping the plurality of sequence reads to one or more reference sequences to generate mapped sequence reads; and processing the mapped sequence reads corresponding to the sequence-variable target region set and to the epigenetic target region set to determine the likelihood that the subject has cancer.

The code can be pre-compiled and configured for use with a machine have a processer adopted to execute the code or can be compiled during runtime. The code can be supplied in a programming language that can be selected to enable the code to execute in a pre-compiled or as-compiled fashion.

Aspects of the systems and methods provided herein, such as the computer system 201, can be embodied in programming. Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such memory (e.g., read-only memory, random-access memory, flash memory) or a hard disk. "Storage" type media can include any or all of the tangible memory of the computers, processors or the like, or associated modules thereof, such as various semi-conductor memories, tape drives, disk drives and the like, which may provide non-transitory storage at any time for the software programming.

All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical, and electromagnetic waves, such as those used across physical interfaces between local devices, through wired and optical landline networks, and over various air-links. The physical elements that carry such waves, such as wired or wireless links, optical links, or the like, also may be considered as media bearing the software. As used herein, unless restricted to non-transitory, tangible "storage" media, terms such as computer or machine "readable medium" refer to any medium that participates in providing instructions to a processor for execution.

Hence, a machine-readable medium, such as computer-executable code, may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards, paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

The computer system 201 can include or be in communication with an electronic display that comprises a user interface (UI) for providing, for example, one or more results of sample analysis. Examples of UIs include, without limitation, a graphical user interface (GUI) and web-based user interface.

Additional details relating to computer systems and networks, databases, and computer program products are also provided in, for example. Peterson, *Computer Networks: A Systems Approach*, Morgan Kaufmann, 5th Ed. (2011). Kurose, *Computer Networking: A Top-Down Approach*, Pearson, $7^{th}$ Ed. (2016). Elmasri, *Fundamentals of Database Systems*, Addison Wesley, 6th Ed. (2010). Coronel, *Database Systems: Design, Implementation, & Management*, Cengage Learning, $11^{th}$ Ed. (2014). Tucker, *Programming Languages*, McGraw-Hill Science/Engineering/Math, 2nd Ed. (2006), and Rhoton, *Cloud Computing Architected: Solution Design Handbook*, Recursive Press (2011), each of which is hereby incorporated by reference in its entirety.

VI. Applications

1. Cancer and Other Diseases

The present methods can be used to diagnose presence of conditions, particularly cancer, in a subject, to characterize conditions (e.g., staging cancer or determining heterogeneity of a cancer), monitor response to treatment of a condition, effect prognosis risk of developing a condition or subsequent course of a condition. The present disclosure can also be useful in determining the efficacy of a particular treatment option. Successful treatment options may increase the amount of copy number variation or rare mutations detected in subject's blood if the treatment is successful as more cancers may die and shed DNA. In other examples, this may not occur. In another example, perhaps certain treatment options may be correlated with genetic profiles of cancers over time. This correlation may be useful in selecting a therapy.

Additionally, if a cancer is observed to be in remission after treatment, the present methods can be used to monitor residual disease or recurrence of disease.

In some embodiments, the methods and systems disclosed herein may be used to identify customized or targeted therapies to treat a given disease or condition in patients based on the classification of a nucleic acid variant as being of somatic or germline origin. Typically, the disease under consideration is a type of cancer. Non-limiting examples of such cancers include biliary tract cancer, bladder cancer, transitional cell carcinoma, urothelial carcinoma, brain cancer, gliomas, astrocytomas, breast carcinoma, metaplastic carcinoma, cervical cancer, cervical squamous cell carcinoma, rectal cancer, colorectal carcinoma, colon cancer, hereditary nonpolyposis colorectal cancer, colorectal adenocarcinomas, gastrointestinal stromal tumors (GISTs), endometrial carcinoma, endometrial stromal sarcomas, esophageal cancer, esophageal squamous cell carcinoma, esophageal adenocarcinoma, ocular melanoma, uveal melanoma, gallbladder carcinomas, gallbladder adenocarcinoma, renal cell carcinoma, clear cell renal cell carcinoma, transitional cell carcinoma, urothelial carcinomas, Wilms tumor, leukemia, acute lymphocytic leukemia (ALL), acute myeloid leukemia (AML), chronic lymphocytic leukemia (CLL), chronic myeloid leukemia (CML), chronic myelomonocytic leukemia (CMML), liver cancer, liver carcinoma, hepatoma, hepatocellular carcinoma, cholangiocarcinoma, hepatoblastoma, Lung cancer, non-small cell lung cancer (NSCLC), mesothelioma, B-cell lymphomas, non-Hodgkin lymphoma, diffuse large B-cell lymphoma, Mantle cell lymphoma, T cell lymphomas, non-Hodgkin lymphoma, precursor T-lymphoblastic lymphoma/leukemia, peripheral T cell lymphomas, multiple myeloma, nasopharyngeal carcinoma (NPC), neuroblastoma, oropharyngeal cancer, oral cavity squamous cell carcinomas, osteosarcoma, ovarian carcinoma, pancreatic cancer, pancreatic ductal adenocarcinoma, pseudopapillary neoplasms, acinar cell carcinomas. Prostate cancer, prostate adenocarcinoma, skin cancer, melanoma, malignant melanoma, cutaneous melanoma, small intestine carcinomas, stomach cancer, gastric carcinoma, gastrointestinal stromal tumor (GIST), uterine cancer, or uterine sarcoma. Type and/or stage of cancer can be detected from genetic variations including mutations, rare mutations, indels, copy number variations, transversions, translocations, inversion, deletions, aneuploidy, partial aneuploidy, polyploidy, chromosomal instability, chromosomal structure alterations, gene fusions, chromosome fusions, gene truncations, gene amplification, gene duplications, chromosomal lesions, DNA lesions, abnormal changes in nucleic acid chemical modifications abnormal changes in epigenetic patterns, and abnormal changes in nucleic acid 5-methylcytosine.

Genetic data can also be used for characterizing a specific form of cancer. Cancers are often heterogeneous in both composition and staging. Genetic profile data may allow characterization of specific sub-types of cancer that may be important in the diagnosis or treatment of that specific sub-type. This information may also provide a subject or practitioner clues regarding the prognosis of a specific type of cancer and allow either a subject or practitioner to adapt treatment options in accord with the progress of the disease. Some cancers can progress to become more aggressive and genetically unstable. Other cancers may remain benign, inactive or dormant. The system and methods of this disclosure may be useful in determining disease progression.

Further, the methods of the disclosure may be used to characterize the heterogeneity of an abnormal condition in a subject. Such methods can include, e.g., generating a genetic profile of extracellular polynucleotides derived from the subject, wherein the genetic profile comprises a plurality of data resulting from copy number variation and rare mutation analyses. In some embodiments, an abnormal condition is cancer. In some embodiments, the abnormal condition may be one resulting in a heterogeneous genomic population. In the example of cancer, some tumors are known to comprise tumor cells in different stages of the cancer. In other examples, heterogeneity may comprise multiple foci of disease. Again, in the example of cancer, there may be multiple tumor foci, perhaps where one or more foci are the result of metastases that have spread from a primary site.

The present methods can be used to generate or profile, fingerprint or set of data that is a summation of genetic information derived from different cells in a heterogeneous disease. This set of data may comprise copy number variation, epigenetic variation, and mutation analyses alone or in combination.

The present methods can be used to diagnose, prognose, monitor or observe cancers, or other diseases. In some embodiments, the methods herein do not involve the diagnosing, prognosing or monitoring a fetus and as such are not directed to non-invasive prenatal testing. In other embodiments these methodologies may be employed in a pregnant subject to diagnose, prognose, monitor or observe cancers or other diseases in an unborn subject whose DNA and other polynucleotides may co-circulate with maternal molecules.

Non-limiting examples of other genetic-based diseases, disorders, or conditions that are optionally evaluated using the methods and systems disclosed herein include achondroplasia, alpha-1 antitrypsin deficiency, antiphospholipid syndrome, autism, autosomal dominant polycystic kidney disease, Charcot-Marie-Tooth (CMT), cri du chat, Crohn's disease, cystic fibrosis, Dercum disease, down syndrome, Duane syndrome, Duchenne muscular dystrophy, Factor V Liden thrombophilia, familial hypercholesterolemia, familial Mediterranean fever, fragile X syndrome, Gaucher disease, hemochromatosis, hemophilia, holoprosencephaly, Huntington's disease, Klinefelter syndrome, Marfan syndrome, myotonic dystrophy, neurofibromatosis, Noonan syndrome, osteogenesis imperfecta, Parkinson's disease, phenylketonuria, Poland anomaly, *porphyria*, progeria, retinitis pigmentosa, severe combined immunodeficiency (SCID), sickle cell disease, spinal muscular atrophy, Tay-Sachs, thalassemia, trimethylaminuria, Turner syndrome, velocardiofacial syndrome, WAGR syndrome, Wilson disease, or the like.

In some embodiments, a method described herein comprises detecting a presence or absence of DNA originating or derived from a tumor cell at a preselected timepoint following a previous cancer treatment of a subject previously diagnosed with cancer using a set of sequence information obtained as described herein. The method may further comprise determining a cancer recurrence score that is indicative of the presence or absence of the DNA originating or derived from the tumor cell for the test subject.

Where a cancer recurrence score is determined, it may further be used to determine a cancer recurrence status. The cancer recurrence status may be at risk for cancer recurrence, e.g., when the cancer recurrence score is above a predetermined threshold. The cancer recurrence status may be at low or lower risk for cancer recurrence, e.g., when the cancer recurrence score is above a predetermined threshold. In particular embodiments, a cancer recurrence score equal to the predetermined threshold may result in a cancer recurrence status of either at risk for cancer recurrence or at low or lower risk for cancer recurrence.

In some embodiments, a cancer recurrence score is compared with a predetermined cancer recurrence threshold, and the test subject is classified as a candidate for a subsequent caner treatment when the caner recurrence score is above the caner recurrence threshold or not a candidate for therapy when the caner recurrence score is below the cancer recurrence threshold. In particular embodiments, a caner recurrence score equal to the caner recurrence threshold may result in classification as either a candidate for a subsequent cancer treatment or not a candidate for therapy.

The methods discussed above may further comprise any compatible feature or features set forth elsewhere herein, including in the section regarding methods of determining a risk of cancer recurrence in a test subject and/or classifying a test subject as being a candidate for a subsequent cancer treatment.

2. Methods of Determining a Risk of Cancer Recurrence in a Test Subject and/or Classifying a Test Subject as being a Candidate for a Subsequent Cancer Treatment In some embodiments, a method provided herein is a method of determining a risk of cancer recurrence in a test subject. In some embodiments, a method provided herein is a method of classifying a test subject as being a candidate for a subsequent cancer treatment.

Any of such methods may comprise collecting DNA (e.g., originating or derived from a tumor cell) from the test subject diagnosed with the cancer at one or more preselected timepoints following one or more previous cancer treatments to the test subject. The subject may be any of the subjects described herein. The DNA may be cfDNA. The DNA may be obtained from a tissue sample.

Any of such methods may comprise capturing a plurality of sets of target regions from DNA from the subject, wherein the plurality of target region sets comprises a sequence-variable target region set and an epigenetic target region set, whereby a captured set of DNA molecules is produced. The capturing step may be performed according to any of the embodiments described elsewhere herein.

In any of such methods, the previous cancer treatment may comprise surgery, administration of a therapeutic composition, and/or chemotherapy.

Any of such methods may comprise sequencing the captured DNA molecules, whereby a set of sequence information is produced. The captured DNA molecules of the sequence-variable target region set may be sequenced to a greater depth of sequencing than the captured DNA molecules of the epigenetic target region set.

Any of such methods may comprise detecting a presence or absence of DNA originating or derived from a tumor cell at a preselected timepoint using the set of sequence information. The detection of the presence or absence of DNA originating or derived from a tumor cell may be performed according to any of the embodiments thereof described elsewhere herein.

Methods of determining a risk of cancer recurrence in a test subject may comprise determining a cancer recurrence score that is indicative of the presence or absence, or amount, of the DNA originating or derived from the tumor cell for the test subject. The cancer recurrence score may further be used to determine a cancer recurrence status. The cancer recurrence status may be at risk for cancer recurrence, e.g., when the cancer recurrence score is above a predetermined threshold. The cancer recurrence status may be at low or lower risk for cancer recurrence, e.g., when the cancer recurrence score is above a predetermined threshold. In particular embodiments, a cancer recurrence score equal to the predetermined threshold may result in a cancer recurrence status of either at risk for cancer recurrence or at low or lower risk for cancer recurrence.

Methods of classifying a test subject as being a candidate for a subsequent cancer treatment may comprise comparing the cancer recurrence score of the test subject with a predetermined cancer recurrence threshold, thereby classifying the test subject as a candidate for the subsequent cancer treatment when the cancer recurrence score is above the cancer recurrence threshold or not a candidate for therapy when the cancer recurrence score is below the cancer recurrence threshold. In particular embodiments, a cancer recurrence score equal to the cancer recurrence threshold may result in classification as either a candidate for a subsequent cancer treatment or not a candidate for therapy. In some embodiments, the subsequent cancer treatment comprises chemotherapy or administration of a therapeutic composition.

Any of such methods may comprise determining a disease-free survival (DFS) period for the test subject based on the cancer recurrence score; for example, the DFS period may be 1 year, 2 years, 3, years, 4 years, 5 years, or 10 years.

In some embodiments, the set of sequence information comprises sequence-variable target region sequences, and determining the cancer recurrence score may comprise determining at least a first subscore indicative of the amount of SNVs, insertions/deletions, CNVs and/or fusions present in sequence-variable target region sequences.

In some embodiments, a number of mutations in the sequence-variable target regions chosen from 1, 2, 3, 4, or 5 is sufficient for the first subscore to result in a cancer recurrence score classified as positive for cancer recurrence. In some embodiments, the number of mutations is chosen from 1, 2, or 3.

In some embodiments, the set of sequence information comprises epigenetic target region sequences, and determining the cancer recurrence score comprises determining a second subscore indicative of the amount of abnormal sequence reads in the epigenetic target region sequences. Abnormal sequence reads may be reads indicative of an epigenetic state different from DNA found in a corresponding sample from a healthy subject (e.g., cfDNA found in a blood sample from a healthy subject, or DNA found in a tissue sample from a healthy subject where the tissue sample is of the same type of tissue as was obtained from the test subject). The abnormal reads may be consistent with epigenetic changes associated with cancer, e.g., methylation of hypermethylation variable target regions and/or perturbed fragmentation of fragmentation variable target regions, where "pertubed" means different from DNA found in a corresponding sample from a healthy subject.

In some embodiments, a proportion of reads corresponding to the hypermethylation variable target region set and/or fragmentation variable target region set that indicate hypermethylation in the hypermethylation variable target region set and/or abnormal fragmentation in the fragmentation variable target region set greater than or equal to a value in the range of 0.001%-10% is sufficient for the second subscore to be classified as positive for cancer recurrence. The range may be 0.001%-1%, 0.005%-1%, 0.01%-5%, 0.01%-2%, or 0.01%-1%.

In some embodiments, any of such methods may comprise determining a fraction of tumor DNA from the fraction of reads in the set of sequence information that indicate one or more features indicative of origination from a tumor cell. This may be done for reads corresponding to some or all of the epigenetic target regions, e.g., including one or both of hypermethylation variable target regions and fragmentation variable target regions (hypermethylation of a hypermethylation variable target region and/or abnormal fragmentation of a fragmentation variable target region may be considered indicative of origination from a tumor cell). This may be done for reads corresponding to sequence variable target regions, e.g., reads comprising alterations consistent with cancer, such as SNVs, indels, CNVs, and/or fusions. The fraction of tumor DNA may be determined based on a combination of reads corresponding to epigenetic target regions and reads corresponding to sequence variable target regions.

Determination of a cancer recurrence score may be based at least in part on the fraction of tumor DNA, wherein a fraction of tumor DNA greater than a threshold in the range of $10^{-11}$ to 1 or $10^{-10}$ to 1 is sufficient for the cancer recurrence score to be classified as positive for cancer recurrence. In some embodiments, a fraction of tumor DNA greater than or equal to a threshold in the range of $10^{-10}$ to $10^{-9}$, $10^{-9}$ to $10^{-8}$, $10^{-8}$ to $10^{-7}$, $10^{-7}$ to $10^{-6}$, $10^{-6}$ to $10^{-5}$, $10^{-5}$ to $10^{-4}$, $10^{-4}$ to $10^{-3}$, $10^{-3}$ to $10^{-2}$, or $10^{-2}$ to $10^{-1}$ is sufficient for the cancer recurrence score to be classified as positive for cancer recurrence. In some embodiments, the fraction of tumor DNA greater than a threshold of at least $10^{-7}$ is sufficient for the cancer recurrence score to be classified as positive for cancer recurrence. A determination that a fraction of tumor DNA is greater than a threshold, such as a threshold corresponding to any of the foregoing embodiments, may be made based on a cumulative probability. For example, the sample was considered positive if the cumulative probability that the tumor fraction was greater than a threshold in any of the foregoing ranges exceeds a probability threshold of at least 0.5, 0.75, 0.9, 0.95, 0.98, 0.99, 0.995, or 0.999. In some embodiments, the probability threshold is at least 0.95, such as 0.99.

In some embodiments, the set of sequence information comprises sequence-variable target region sequences and epigenetic target region sequences, and determining the cancer recurrence score comprises determining a first subscore indicative of the amount of SNVs, insertions/deletions, CNVs and/or fusions present in sequence-variable target region sequences and a second subscore indicative of the amount of abnormal sequence reads in epigenetic target region sequences, and combining the first and second subscores to provide the cancer recurrence score. Where the first and second subscores are combined, they may be combined by applying a threshold to each subscore independently (e.g., greater than a predetermined number of mutations (e.g., >1) in sequence-variable target regions, and greater than a predetermined fraction of abnormal (e.g., tumor) reads in epigenetic target regions), or training a machine learning classifier to determine status based on a plurality of positive and negative training samples.

In some embodiments, a value for the combined score in the range of −4 to 2 or −3 to 1 is sufficient for the cancer recurrence score to be classified as positive for cancer recurrence.

In any embodiment where a cancer recurrence score is classified as positive for cancer recurrence, the cancer recurrence status of the subject may be at risk for cancer recurrence and/or the subject may be classified as a candidate for a subsequent cancer treatment.

In some embodiments, the cancer is any one of the types of cancer described elsewhere herein, e.g., colorectal cancer.

3. Therapies and Related Administration

In certain embodiments, the methods disclosed herein relate to identifying and administering customized therapies to patients given the status of a nucleic acid variant as being of somatic or germline origin. In some embodiments, essentially any cancer therapy (e.g., surgical therapy, radiation therapy, chemotherapy, and/or the like) may be included as part of these methods. Typically, customized therapies include at least one immunotherapy (or an immunotherapeutic agent). Immunotherapy refers generally to methods of enhancing an immune response against a given cancer type. In certain embodiments, immunotherapy refers to methods of enhancing a T cell response against a tumor or cancer.

In certain embodiments, the status of a nucleic acid variant from a sample from a subject as being of somatic or germline origin may be compared with a database of comparator results from a reference population to identify customized or targeted therapies for that subject. Typically, the reference population includes patients with the same cancer or disease type as the test subject and/or patients who are receiving, or who have received, the same therapy as the test subject. A customized or targeted therapy (or therapies) may be identified when the nucleic variant and the comparator results satisfy certain classification criteria (e.g., are a substantial or an approximate match).

In certain embodiments, the customized therapies described herein are typically administered parenterally (e.g., intravenously or subcutaneously). Pharmaceutical compositions containing an immunotherapeutic agent are typically administered intravenously. Certain therapeutic agents ae administered orally. However, customized therapies (e.g., immunotherapeutic agents, etc.) may also be administered by methods such as, for example, buccal, sublingual, rectal, vaginal, intraurethral, topical, intraocular, intranasal, and/or intraauricular, which administration may include tablets, capsules, granules, aqueous suspensions, gels, sprays, suppositories, salves, ointments, or the like.

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the disclosure described herein may be employed in practicing the invention. It is therefore contemplated that the disclosure shall also cover any such alternatives, modifications, variations or equivalents. It is intended that the following claims define the scope of the invention and that methods and structures within the scope of these claims and their equivalents be covered thereby.

While the foregoing disclosure has been described in some detail by way of illustration and example for purposes of clarity and understanding, it will be clear to one of ordinary skill in the art from a reading of this disclosure that various changes in form and detail can be made without departing from the true scope of the disclosure and may be practiced within the scope of the appended claims. For example, all the methods, systems, computer readable media, and/or component features, steps, elements, or other aspects thereof can be used in various combinations.

All patents, patent applications, websites, other publications or documents, accession numbers and the like cited herein are incorporated by reference in their entirety for all purposes to the some extent as if each individual item were specifically and individually indicated to be so incorporated by reference. If different versions of a sequence are associated with an accession number at different times, the version associated with the accession number at the effective filing date of this application is meant. The effective filing date means the earlier of the actual filing date or filing date of a priority application referring to the accession number, if applicable. Likewise, if different versions of a publication, website or the like are published at different times, the version most recently published at the effective filing date of the application is meant, unless otherwise indicated.

VII. Examples i) Characterization of Target Region Probe Sets with Different Concentrations of Probes for a Sequence-Variable Target Region Set and Probes for an Epigenetic Target Region Set This example describes an evaluation of the performance of probe sets containing probes for a sequence-variable target region set and probes for an epigenetic target region set as part of an effort to combine epigenetic and genotypic analysis of liquid biopsy cfDNA.

Samples of cfDNA were processed prior to being contacted with a target region probe set by performing partitioning based on methylation status, end repair, ligation with adapters, and amplified by PCR (e.g., using primers targeted to the adapters).

The processed samples were contacted with target region probe sets comprising probes for a sequence-variable target region set and probes for an epigenetic target region set. The target region probes were in the form of biotinylated oligonucleotides designed to tile the regions of interest. The probes for the sequence-variable target region set had a footprint of about 50 kb and the probes for the epigenetic target region set had a target region footprint of about 500 kb. The probes for the sequence-variable target region set comprised oligonucleotides targeting a selection of regions identified in Tables 3-5 and the probes for the epigenetic target region set comprised oligonucleotides targeting a selection of hypermethylation variable target regions, hypomethylation variable target regions. CTCF binding target regions, transcription start site target regions, focal amplification target regions, and methylation control regions.

Captured cfDNA isolated in this way was then prepared for sequencing and sequenced using an Illumina HiSeq or NovaSeq sequencer. Results were analyzed with respect to diversity (number of unique families of sequence reads) and read family size (number of individual reads in each family) of the sequence reads corresponding to the probes for the sequence-variable target region set and the probes for the epigenetic target region set. The values reported below were obtained using 70 ng input DNA. 70 ng input is considered a relatively high amount and represents a challenging condition for maintaining desired levels of diversity and family size.

Probe ratios of 2:1 and 5:1 (mass per volume concentration ratios of the epigenetic: sequence-variable probe sets) gave reductions in diversity for the sequence-variable target regions, indicating that the amount of epigenetic target regions resulted in interference with generating the expected number of distinct read families from the sequence-variable target regions.

Probe ratios of 1:2 or 1:5 (epigenetic:sequence-variable probe sets) gave higher levels of diversity for the sequence-variable target regions, which were generally close to the expected number of distinct read families, indicating that at these ratios, the presence of the epigenetic target regions were not present in amounts that substantially interfered with generating the expected number of distinct read families from the sequence-variable target regions.

For the epigenetic target regions, all ratios gave diversity levels substantially lower than the expected number of distinct read families. This is not considered problematic, however, given that analysis of methylation, copy number, and the like for the epigenetic target regions does not require dense and deep sequencing coverage to the same extent as determining the presence or absence of nucleotide substitutions or indels as intended for the sequence-variable regions.

ii) Detection of Cancer Using Combined Epigenetic and Sequence-Variable Target Region Sets Cohorts of cfDNA samples from cancer patients with different stages of cancer from I to IVA (7 stages total) are analyzed as described above using probes at the 1:5 (epigenetic:sequence-variable probe sets) ratio. The sequence-variable target region sequences are analyzed by detecting genomic alterations such as SNVs, insertions, deletions and fusions that can be called with enough support to discriminate real tumor variants from technical errors. The epigenetic target region sequences are analyzed independently to detect methylated fragments in regions that have been shown to be differentially methylated in cancer compared to blood cells. Finally, the results of both analyses are combined to produce a final tumor present/absent call to determine whether they showed a profile consistent with cancer at 95% specificity.

Figure 3:
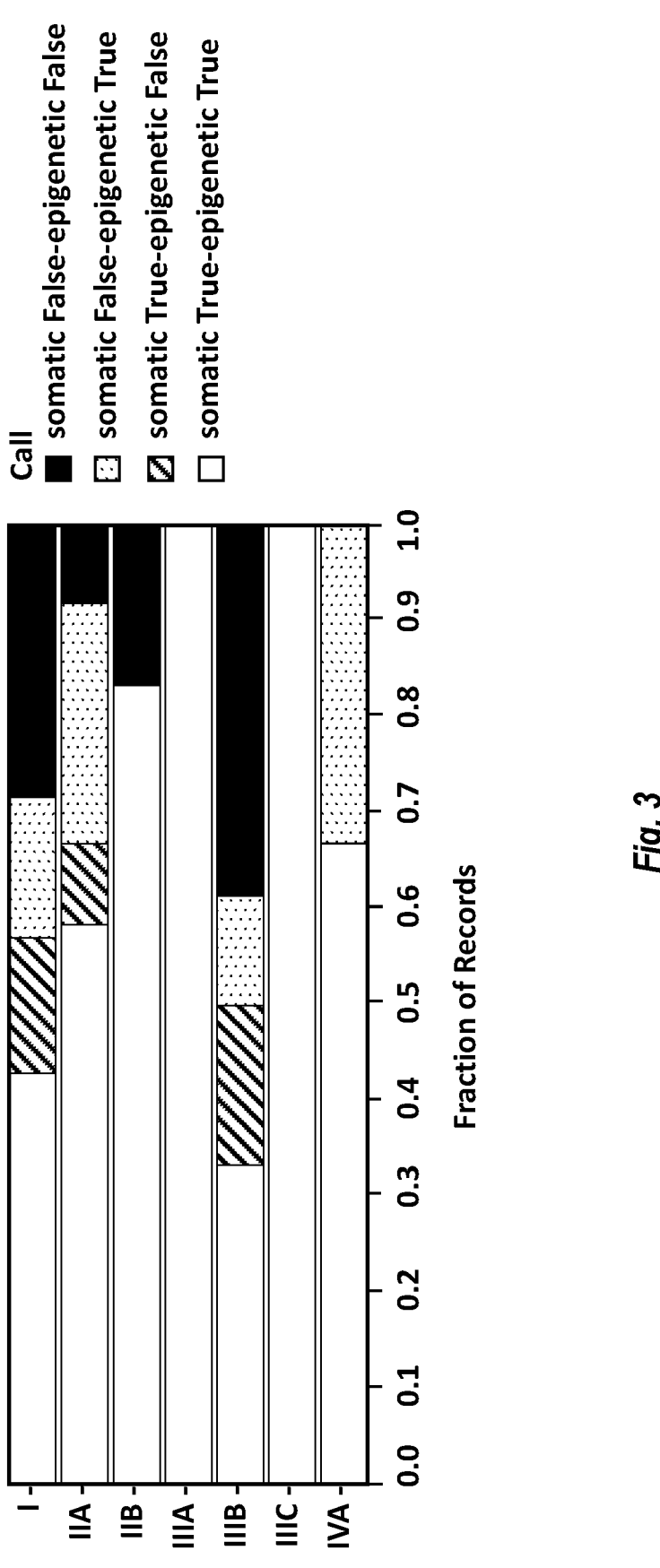
FIG. 3 shows sensitivity of detection of cancers of different stages using one or both of epigenetic target regions and sequence-variable target regions in a liquid biopsy test as described in Example ii.

FIG. 3 shows the sensitivity of detection of cancer based on sequence-variable target region sequences and the epigenetic target region sequences alone and in combination. Detection of cancer was 100% sensitive for either approach alone for the stage IIA and IIIC cohorts. For all but one of the other cohorts, including analysis of the epigenetic target region sequences increased sensitivity by about 10-30%. The one exception was the stage IIB cohort, in which every sample was either a true positive according to both approaches or a false negative according to both approaches.

Thus, the disclosed methods and compositions can provide captured cfDNA usable for concurrently sequencing epigenetic and sequence-variable target regions to different sequencing depths in sensitive, combined sequence-based and epigenetic detection of cancer.

iii) Identification of Risk Level of Recurrence of Colorectal Cancer

An assay was developed and performed to identify whether patients treated for colorectal cancer (CRC) had a high risk of recurrence. Plasma samples (3 to 4 mL) were taken from 72 patients who underwent standard of care treatment for CRC (surgery+/−neoadjuvant therapy in 42 cases and adjuvant therapy+/−neoadjuvant therapy in 30 cases).

cfDNA was extracted from the samples (median amount 27 ng) and analyzed using a method essentially as described herein that was validated in early stage CRC and that integrates assessments of genomic alterations and epigenomic features indicative of cancer including hypermethylation variable target regions. The method differentiates tumor derived from non-tumor derived alterations (e.g. germline or clonal hematopoiesis of indeterminate potential (CHIP) alterations) in a tumor tissue uninformed approach (LUNAR assay, Guardant Health, CA). The assay uses a single input sample and integrates the detection of genomic alterations with quantification of epigenomic signals associated with cancer, and was validated using 80 plasma samples from 50-75 year old presumptive cancer-free donors, and resulted in a single false positive (99% specificity). Analytical sensitivity (limit of detection) was established using a dilution series of 4 different late stage CRC pts tested in triplicate at a clinically relevant DNA input (30 ng) across multiple batches. 100% sensitivity was maintained even at the lowest tested level (estimated 0.1% tumor level).

Post-completion of SOC therapy plasms samples were collected a median of 31 days after surgical resection (N=42) or a median of 37 days after adjuvant therapy completion (N=27). Median follow-up was 515 days (33-938 days). Samples were considered positive for ctDNA if either genomic or epigenomic alterations indicative of cancer were detected. Genomic alterations were detected using Guardant Health's Digital Sequencing platform to differentiate real mutations from sequencing errors. A variant filter was applied to differentiate tumor mutations from non-tumor mutations (such as CHIP). Epigenomic calls were based on measuring whether the methylation rate observed in tumor hypermethylated regions is higher than expected based on methylation levels in the blood. Specifically, in this embodiment, the genomic results were considered positive if the number of cancer-indicative genomic alterations detected exceeded a threshold, where the threshold was 1, 2, or 3 alterations. The epigenomic results included analysis of methylation to determine the proportion of reads that indicate hypermethylation in the hypermethylation variable target region set. An overall "tumor fraction" was also calculated based on the overall proportion of reads that had tumor-like characteristics based on methylation, and the sample was considered positive if the cumulative probability that the tumor fraction was greater than or equal to $10^{-7}$ exceeded a probability threshold of 0.99. 14 total samples were positive, of which 10 were positive for both the epigenomic and genomic prongs, 3 were positive for the epigenomic prong only, and 1 was positive for the genomic prong only.

7/11 patients with a recurrence at 1 year following surgery were positive for ctDNA detected after CRC resection. 30/31 patients who were recurrence-free at 1 year following surgery were negative for ctDNA post CRC resection. 20/22 patients who were recurrence-free at 1 year following adjuvant therapy were negative for ctDNA post completion of SOC adjuvant therapy. 4/5 patients with a recurrence at 1 year following adjuvant therapy were positive for ctDNA post completion of SOC adjuvant therapy. Overall, ctDNA detection after completion of standard of care therapy had a recurrence positive predictive value (PPV) of 100%, negative predictive value (NPV) of 76%, and a hazard ratio for recurrence of 9.22 (p<0.0001) (FIG. 4).

Assay performance statistics for the genomic prong only and for the integrated analysis using the genomic and epigenomic prongs are summarized in the following table.

TABLE 6

| Assay Performance | Genomic (N) | Genomic + Epigenomic (N) |
|---|---|---|
| Positive Predictive Value (N of patients with ctDNA detected who recurred) | 100% (11/11) | 100% (14/14) |
| Negative Predictive Value (N of patients with ctDNA not detected who were recurrence free) | 72% (42/58) | 76% (42/55) |
| Sensitivity for recurrence within one year of surgery | 56% (9/16) | 69% (11/16) |
| Specificity for being recurrence free within one year of surgery | 96% (51/53) | 94% (50/53) |

Cohort results by genomic sequencing versus epigenomic analysis. Of the 14 patients who were ctDNA positive after completion of SOC therapy, 10 were positive for both by genomic and epigenomic assessment.

In the surgery cohort, ctDNA detection had a recurrence Positive Predictive Value (PPV) of 100%. Negative Predictive Value (NPV) of 76%, and a hazard ratio for recurrence of 8.7 (p<0.0001). In the adjuvant therapy cohort, ctDNA detection had a recurrence PPV of 100%. NPV of 76%, and a hazard ratio for recurrence of 9.3 (p<0.0001).

Patients negative for ctDNA following completion of therapy were further classified on whether they were positive or negative for ctDNA before therapy. Patients who were positive before and negative after therapy were termed "cleared" while patients who were negative before and after were termed "negative." The cleared population contained 6 individuals, of whom 3 recurred and 3 did not. The negative population contained 26 individuals, of whom 7 recurred and 19 did not.

Thus, in resected CRC, ctDNA detection utilizing a plasma only, tumor uninformed integrated genomic and epigenomic assay has high recurrence PPV and NPV following completion of standard of care therapy. In the post-resection setting, ctDNA detection identifies patients who may benefit from adjuvant therapy. After completion of adjuvant therapy, ctDNA detection identifies patients who may benefit from additional or modified therapy. These findings demonstrate that ctDNA from a single blood draw post-resection or post-adjuvant therapy can identify high risk patients and inform therapeutic decision making. In contrast, current ctDNA residual disease detection approaches only assess genomic alterations, are limited by low levels of ctDNA, and rely on tumor tissue sequencing to differentiate tumor derived alterations from confounding non-tumor derived alterations (e.g. clonal hematopoiesis of indeterminate potential; CHIP).

What is claimed is:

1. A method of analyzing cfDNA, the method comprising:
a) collecting cfDNA from a test subject,
b) capturing a plurality of sets of target regions from the cfDNA or one or more fractions thereof, wherein the plurality of target region sets comprises a sequence-variable target region set and an epigenetic target region set, whereby a captured set of cfDNA molecules is produced; and the capturing of cfDNA molecules is performed such that cfDNA molecules corresponding to the sequence-variable target region set are captured in the captured set of cfDNA molecules with a greater capture yield than cfDNA molecules corresponding to the epigenetic target region set; and
c) sequencing the captured cfDNA molecules, wherein the captured cfDNA molecules of the sequence-variable target region set are sequenced to at least a 2-fold greater depth of sequencing than the captured cfDNA molecules of the epigenetic target region set.

2. The method of claim 1, wherein capturing the plurality of sets of target regions of the cfDNA comprises contacting the cfDNA with target-binding probes specific for the sequence-variable target region set and target-binding probes specific for the epigenetic target region set.

3. The method of claim 1, wherein the captured cfDNA molecules of the sequence-variable target region set are sequenced to at least a 10-fold greater depth of sequencing than the captured cfDNA molecules of the epigenetic target region set.

4. The method of claim 1, wherein the captured cfDNA molecules of the sequence-variable target region set are pooled with the captured cfDNA molecules of the epigenetic target region set before sequencing.

5. The method of claim 1, wherein the captured cfDNA molecules of the sequence-variable target region set and the captured cfDNA molecules of the epigenetic target region set are sequenced in the same sequencing cell.

6. The method of claim 1, further comprising partitioning the cfDNA collected from the test subject into at least two fractions on the basis of methylation level, wherein the partitioning occurs prior to capturing the plurality of sets of target regions of the cfDNA.

7. The method of claim 6, wherein the partitioning comprises contacting the cfDNA collected from the test subject with a methyl binding reagent immobilized on a solid support.

8. The method of claim 1, wherein the cfDNA is amplified prior to the capturing of the plurality of sets of target regions of cfDNA.

9. The method of claim 8, wherein barcode-containing adapters are ligated to the cfDNA prior to the amplification.

10. The method of claim 1, wherein the capturing of the cfDNA corresponding to the sequence-variable target region set and the epigenetic target region set occur in the same solution.

11. The method of claim 1, wherein the capturing of the cfDNA corresponding to the sequence-variable target region set is performed in a first vessel and the capturing of the cfDNA corresponding to the epigenetic target region set is performed in a second vessel.

12. The method of claim 1, wherein the subject has or is suspected of having a tumor, the method further comprising:
d) obtaining a plurality of sequence reads generated by a nucleic acid sequencer from sequencing the captured cfDNA molecules;
e) mapping the plurality of sequence reads to one or more reference sequences to generate mapped sequence reads; and
f) processing the mapped sequence reads corresponding to the sequence-variable target region set and to the epigenetic target region set to determine presence of DNA produced by the tumor.

13. A method of analyzing cfDNA, the method comprising:
a) collecting cfDNA from a test subject,
b) capturing a plurality of sets of target regions from the cfDNA or one or more fractions thereof, wherein the plurality of target region sets comprises a sequence-variable target region set and an epigenetic target region set, whereby a captured set of cfDNA molecules is produced; and the capturing of cfDNA molecules is performed such that cfDNA molecules corresponding to the sequence-variable target region set are captured in the captured set of cfDNA molecules with a greater capture yield than cfDNA molecules corresponding to the epigenetic target region set; and
c) sequencing the captured cfDNA molecules, wherein the captured cfDNA molecules of the sequence-variable target region set are sequenced to a greater depth of sequencing than the captured cfDNA molecules of the epigenetic target region set, wherein a footprint of the epigenetic target region set is at least 10-fold greater than the footprint of the sequence-variable target region set.

14. The method of claim 1, wherein the epigenetic target region set comprises at least one of: (i) a hypermethylation variable target region set, (ii) a hypomethylation variable target region set, and (iii) a methylation control target region set.

15. A method of analyzing DNA, the method comprising:

a) collecting DNA originating or derived from a tumor from a test subject diagnosed with a cancer at one or more timepoints following one or more cancer treatments to the test subject;

b) contacting the DNA with a set of target-specific probes, wherein the set of target-specific probes comprises target-binding probes specific for a sequence-variable target region set and target-binding probes specific for an epigenetic target region set, and the set of target-specific probes is configured to capture DNA corresponding to the sequence-variable target region set with a greater capture yield than DNA corresponding to the epigenetic target region set, whereby complexes of target-specific probes and DNA are formed; and separating the complexes from DNA not bound to target-specific probes, thereby providing a set of captured DNA molecules; and c) sequencing the captured DNA molecules, wherein the captured DNA molecules of the sequence-variable target region set are sequenced to at least a 2-fold greater depth of sequencing than the captured DNA molecules of the epigenetic target region set, whereby a set of sequence information is produced.

16. The method of claim 15, wherein the DNA originating or derived from the tumor is cell-free DNA.

17. The method of claim 15, wherein the DNA originating or derived from the tumor is obtained from a tissue sample.

18. The method of claim 15, further comprising:

d) detecting a presence or absence of DNA originating or derived from the tumor at a timepoint using the set of sequence information; and e) determining a cancer recurrence score that is indicative of presence or absence of the DNA originating or derived from the tumor for the test subject, wherein a cancer recurrence status of the test subject is determined to be at risk for cancer recurrence when the cancer recurrence score is determined to be at or above a predetermined threshold or the cancer recurrence status of the test subject is determined to be at lower risk for cancer recurrence when the cancer recurrence score is below the predetermined threshold.

19. The method of claim 18, further comprising determining a disease-free survival (DFS) period for the test subject based on the cancer recurrence score.

20. The method of claim 19, wherein the DFS period is 1 year, 2 years, 3, years, 4 years, 5 years, or 10 years.

21. The method of claim 18, further comprising classifying the test subject as a candidate for a subsequent cancer treatment based on the cancer recurrence score.

22. The method of claim 21, wherein the subsequent cancer treatment comprises chemotherapy or administration of a therapeutic composition.

23. The method of claim 15, wherein the one or more timepoints is selected from the following group consisting of 1 month, 2 months, 3 months, 4 months, 5 months, 6 months, 7 months, 8 months, 9 months, 10 months, 11 months, 1 year, 1.5 years, 2 year, 3 years, 4 and 5 years after administration of the one or more cancer treatments.

24. The method of claim 15, wherein the one or more cancer treatments comprise at least one of: surgery, administration of a therapeutic composition, or chemotherapy.

25. The method of claim 15, wherein the DNA is amplified prior to the contacting of the DNA with a set of target-specific probes.

26. The method of claim 25, wherein barcode-containing adapters are ligated to the DNA prior to the amplification.

27. The method of claim 15, wherein the capturing of the DNA corresponding to the sequence-variable target region set and the epigenetic target region set occur in the same solution.

28. The method of claim 15, wherein the capturing of the DNA corresponding to the sequence-variable target region set is performed in a first vessel and the capturing of the DNA corresponding to the epigenetic target region set is performed in a second vessel.

29. A method of analyzing DNA, the method comprising:

a) collecting DNA originating or derived from a tumor from a test subject diagnosed with a cancer at one or more timepoints following one or more cancer treatments to the test subject;

b) contacting the DNA with a set of target-specific probes, wherein the set of target-specific probes comprises target-binding probes specific for a sequence-variable target region set and target-binding probes specific for an epigenetic target region set, and the set of target-specific probes is configured to capture DNA corresponding to the sequence-variable target region set with a greater capture yield than DNA corresponding to the epigenetic target region set, whereby complexes of target-specific probes and DNA are formed; and separating the complexes from DNA not bound to target-specific probes, thereby providing a set of captured DNA molecules; and c) sequencing the captured DNA molecules, wherein the captured DNA molecules of the sequence-variable target region set are sequenced to a greater depth of sequencing than the captured DNA molecules of the epigenetic target region set, whereby a set of sequence information is produced, wherein a footprint of sequence-variable target region set is at least 25 kB.

* * * * *